US012351614B2

(12) United States Patent
Kley et al.

(10) Patent No.: US 12,351,614 B2
(45) Date of Patent: Jul. 8, 2025

(54) CLEC9A-BASED CHIMERIC PROTEIN COMPLEXES

(71) Applicants: Orionis Biosciences, Inc., Waltham, MA (US); Orionis Biosciences BV, Zwijnaarde (BE)

(72) Inventors: Nikolai Kley, Waltham, MA (US); Erik Depla, Zwijnaarde (BE); Lennart Zabeau, Zwijnaarde (BE); Jan Tavernier, Zwijnaarde (BE)

(73) Assignees: Orionis Biosciences, Inc., Waltham, MA (US); Orionis Biosciences BV, Zwijnaarde (BE)

( * ) Notice: Subject to any disclaimer, the term of this patent is extended or adjusted under 35 U.S.C. 154(b) by 0 days.

(21) Appl. No.: 17/598,573

(22) PCT Filed: Mar. 27, 2020

(86) PCT No.: PCT/US2020/025423
§ 371 (c)(1),
(2) Date: Sep. 27, 2021

(87) PCT Pub. No.: WO2020/198662
PCT Pub. Date: Oct. 1, 2020

(65) Prior Publication Data
US 2022/0153801 A1    May 19, 2022

Related U.S. Application Data

(60) Provisional application No. 62/906,442, filed on Sep. 26, 2019, provisional application No. 62/825,584, filed on Mar. 28, 2019.

(51) Int. Cl.
| C07K 14/56 | (2006.01) |
| A61K 38/00 | (2006.01) |
| A61P 35/00 | (2006.01) |
| C07K 14/00 | (2006.01) |

(52) U.S. Cl.
CPC .............. *C07K 14/56* (2013.01); *A61P 35/00* (2018.01); *C07K 14/001* (2013.01); *A61K 38/00* (2013.01); *C07K 2319/30* (2013.01)

(58) Field of Classification Search
CPC ............... C07K 14/56; C07K 2319/30; C07K 2317/52; C07K 2317/569; C07K 2319/00; C07K 16/2851; A61P 35/00; A61K 38/00
See application file for complete search history.

(56) References Cited

U.S. PATENT DOCUMENTS

| 5,914,254 | A | 6/1999 | Mascarenhas et al. |
| 8,580,266 | B2 | 11/2013 | Sancho-Madrid et al. |
| 8,980,267 | B2 | 3/2015 | Grewal et al. |
| 9,139,634 | B2 | 9/2015 | Morrison et al. |
| 9,492,562 | B2 | 11/2016 | Tavernier et al. |
| 9,534,056 | B2 | 1/2017 | Grewal et al. |
| 9,732,135 | B2 | 8/2017 | Tavernier et al. |
| 9,878,014 | B2 | 1/2018 | Tavernier et al. |
| 9,914,759 | B2 | 3/2018 | Tavernier et al. |
| 9,932,409 | B2 | 4/2018 | Tavernier et al. |
| 10,034,919 | B2 | 7/2018 | Tavernier et al. |
| 10,035,835 | B2 | 7/2018 | Tavernier et al. |
| 10,072,059 | B2 | 9/2018 | Tavernier et al. |
| 10,407,480 | B2 | 9/2019 | Tavernier et al. |
| 10,640,542 | B2 | 5/2020 | Tavernier et al. |
| 10,787,493 | B2 | 9/2020 | Tavernier et al. |
| 10,906,985 | B2 | 2/2021 | Kley et al. |
| 10,946,070 | B2 | 3/2021 | Tavernier et al. |
| 10,947,288 | B2 | 3/2021 | Tavernier et al. |
| 10,988,538 | B2 | 4/2021 | Kley et al. |
| 11,001,631 | B2 | 5/2021 | Tavernier et al. |
| 11,084,859 | B2 | 8/2021 | Kley et al. |
| 11,236,141 | B2 | 2/2022 | Kley et al. |
| 11,236,166 | B2 | 2/2022 | Kley et al. |
| 11,246,911 | B2 | 2/2022 | Tavernier et al. |
| 11,248,057 | B2 | 2/2022 | Tavernier et al. |
| 2010/0172868 | A1 | 7/2010 | Morrison et al. |
| 2010/0297076 | A1 | 11/2010 | Morrison et al. |
| 2011/0020273 | A1 | 1/2011 | Chang et al. |
| 2011/0081341 | A1 | 4/2011 | Honjo et al. |
| 2011/0104112 | A1 | 5/2011 | Morrison et al. |
| 2011/0224407 | A1 | 9/2011 | Langer et al. |
| 2011/0274658 | A1 | 11/2011 | Silver et al. |

(Continued)

FOREIGN PATENT DOCUMENTS

| RU | 2011127226 A | 1/2013 |
| WO | WO 91/02754 A1 | 3/1991 |

(Continued)

OTHER PUBLICATIONS

Yan et al. Oncotarget. Jun. 28, 2016;7(26):40437-40450. (Year: 2016)*
Zeng et al. J Clin Invest. May 1, 2018;128(5):1971-1984. Epub Apr. 9, 2018 (Year: 2018).*
Tullett et al. JCI Insight. May 19, 2016;1(7):e87102. (Year: 2016).*
Acres, et al., "Fusokine Interleukin-2/Interleukin-18, a Novel Potent Innate and Adaptive Immune Stimulator with Decreased Toxicity," Cancer Res., vol. 65, No. 20, pp. 9536-9546, 2005.

(Continued)

Primary Examiner — Jeffrey Stucker
Assistant Examiner — Sarah Cooper Patterson
(74) Attorney, Agent, or Firm — Morgan, Lewis & Bockius LLP

(57) ABSTRACT

The present invention relates, in part, to chimeric protein complexes including an anti-Clec9A targeting moiety, a modified Fc domain, and a modified human IFNα and their use as therapeutic agents. The present invention further relates to pharmaceutical compositions comprising the chimeric protein complexes and their use in the treatment of various diseases.

5 Claims, 9 Drawing Sheets
Specification includes a Sequence Listing.

(56) References Cited

U.S. PATENT DOCUMENTS

| | | |
|---|---|---|
| 2013/0183298 A1 | 7/2013 | Le et al. |
| 2013/0230517 A1 | 9/2013 | Grewal et al. |
| 2014/0248238 A1 | 9/2014 | Wilson, Jr. et al. |
| 2014/0271462 A1 | 9/2014 | Ho et al. |
| 2014/0328865 A1 | 11/2014 | Sancho-Madrid et al. |
| 2014/0348789 A1 | 11/2014 | Tavernier et al. |
| 2015/0139951 A1 | 5/2015 | Grewal et al. |
| 2015/0265721 A1 | 9/2015 | Lahoud et al. |
| 2015/0299324 A1 | 10/2015 | Hofer et al. |
| 2015/0313965 A1 | 11/2015 | Pogue et al. |
| 2016/0075769 A1 | 3/2016 | Verheesen et al. |
| 2016/0145325 A1 | 5/2016 | Varheesen et al. |
| 2018/0186894 A1 | 7/2018 | Tavernier et al. |
| 2018/0333465 A1 | 11/2018 | Tavernier et al. |
| 2018/0334488 A1 | 11/2018 | Tavernier et al. |
| 2018/0334489 A1 | 11/2018 | Tavernier et al. |
| 2019/0010199 A1 | 1/2019 | Tavernier et al. |
| 2019/0071500 A1 | 3/2019 | Kley et al. |
| 2019/0144553 A1 | 5/2019 | Kley et al. |
| 2019/0194284 A1 | 6/2019 | Kley et al. |
| 2019/0202934 A1 | 7/2019 | Tavernier et al. |
| 2019/0351021 A1 | 11/2019 | Tavernier et al. |
| 2019/0352406 A1 | 11/2019 | Tavernier et al. |
| 2019/0367575 A1 | 12/2019 | Tavernier et al. |
| 2019/0367604 A1 | 12/2019 | Kley et al. |
| 2020/0071414 A1 | 3/2020 | Kley et al. |
| 2020/0087411 A1 | 3/2020 | Kley et al. |
| 2021/0024637 A1 | 1/2021 | Kley et al. |

FOREIGN PATENT DOCUMENTS

| | | |
|---|---|---|
| WO | WO 03/033720 A2 | 4/2003 |
| WO | WO 2006/053883 A1 | 4/2003 |
| WO | WO 2006/115800 A2 | 11/2006 |
| WO | WO 2008/014612 A1 | 2/2008 |
| WO | WO 2008/124086 A2 | 10/2008 |
| WO | WO 2009/003145 A1 | 12/2008 |
| WO | WO 2009/013484 A1 | 1/2009 |
| WO | WO 2009/039409 A1 | 3/2009 |
| WO | WO 2010/036918 A2 | 4/2010 |
| WO | WO 2010/066740 A1 | 6/2010 |
| WO | WO 2011/020783 A2 | 2/2011 |
| WO | WO 2011/029870 A1 | 3/2011 |
| WO | WO 2012/170072 A1 | 12/2012 |
| WO | WO 2013/053008 A2 | 4/2013 |
| WO | WO 2013/059885 A2 | 5/2013 |
| WO | WO 2013/107791 A1 | 7/2013 |
| WO | WO 2013/134138 A1 | 9/2013 |
| WO | WO 2013/163689 A1 | 11/2013 |
| WO | WO 2015/007520 A1 | 1/2015 |
| WO | WO 2015/007536 A2 | 1/2015 |
| WO | WO 2015/007542 A1 | 1/2015 |
| WO | WO 2015/007903 A1 | 1/2015 |
| WO | WO 2015/018528 A1 | 2/2015 |
| WO | WO 2016187459 A1 | 11/2016 |
| WO | WO 2017/077382 A1 | 5/2017 |
| WO | WO 2017/134301 A1 | 8/2017 |
| WO | WO 2017/134302 A2 | 8/2017 |
| WO | WO 2017/134305 A1 | 8/2017 |
| WO | WO 2017/134306 A1 | 8/2017 |
| WO | WO 2017/153402 A1 | 9/2017 |
| WO | WO 2017/194782 A2 | 11/2017 |
| WO | WO 2017/194783 A1 | 11/2017 |
| WO | WO 2018/077893 A1 | 5/2018 |
| WO | WO 2018/141964 A1 | 8/2018 |
| WO | WO 2018/144999 A1 | 8/2018 |
| WO | WO 2019/032661 A1 | 2/2019 |
| WO | WO 2019/032662 A1 | 2/2019 |
| WO | WO 2019/032663 A1 | 2/2019 |
| WO | WO 2019/148089 A1 | 8/2019 |
| WO | WO 2019/152979 A1 | 8/2019 |
| WO | WO 2019/191519 A1 | 10/2019 |
| WO | WO 2020/033646 A1 | 2/2020 |

OTHER PUBLICATIONS

Baba, et al., "Identification of CCR6, the Specific Receptor for a Novel Lymphocyte-Directed CC Chemokine LARC," The Journal of Biological Chemistry, vol. 272, No. 23, pp. 14893-14898, 1997.

Barbara, et al., "Dissociation of TNF-α cytotoxic and proinflammatory activities by p55 receptor-and p75 receptor-selective TNF-α mutants," EMBO Journal, vol. 13, No. 4, pp. 843-850, 1994.

Bork, et al., "Go hunting in sequence databases but watch out for the traps." Trends in Genetics, Oct. 1996, vol. 12, No. 10, pp. 425-427.

Bork, "Powers and Pitfalls in Sequence Analysis: The 70% Hurdle," Genome Research, vol. 10, pp. 398-400, 2000.

Boschert, et al., "Single chain TNF derivatives with individually mutated receptor binding sites reveal differential stoichiometry of ligand receptor complex formation for TNFR1 and TNFR2," Cellular Signalling 22 (7):1088-1096, 2010.

Bremer, et al., "Superior activity of fusion protein scFvRit:sFasL over cotreatment with rituximab and Fas agonists," Cancer Res. 68: 597-604, 2008.

Brown, et al., "Tolerance of single, but not multiple, amino acid replacements in antibody VH CDR 2: a means of minimizing B cell wastage from somatic hypermutation?," J. Immunol., May 1, 1996, vol. 156, No. 9, pp. 3285-3291. Abstract.

Camacho, et al., "Structure of an Interleukin-1β Mutant With Reduced Bioactivity Shows Multiple Subtle Changes in Conformation That Affect Protein-Protein Recognition," Biochemistry, vol. 32, No. 34, pp. 8749-8757, 1993.

Coulstock, et al., "Liver-Targeting of Interferon-Alpha with Tissue Specific Domain Antibodies," PLOS ONE, vol. 8, No. 2, pp. 1-11, 2013.

De Bruyn, et al., "Antibody-Based Fusion Proteins to Target Death Receptors in Cancer," Cancer Letters, vol. 332, pp. 175-183, 2013.

Deffar, et al., "Nanobodies—The New Concept in Antibody Engineering," African Journal of Biotechnology, vol. 8, No. 12, pp. 2645-2652, 2009.

Dijkmans, et al., "Murine Interferon-γ Interleukin-1 Fusion Proteins Used as Antigens for the Generation of Hybridomas Producing Monoclonal Anti-Interleukin-1 Antibodies," Cytokine, vol. 3, No. 2, pp. 134-140, 1991.

Dimitrov, "Engineered CH2 Domains (Nanoantibodies)," mAbs, Landes Bioscience, vol. 1, No. 1, pp. 26-28, 2009.

Edelman, et al., "The Covalent Structure of an Entire Tg Immunoglobulin Molecule*," Biochemistry, 1969; vol. 63, No. 1, 78-85.

Frey, et al., "Antibody-Based Targeting of Interferon-Alpha to the Tumor Neovasculature: A Critical Evaluation," ntegrative Biology, vol. 3, pp. 468-478, 2011.

Garcin, et al., "High Efficiency cell-specific targeting of cytokine activity," Nature Communications, vol. 5, No. 8, 9 pages, 2014.

Garlanda, et al., "The Interleukin-1 Family: Back to the Future," Immunity, 39 (6): pp. 1003-1018, Dec. 12, 2013.

Holler, et al., "Two Adjacent Trimeric Fas Ligands are Required for Fas Signaling and Formation of a Death-Inducing Signaling Complex," Molecular and Cellular Biology, vol. 23, No. 4, pp. 1428-1440, 2003.

Huang, et al., "A Trimeric Anti-HER2/neu ScFv and Tumor Necrosis Factor-[alpha] Fusion Protein Induces HER2/Neu Signaling and Facilitates Repair of Injured Epithelia," The Journal of Pharmacology and Experimental Therapeutics, vol. 316, No. 3, pp. 983-991, 2006.

International Search Report & Written Opinion, PCT Application No. PCT/EP2017/052544, dated Jun. 6, 2017, 16 pages.

International Search Report & Written Opinion, PCT Application No. PCT/EP2018/54742, dated Dec. 6, 2018, 20 pages.

Idoyaga, et al., "Comparable T helper 1 (Th1) and CD8 T-cell immunity by targeting HIV gag p24 to CD8 dendritic cells within antibodies to Langerin, DEC205, and Clec9A," PNAS, vol. 108, No. 6, pp. 2384-2389, Jan. 24, 2011.

Kircheis, et al., "Biological activity of mutants of human tumour necrosis factor-alpha," Immunology, pp. 433-438, Jul. 1, 1992.

Krippner-Heidenreich, et al., "Single-Chain TNF, a TNF Derivative with Enhanced Stability and Antitumoral Activity," The Journal of Immunology, vol. 180, pp. 8176-8183, 2008.

(56) References Cited

OTHER PUBLICATIONS

Lahoud, et al., "Targeting Antigen to Mouse Dendritic Cells via Clec9A Induces Potent CD4 T Cell Responses Biased toward a Follicular Helper Phenotype," The Journal of Immunology, vol. 187, No. 2, pp. 842-850, Jul. 15, 2011.
Loetscher, et al., "Human Tumor Necrosis Factor α (TNFα) Mutants with Exclusive Specificity for 55-kDA or 75-kDa TNF Receptors," Journal of Biological Chemistry, American Society for Biochemistry and Molecular Biology, US, vol. 268, No. 35, pp. 26350-26357, 1993.
Masci, et al., "New and Modified Interferon alfas: Preclinical and Clinical Data," Current Oncology Reports, vol. 5, pp. 108-113, 2003.
Merchant, et al., "An efficient route to human bispecific IgG.," Nature Biotechnology, 1998, vol. 16, pp. 677-681. Abstract.
Minn, "Interferons and the Immunogenic Effects of Cancer Therapy," Trends In Immunology, vol. 36, No. 11, pp. 725-737, Nov. 1, 2015.
Ngo, et al., "Computational Complexity, Protein Structure Prediction, and the Levinthal Paradox. The Protein Folding Problem and Tertiary Structure Prediction," Edited by: Mertz et al., (Birkhauser, Boston), pp. 491-495, 1994.
Pan, et al., "Mutation of the IFNAR-1 Receptor Binding Site of Human IFN-α2 Generates Type I IFN Competitive Antagonists," Biochemistry, vol. 47, pp. 12018-12027, 2008.
Patris, et al., "Nanoimmunoassay onto a screen printed electrode for HER2 breast cancer biomarker determination," Talanta, 2014, vol. 130, pp. 164-170, 2014.
Penafuerte, et al., "The Human Ortholog of Granulocyte Macrophage Colony-Stimulating Factor and Interleukin-2 fusion Protein Induces Potent Ex Vivo Natural Killer Cell Activation and Maturation," Cancer Res, vol. 69, No. 23, pp. 9020-9028, 2009.
Picco, et al., "Targeting DNGR-1 (CLEC9A) with antibody/MUC1 peptide conjugates as a vaccine for carcinomas," European Journal of Immunology, vol. 44, No. 7, pp. 1947-1955, Apr. 17, 2014.
Piehler, et al., New Structural and Functional Aspects of the Type I Interferon-Receptor Interaction Revealed by Comprehensive Mutational Analysis of the Binding Interface* JBC, 2000, vol. 275, No. 51, pp. 40425-40433.
Puskas, et al., "Development of an attenuated interleukin-2 fusion protein that can be activated by tumour-expressed proteases," Immunology, vol. 133, No. 2, pp. 206-220, Jun. 23, 2011.
Rafei, et al., "A MCP1 Fusokine with CCR2-Specific Tumoricidal Activity," Molecular Cancer, vol. 10, No. 121, pp. 1-11, 2011.
Rafei, et al., "An Engineered GM-CSF-CCL2 Fusokine Is a Potent Inhibitor of CCR2-Driven Inflammation as Demonstrated in a Murine Model of Inflammatory Arthritis," The Journal of Immunology, vol. 183, pp. 1759-1766, 2009.
Ridgway, et al., "'Knobs-into-holes' engineering of antibody CH3 domains for heavy chain heterodimerization," Protein Engineering, 1996, vol. 9, No. 7, pp. 617-621.
Roisman, et al., "Structure of the Interferon-Receptor Complex Determined by Distant Constraints from Double Mutant Cycles and Flexible Docking," PNAS, vol. 98, No. 23, pp. 13231-13236, 2001.
Rovero, et al., "Insertion of the DNA for the 163-171 Peptide of IL 1 II Enables a DNA Vaccine Encoding p185$^{neu}$ to inhibit Mammary Carcinogenesis in Her-2/neu Transgenic BALB/c Mice," Gene Therapy, vol. 8, pp. 447-452, 2001.
Rudikoff, et al., "Single amino acid substitution altering antigen-binding specificity," Proc. Natl. Acad. Sci. USA, Mar. 1982, vol. 79, pp. 1979-1983.
Sancho, et al., "Identification of a dendritic cell receptor that couples sensing of necrosis to immunity," Nature, Nature Publishing Group, United Kingdom, vol. 453, No. 7240, pp. 899-903, Apr. 16, 2009.
Schutyser, et al., "The CC Chemokine CCL20 and its Receptor CCR6," Cytokine & Growth Factor Reviews, vol. 14, pp. 409-426, 2003.
Vaneycken, et al., "Preclinical Screening of Anti-HER2 Nanobodies for Molecular Imaging of Breast Cancer", The ASEB Journal, vol. 25, pp. 2433-2446, 2011.
Vajdos, et al., "Comprehensive Functional Maps of the Antigen binding Site of an Anti-ErbB2 Antibody Obtained with Shotgun Scanning Mutagenesis", JMB, 2002, vol. 320, pp. 415-428.
Weber, et al., "Single Amino Acid Changes that Render Human IFN-α2 Biologically Active on Mouse Cells," The EMBO Journal, vol. 6, No. 3, pp. 591-598, 1987.
Wells, "Additivity of Mutational Effects in Proteins," Biochemistry, vol. 29, No. 37, pp. 8509-8517, 1990.
Wesolowski, et al., "Single Domain Antibodies: Promising Experimental and Therapeutic Tools in Infection and Immunity," Med. Microbiol. Immunol., vol. 198, pp. 157-174, 2009.
Zitvogel, et al., "Type I interferons in anticancer immunity," The Journal of Immunology, vol. 15, No. 7, pp. 405-141, Jun. 1, 2015.
International Search Report & Written Opinion, PCT Application No. PCT/US2020/025423, dated Jul. 22, 2020, 13 pages.
Paul, "Targeting of alpha interferon activity: from the evidence concept to biological activity," Thesis, Université Montpellier, Apr. 20, 2017, 196 pages.

* cited by examiner

CLEC9A-BASED CHIMERIC PROTEIN COMPLEXES

CROSS-REFERENCE TO RELATED APPLICATIONS

This application is a national stage entry of PCT/US2020/025423, filed Mar. 27, 2020, which claims the benefit of and priority to U.S. Provisional Patent Application No. 62/906,442, filed Sep. 26, 2019, and to U.S. Provisional Patent Application No. 62/825,584, filed Mar. 28, 2019, the content of which are hereby incorporated by reference in their entirety.

FIELD

The present invention relates, in part to, chimeric protein complexes that include a fragment crystallizable domain (Fc), a Clec9A VHH as a targeting moiety, and a modified interferon α2 (IFNα2) as a signaling agent. Use of these chimeric protein complexes as therapeutic agents is also disclosed.

SEQUENCE LISTING

The instant application contains a Sequence Listing that has been submitted in ASCII format via EFS-Web and is hereby incorporated by reference in its entirety. Said ASCII copy, recorded on Feb. 20, 2025, is named ORN-063_ST25.txt and is 136,206 bytes in size.

BACKGROUND

Biologics with an effector function are a class of biologics that have many potential therapeutic applications. In some instances, these biologics, e.g., cytokines, encode an effector functions that can be systemically toxic if administered to humans. Accordingly, maximizing tolerability and therapeutic index of these biologics in humans is important so that systemic toxicity in humans or subjects can be reduced.

Often, these biologics need be delivered to their target(s) inside a subject with high precision and in a regulated manner in order for them to be effective. Thus, there is a need for engineering biological molecules that have high inherent safety profile, have the ability to reach their target inside the subject with high precision, and are able to function in a regulated fashion.

One example of such biologics, is a chimeric protein having a signaling agent (having an effector function, e.g., a cytokine), connected to a targeting element (having the ability to seek its target with high precision). In these biologics, the signaling agent can be a wild type signaling agent or a modified signaling agent (e.g. by mutation). The modified signaling agent is, generally, modified to cause an attenuation of the signaling agent's activity (e.g., substantially reducing its ability to interact with/engage its receptor) in a manner such that the signaling agent's effector function can be recovered upon binding of the targeting element to its target (e.g., antigen on target cell). However, such chimeric proteins are amenable to therapeutic use only if certain conditions are met, e.g., the ability to be produced in a large scale, an in vivo half-life that ensures adequate time of exposure to the drug to elicit a therapeutically beneficial effect, a proper size to avoid rapid clearance or limited tissue penetrance and bio-distribution, and other properties that ensure adequate solubility, stability and storage without significant loss of function. Importantly all, or substantially most, of the above properties should be achieved without a loss of the conditional targeting of the effector function and retention of conditional engagement of a modified signaling agent with its receptor. Often, it is difficult to achieve all these objectives with chimeric proteins encoded or represented by a single, contiguous polypeptide chain. There is a need in the art where such desirable properties of the biologic can be achieved while maintaining the tolerability and therapeutic index of the biologic.

SUMMARY

The present technology provides chimeric protein complexes that comprise biological therapeutic agents whose effector function can be delivered in a highly precise fashion to a target of choice, with limited or no cross-reactivities, and with limited of no systemic adverse events, while also providing features that impart pharmaceutical properties enabling the production of therapeutic agents with, for example, desired in vivo exposure time (e.g. half-life), size (e.g. for biodistribution and clearance characteristics), as well as large scale production and/or purification for commercial production (e.g. having adequate solubility, stability and storage properties).

In one aspect, the present invention relates to a heterodimeric protein complex and its individual polypeptide chain subunits (components), and where the protein complex includes a targeting moiety that specifically binds to C-type lectin domain family 9 member A (Clec9A), a modified human IFNα2, and a modified Fc domain.

In an aspect, the present invention is related to a chimeric protein complex comprising: (i) a targeting moiety that specifically binds to C-type lectin domain family 9 member A (Clec9A), (ii) a modified human IFNα2, and (iii) a modified Fc domain.

In one aspect, the present invention relates to a chimeric protein complex where the chimeric protein complex includes a targeting moiety that specifically binds to C-type lectin domain family 9 member A (Clec9A), a modified human IFNα2, and a modified Fc domain.

In some embodiments, the chimeric protein complex comprises a polypeptide having at least 95% identity with any one of SEQ ID NOs: 1-4 and 43 or at least 98% identity with any one of SEQ ID NOs: 1-4 and 43 or at least 99% identity with any one of SEQ ID Nos: 1-4 and 43. In some embodiments, the chimeric protein complex comprises a polypeptide of any one of SEQ ID NOs: 1-4 and 43, optionally with 0, or 1, or 2, or 3, or 4, or 5 mutations. In some embodiments, the chimeric protein complex comprises a polypeptide of any one of SEQ ID NOs: 1-4 and 43.

In some embodiments, the chimeric protein complex comprises a polypeptide incorporating a contiguous amino acid sequence having at least 95% identity with any one of SEQ ID NOs: 1-4 and 43 or at least 98% identity with any one of SEQ ID NOs: 1-4 and 43.

In another aspect, the present invention relates to a method of treating or preventing a cancer, comprising administering an effective amount of the chimeric protein complex, as disclosed herein, to a patient in need thereof.

Another aspect of the present invention relates to a pharmaceutical composition comprising a chimeric protein complex, as disclosed herein, and a pharmaceutically acceptable carrier. In another aspect, the present invention relates to a method for treating or preventing a cancer, comprising administering an effective amount of the pharmaceutical composition as disclosed herein to a patient in need thereof. In another aspect, the present invention relates to a recombinant nucleic acid composition encoding one or more of the polypeptide chain subunits of chimeric protein complexes disclosed herein. In another aspect, the present invention relates to a host cell including a nucleic acid composition encoding one or more chimeric protein complexes disclosed herein.

DETAILED DESCRIPTION OF THE INVENTION

Figure 1:
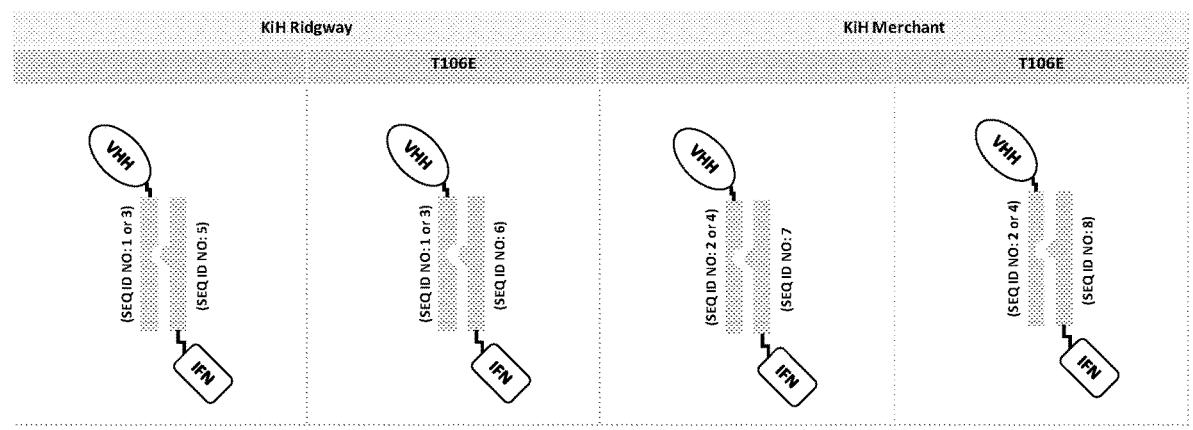
FIG. 1 shows various non-limiting illustrative schematics of the chimeric protein complexes of the present invention. In embodiments, each schematic is a composition of the present invention. Here "IFN" refers IFNα2, as described herein; "VHH" refers to anti-Clec9A VHH, as described herein; "⌐⌐" is an optional "linker" as described herein; and the two long parallel rectangles with one having a protrusion and the other having an indentation are human Fc domains from IgG1, with knob-in-hole mutations as described herein and, optionally, with effector knock-out and/or stabilization mutations as also described herein. Although SEQ ID Nos are shown, these are illustrative only, e.g. they will change if alternative mutations besides R149A, as described herein, are used.

In one aspect, the present invention relates to a chimeric protein complex where the chimeric protein complex includes a targeting moiety that specifically binds to C-type lectin domain family 9 member A (Clec9A), a modified human IFNα2, and a modified Fc domain. In embodiments, the chimeric protein complex comprises a polypeptide having at least 95% identity with any one of SEQ ID NOs: 1-4 and 43. In embodiments, the chimeric protein complex comprises a polypeptide having at least 98% identity with any one of SEQ ID NOs: 1-4 and 43 or at least 99% identity with any one of SEQ ID Nos: 1-4 and 43. In embodiments, the chimeric protein complex comprises a polypeptide of SEQ ID NOs: 1-4 and 43 wherein the sequence has less than 10 mutations as compared to the selected sequence. In embodiments, the chimeric protein complex comprises a polypeptide of SEQ ID NOs: 1-4 and 43 wherein the sequence has less than 5 mutations as compared to the selected sequence.

In embodiments, the chimeric protein complex comprises a polypeptide that has an amino acid sequence of SEQ ID NO: 1. This sequence includes a single domain antibody (VHH) against Clec9A (i.e., R1CHCL50(opt4)), a linker (i.e., 5*GGS), and a Fc hole Ridgway sequence with LALA-KQ mutation (i.e., Fc hole Ridgway (LALA-KQ), see Ridgway et al., Protein Engineering 1996; 9:617-621, which is incorporated by reference in its entirety). This construct of sequence of SEQ ID NO: 1 is denoted as follows: Variation 1 VHH-Fc R1CHCL50(opt4)-5*GGS-Fc hole Ridgway (LALA-KQ).

In embodiments, the chimeric protein complex comprises a polypeptide that has an amino acid sequence of SEQ ID NO: 2. This sequence includes a single domain antibody (VHH) against Clec9A (i.e., R1CHCL50(opt4)), a linker (i.e., 5*GGS), and a Fc hole Merchant sequence with LALA-KQ mutation (i.e., Fc hole Merchant (LALA-KQ), see Merchant et al., Nature Biotechnology 1998; 16:677-681, which is incorporated by reference in its entirety). This construct of SEQ ID NO: 2 is denoted as follows: VHH-Fc: R1CHCL50(opt4)-5*GGS-Fc hole Merchant (LALA-KQ).

In embodiments, the chimeric protein complex comprises a polypeptide that has an amino acid sequence of SEQ ID NO: 3. This sequence includes a single domain antibody (VHH) against Clec9A (i.e., 3LEC89(opt4)), a linker (i.e., 5*GGS), and a Fc hole Ridgway sequence with LALA-KQ mutation (i.e., Fc hole Ridgway (LALA-KQ), see Ridgway et al., Protein Engineering 1996; 9:617-621, which is incorporated by reference in its entirety). This construct of SEQ ID NO: 3 is denoted as follows: VHH-Fc: 3LEC89(opt4)-5*GGS-Fc hole Ridgway (LALA-KQ)

In embodiments, the chimeric protein complex comprises a polypeptide that has an amino acid sequence of SEQ ID NO: 4. This sequence includes a single domain antibody (VHH) against Clec9A (i.e., 3LEC89(opt4)), a linker (i.e., 5*GGS), and a Fc hole Merchant sequence with LALA-KQ mutation (i.e., Fc hole Merchant (LALA-KQ), see Merchant et al., Nature Biotechnology 1998; 16:677-681, which is incorporated by reference in its entirety). This construct of SEQ ID NO: 4 is denoted as follows: VHH-Fc: 3LEC89 (opt4)-5*GGS-Fc hole Merchant (LALA-KQ).

In embodiments, the chimeric protein complex comprises a polypeptide that has an amino acid sequence of SEQ ID NO: 43. This sequence includes a single domain antibody (VHH) against Clec9A (i.e., R1CHCL50(opt4)), a linker (i.e., 5*GGS), and a Fc hole Merchant sequence with LALA-KQ mutation and without C terminal lysine (i.e., Fc hole Merchant (LALA-KQ), see Merchant et al., *Nature Biotechnology* 1998; 16:677-681, which is incorporated by reference in its entirety).

The chimeric protein complex of the present invention may further include an amino acid sequence having at least 95% identity with any one of SEQ ID NOs: 5-8, 29-36, or 41-42. In embodiments, the chimeric protein complex comprises a polypeptide that has an amino acid sequence of at least 98% identity with any one of SEQ ID NOs: 5-8, 29-36, or 41-42 or at least 99% identity with any one of SEQ ID Nos: 5-8, 29-36, or 41-42. In embodiments, the chimeric protein complex comprises a polypeptide that has an amino acid sequence selected from SEQ ID NOs: 5-8, 29-36, or 41-42 wherein the sequence has less than 10 mutations as compared to the selected sequence. In embodiments, the chimeric protein complex comprises a polypeptide that has an amino acid sequence selected from SEQ ID NOs: 5-8, 29-36, or 41-42 wherein the sequence has less than 5 mutations as compared to the selected sequence.

In embodiments, the chimeric protein complex comprises a polypeptide that has an amino acid sequence of SEQ ID NO: 5. This sequence includes a modified human interferon α2b having a R149A mutations (i.e., huIFNa2B_R149A), a linker (i.e., 10*GGS-G), and a Fc knob Ridgway sequence with LALA-KQ mutation (i.e., Fc knob Ridgway (LALA-KQ), see Ridgway et al., *Protein Engineering* 1996; 9:617-621, which is incorporated by reference in its entirety). This construct of sequence of SEQ ID NO: 5 is denoted as follows: Variation 1 Fc-AFN: Fc knob Ridgway (LALA-KQ)-10*GGS-G-huIFNa2B_R149A.

In embodiments, the chimeric protein complex comprises a polypeptide that has an amino acid sequence of SEQ ID NO: 6. This sequence includes a modified human interferon α2b having R149A and T106E mutations (i.e., huIFNa2B_R149A_T106E), a linker (i.e., 10*GGS-G), and a Fc knob Ridgway sequence with LALA-KQ mutation (i.e., Fc knob Ridgway (LALA-KQ), see Ridgway et al., *Protein Engineering* 1996; 9:617-621, which is incorporated by reference in its entirety). This construct of sequence of SEQ ID NO: 6 is denoted as follows: Variation 2 Fc-AFN: Fc knob Ridgway (LALA-KQ)-10*GGS-G-huIFNa2B_R149A_T106E.

In embodiments, the chimeric protein complex comprises a polypeptide that has an amino acid sequence of SEQ ID NO: 7. This sequence includes a modified human interferon α2b having a R149A mutations (i.e., huIFNa2B_R149A), a linker (i.e., 10*GGS-G), and a Fc knob Merchant sequence with LALA-KQ mutation (i.e., Fc knob Merchant (LALA-KQ), see Merchant et al., *Nature Biotechnology* 1998; 16:677-681, which is incorporated by reference in its entirety). This construct of sequence of SEQ ID NO: 7 is denoted as follows: Variation 3 Fc-AFN: Fc knob Merchant (LALA-KQ)-10*GGS-G-huIFNa2B_R149A.

In embodiments, the chimeric protein complex comprises a polypeptide that has an amino acid sequence of SEQ ID NO: 8. This sequence includes a modified human interferon α2b having R149A and T106E mutations (i.e., huIFNa2B_R149A_T106E), a linker (i.e., 10*GGS-G), and a Fc knob Merchant sequence with LALA-KQ mutation (i.e., Fc knob Merchant (LALA-KQ), see Merchant et al., *Nature Biotechnology* 1998; 16:677-681, which is incorporated by reference in its entirety). This construct of sequence of SEQ ID NO: 8 is denoted as follows: Variation 4 Fc-AFN: Fc knob Merchant (LALA-KQ)-10*GGS-G-huIFNa2B_R149A_T106E.

In embodiments, the chimeric protein complex comprises a polypeptide that has an amino acid sequence of SEQ ID NO: 41. This sequence includes a modified interferon α2b having A145G mutation, a linker (i.e., 10*GGS-G), and a Fc knob Merchant sequence with LALA-KQ mutation (i.e., Fc knob Merchant (LALA-KQ), see Merchant et al., *Nature Biotechnology* 1998; 16:677-681, which is incorporated by reference in its entirety). This construct of sequence of SEQ ID NO: 41 is denoted as follows: Fc4'-IFNa2b_A145G.

In embodiments, the chimeric protein complex comprises a polypeptide that has an amino acid sequence of SEQ ID NO: 42. This sequence includes a modified interferon α2b having T106A and A145G mutations, a linker (i.e., 10*GGS-G), and a Fc knob Merchant sequence with LALA-KQ mutation (i.e., Fc knob Merchant (LALA-KQ), see Merchant et al., *Nature Biotechnology* 1998; 16:677-681, which is incorporated by reference in its entirety). This construct of sequence of SEQ ID NO: 42 is denoted as follows: Fc4'-IFNa2a_T106E_A145G.

In one embodiment, the chimeric protein complex includes (i) an amino acid sequence having at least 95% identity with any one of SEQ ID NOs: 1 or 3 and (ii) an amino acid sequence having at least 95% identity with any one of SEQ ID NOs: 5 or 6. In another embodiment, the chimeric protein complex includes (i) an amino acid sequence having at least 98% identity with any one of SEQ ID NOs: 1 or 3 and (ii) an amino acid sequence having at least 98% identity with any one of SEQ ID NOs: 5 or 6. In another embodiment, the chimeric protein complex includes (i) an amino acid sequence having at least 99% identity with any one of SEQ ID NOs: 1 or 3 and (ii) an amino acid sequence having at least 99% identity with any one of SEQ ID NOs: 5 or 6. In an embodiment, the chimeric protein complex includes (i) an amino acid sequence having at least 95% identity with any one of SEQ ID NOs: 2 or 4 and (ii) an amino acid sequence having at least 95% identity with any one of SEQ ID NOs: 7 or 8. In an embodiment, the chimeric protein complex includes (i) an amino acid sequence having at least 98% identity with any one of SEQ ID NOs: 2 or 4 and (ii) an amino acid sequence having at least 98% identity with any one of SEQ ID NOs: 7 or 8. In another embodiment, the chimeric protein complex includes (i) an amino acid sequence having at least 99% identity with any one of SEQ ID NOs: 2 or 4 and (ii) an amino acid sequence having at least 99% identity with any one of SEQ ID NOs: 7 or 8.

In some embodiments, the chimeric protein complex comprises (i) a polypeptide having an amino acid sequence having at least 95% identity with SEQ ID NO: 2 and (ii) a polypeptide having an amino acid sequence having at least 95% identity with any one of SEQ ID NOs: 31 or 32. In some embodiments, the chimeric protein complex comprises (i) a polypeptide having an amino acid sequence having at least 98% identity with SEQ ID NO: 2 and (ii) a polypeptide having an amino acid sequence having at least 98% identity with any one of SEQ ID NOs: 31 or 32. In embodiments, the chimeric protein complex comprises (i) a polypeptide having an amino acid sequence having at least 99% identity with SEQ ID NO: 2 and (ii) a polypeptide having an amino acid sequence having at least 99% identity with any one of SEQ ID NOs: 31 or 32. In some embodiments, the chimeric protein complex comprises (i) a polypeptide having an amino acid sequence having at least 95% identity with SEQ ID NO: 43 and (ii) a polypeptide having an amino acid sequence having at least 95% identity with any one of SEQ ID NOs: 41 or 42. In some embodiments, the chimeric protein complex comprises (i) a polypeptide having an amino acid sequence having at least 98% identity with SEQ ID NO: 43 and (ii) a polypeptide having an amino acid sequence having at least 98% identity with any one of SEQ ID NOs: 41 or 42. In embodiments, the chimeric protein complex comprises (i) a polypeptide having an amino acid sequence having at least 99% identity with SEQ ID NO: 43 and (ii) a polypeptide having an amino acid sequence having at least 99% identity with any one of SEQ ID NOs: 41 or 42.

In some embodiments, the chimeric protein complex comprises: (i) a polypeptide having an amino acid sequence having at least 95% identity with any one of SEQ ID NOs: 1 or 3 and (ii) a polypeptide having an amino acid sequence having at least 95% identity with any one of SEQ ID NOs: 5 or 6.

In some embodiments, the chimeric protein complex comprises: (i) a polypeptide having an amino acid sequence having at least 98% identity with any one of SEQ ID NOs: 1 or 3 and (ii) a polypeptide having an amino acid sequence having at least 98% identity with any one of SEQ ID NOs: 5 or 6.

In some embodiments, the chimeric protein complex comprises: (i) a polypeptide having an amino acid sequence having at least 99% identity with any one of SEQ ID NOs: 1 or 3 and (ii) a polypeptide having an amino acid sequence having at least 99% identity with any one of SEQ ID NOs: 5 or 6.

In some embodiments, the chimeric protein complex comprises: (i) a polypeptide having an amino acid sequence having at least 95% identity with any one of SEQ ID NOs: 2 or 4 and (ii) a polypeptide having an amino acid sequence having at least 95% identity with any one of SEQ ID NOs: 7 or 8.

In embodiments, the chimeric protein complex comprises: (i) a polypeptide having an amino acid sequence having at least 98% identity with any one of SEQ ID NOs: 2 or 4 and (ii) a polypeptide having an amino acid sequence having at least 98% identity with any one of SEQ ID NOs: 7 or 8.

In embodiments, the chimeric protein complex comprises: (i) a polypeptide having an amino acid sequence having at least 99% identity with any one of SEQ ID NOs: 2 or 4 and (ii) a polypeptide having an amino acid sequence having at least 99% identity with any one of SEQ ID NOs: 7 or 8.

In embodiments, the chimeric protein complex comprises: (i) a polypeptide having an amino acid sequence having at least 95% identity with SEQ ID NO: 2 and (ii) a polypeptide having an amino acid sequence having at least 95% identity with any one of SEQ ID NOs: 31 or 32.

In embodiments, the chimeric protein complex comprises: (i) a polypeptide having an amino acid sequence having at least 98% identity with SEQ ID NO: 2 and (ii) a polypeptide having an amino acid sequence having at least 98% identity with any one of SEQ ID NOs: 31 or 32.

In embodiments, the chimeric protein complex comprises: (i) a polypeptide having an amino acid sequence having at least 99% identity with SEQ ID NO: 2 and (ii) a polypeptide having an amino acid sequence having at least 99% identity with any one of SEQ ID NOs: 31 or 32.

In embodiments, the chimeric protein complex comprises: (i) a polypeptide having an amino acid sequence having at least 95% identity with SEQ ID NO: 43 and (ii) a polypeptide having an amino acid sequence having at least 95% identity with any one of SEQ ID NOs: 41 or 42.

In embodiments, the chimeric protein complex comprises: (i) a polypeptide having an amino acid sequence having at least 98% identity with SEQ ID NO: 43 and (ii) a polypeptide having an amino acid sequence having at least 98% identity with any one of SEQ ID NOs: 41 or 42.

In some embodiments, the chimeric protein complex comprises: (i) a polypeptide having an amino acid sequence having at least 99% identity with SEQ ID NO: 43 and (ii) a polypeptide having an amino acid sequence having at least 99% identity with any one of SEQ ID NOs: 41 or 42.

In some embodiments, the present invention is related to a multivalent or bivalent chimeric protein complex comprising: a polypeptide having a sequence at least 95%, or 97%, or 98%, or 99% identical to the amino acid sequence of SEQ ID NO: 17 and a polypeptide having a sequence at least 95%, or 97%, or 98%, or 99% identical to the amino acid sequence of SEQ ID NO: 7; a polypeptide having a sequence at least 95%, or 97%, or 98%, or 99% identical to the amino acid sequence of SEQ ID NO: 2 and a polypeptide having a sequence at least 95%, or 97%, or 98%, or 99% identical to the amino acid sequence of SEQ ID NO: 19; a polypeptide having a sequence at least 95%, or 97%, or 98%, or 99% identical to the amino acid sequence of SEQ ID NO: 18 and a polypeptide having a sequence at least 95%, or 97%, or 98%, or 99% identical to the amino acid sequence of SEQ ID NO: 7; a polypeptide having a sequence at least 95%, or 97%, or 98%, or 99% identical to the amino acid sequence of SEQ ID NO: 20 and a polypeptide having a sequence at least 95%, or 97%, or 98%, or 99% identical to the amino acid sequence of SEQ ID NO: 7; a polypeptide having a sequence at least 95%, or 97%, or 98%, or 99% identical to the amino acid sequence of SEQ ID NO: 2 and a polypeptide having a sequence at least 95%, or 97%, or 98%, or 99% identical to the amino acid sequence of SEQ ID NO: 22; or a polypeptide having a sequence at least 95%, or 97%, or 98%, or 99% identical to the amino acid sequence of SEQ ID NO: 21 and a polypeptide having a sequence at least 95%, or 97%, or 98%, or 99% identical to the amino acid sequence of SEQ ID NO: 7. In some embodiments, the present invention is related to a method for treating or preventing a cancer, comprising administering an effective amount of the multivalent or bivalent chimeric protein complex described herein to a patient in need thereof.

In some embodiments, the present invention is related to a chimeric protein complex comprising at least two polypeptides having a sequence at least 95%, or 97%, or 98%, or 99%, or 100% identical to the amino acid sequence of any one of SEQ ID Nos: 1-36, 38, and 41-43. In embodiments, the present invention is related to a method for treating or preventing a cancer, comprising administering an effective amount of the chimeric protein complex comprising at least two polypeptides having a sequence at least 95%, or 97%, or 98%, or 99%, or 100% identical to the amino acid sequence of any one of SEQ ID Nos: 1-36, 38, and 41-43 to a patient in need thereof.

In some embodiments, the chimeric protein complex includes a modified human interferon α2. In embodiments, the modified IFN-α2 agent has reduced affinity and/or activity for the IFN-α/β receptor (IFNAR), i.e., IFNAR1 and/or IFNAR2 chains. In some embodiments, the modified IFN-α2 agent has substantially reduced or ablated affinity and/or activity for the IFN-α/β receptor (IFNAR), i.e., IFNAR1 and/or IFNAR2 chains. In some embodiments, the modified human interferon α2, as disclosed herein, has an amino acid sequence having at least 95% identity with of SEQ ID NOs: 9 or 10. In other embodiments, the modified human IFNα2 has an amino acid sequence having at least 98% identity or at least 99% identity with of SEQ ID NOs: 9 or 10. In some embodiments, the modified human IFNα2 has 1-3 mutations relative to the amino acid sequence of SEQ ID NOs: 9 or 10. In one embodiment, the modified human IFNα2 comprises a R149A mutation with respect to SEQ ID NOs: 9 or 10. In one embodiment, the modified human IFNα2 comprises a A145G mutation with respect to SEQ ID NOs: 9 or 10.

In some embodiments, the targeting moiety of the chimeric protein complex disclosed herein comprises a recombinant heavy-chain-only antibody (VHH). In some embodiments, the VHH has an amino acid sequence of at least 95% identity with of one of SEQ ID NOs: 11 or 12. In other embodiments, the VHH has an amino acid sequence of at least 98% identity with of one of SEQ ID NOs: 11 or 12 or at least 99% identity with of one of SEQ ID NOs: 11 or 12. In some embodiments, the VHH has an amino acid sequence of any one of SEQ ID NOs: 11 and 12.

Figure 7:
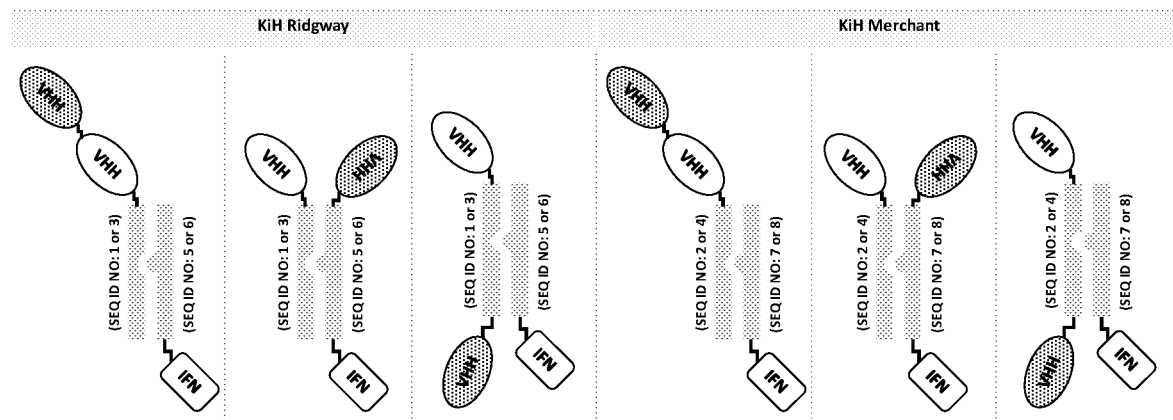
FIG. 7 shows various bivalent orientations and/or configurations that are encompassed by the present invention. The second VHH moiety to achieve bivalency is shaded and forms together with the attached linker a N- or C-terminal extension of the SEQ ID mentioned in the figure. Although SEQ ID Nos are shown, these are illustrative only, e.g. they will change if alternative mutations besides R149A, as described herein, are used. Further, the VHHs may be identical. See FIG. 1 description for clarification.

In some embodiments, the chimeric protein complex disclosed herein comprises two targeting moieties. In some embodiments, the chimeric protein complex disclosed herein comprises two identical targeting moieties. In embodiments, these bivalent modes are oriented as shown in FIG. 7.

In some embodiments, the chimeric protein complex disclosed herein comprises two targeting moieties. In some embodiments, the chimeric protein complex disclosed herein comprises two non-identical targeting moieties. In embodiments, these bivalent modes are oriented as shown in FIG. 7. For example, in some embodiments, the chimeric protein complex disclosed herein comprises targeting moieties (without limitation, VHHs) against Clec9A and PD-L1.

In embodiments, the R149A mutation is present in the IFN-α2.

In embodiments, the R149A mutation is not present in the IFN-α2 and instead, another mutation is present. For instance, this alternative mutation could be at one of positions R33, R144, A145, M148, and L153. In embodiments, the alternative mutation is one of R33A, R144A, R144I, R144L, R144S, R144T, R144Y, A145D, A145G, A145H, A145K, A145Y, M148A, and L153A. For clarity, in embodiments, any reference to R149A herein may be replaced with one of R33A, R144A, R144I, R144L, R144S, R144T, R144Y, A145D, A145G, A145H, A145K, A145Y, M148A and L153A In embodiments, any reference to R149A herein may be replaced with A145G.

In some embodiments, the chimeric protein complex disclosed herein include at least one Fc domain. In some embodiments, the chimeric protein complex includes a modified Fc domain where the modified Fc domain includes one or more of the following mutations: P329G, K322Q, K322A, or P331S relative to any one of SEQ ID NO: 13-16. In other embodiments, the modified Fc domain includes one or more of the following mutations: P329G, K322Q, K322A, or P331S relative to human IgG1 Fc.

In some embodiments, the chimeric protein complex includes a modified Fc domain that has an amino acid sequence having at least 90% identity with SEQ ID NO: 13-16. In other embodiments, the modified Fc domain has an amino acid sequence having at least 93% identity with SEQ ID NO: 13-16. In other embodiments, the modified Fc domain has an amino acid sequence having at least 95% identity with SEQ ID NO: 13-16.

In another aspect, the present invention relates to a method of treating or preventing a cancer, comprising administering an effective amount of the chimeric protein complex, as disclosed herein, to a patient in need thereof. The method can be used to treat or prevent cancers selected from one or more of basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma (e.g., Kaposi's sarcoma); skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome.

Another aspect of the present invention relates to a pharmaceutical composition comprising a chimeric protein complex, as disclosed herein, and a pharmaceutically acceptable carrier. In some embodiments, the present invention pertains to pharmaceutical compositions comprising the present chimeric protein complex.

Another aspect of the present invention relates to a method for treating or preventing a cancer, comprising administering an effective amount of the pharmaceutical composition as disclosed herein to a patient in need thereof. The pharmaceutical composition can be used for the treatment or prevention of a cancer selected from one or more of basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma (e.g., Kaposi's sarcoma); skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (e.g. that associated with brain tumors), and Meigs' syndrome.

In another aspect, the present invention relates to a recombinant nucleic acid composition encoding one or more chimeric protein complexes disclosed herein, e.g. encoding the entire chimeric protein complex or constituent polypeptides thereof. In another aspect, the present invention relates to a host cell including the recombinant nucleic acid composition complexes disclosed herein.

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50" covers the range of 45 to 55.

As used herein, the term "effective amount" refers to a quantity sufficient to achieve a desired therapeutic and/or prophylactic effect, e.g., an amount which results in the prevention of, or a decrease in a disease or disorder or one or more signs or symptoms associated with a disease or disorder. In the context of therapeutic or prophylactic applications, the amount of a composition administered to the subject will depend on the degree, type, and severity of the disease and on the characteristics of the individual, such as general health, age, sex, body weight and tolerance to drugs. The skilled artisan will be able to determine appropriate dosages depending on these and other factors. The compositions can also be administered in combination with one or more additional therapeutic compounds. In the methods described herein, the therapeutic compounds may be administered to a subject having one or more signs or symptoms of a disease or disorder. As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

The amount of compositions described herein needed for achieving a therapeutic effect may be determined empirically in accordance with conventional procedures for the particular purpose. Generally, for administering therapeutic agents for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein.

As used herein, Fc domain mutations are numbered according to EU convention (Edelman et al., *PNAS* 1969; 63 (1) 78-85, incorporated by reference in its entirety). As used herein, the term "LALA" mutation refers to a double mutant Fc domain having L234A mutation and a L235A mutation. As used herein, the term "KQ" mutation refers to a mutant Fc domain having a K322Q mutation.

Knob in hole mutants are those described in Ridgway et al., *Protein Engineering* 1996; 9:617-621, which is hereby incorporated by reference in its entirety, i.e. Y407T/T366Y.

Alternatively, knob in hole mutants are those described in Merchant et al., *Nature Biotechnology* 1998; 16:677-681, which is incorporated by reference in its entirety, i.e. S354C: T366W/Y349C:T366S:L368A:Y407V.

Unless noted, the Fc is from human IgG1.

---

SEQUENCES

SEQ ID NO: 1 Variation 1 VHH-Fc R1CHCL50(opt4)-5*GGS-Fc hole Ridgway (LALA-KQ)
DVQLVESGGGLVQPGGSLRLSCAASGSFSSINVMGWYRQAPGKERELVARITNLGLPNYADSVKGRFTISRDNSKNTV
YLQMNSLRPEDTAVYYCYLVALKAEYWGQGTLVTVSSGGSGGSGGSGGSGGSDKTHTCPPCPAPEAAGGPSVFLFPPK
PKDTLMISRTPEVTCVVVDVSHEDPEVKFNWYVDGVEVHNAKTKPREEQYNSTYRVVSVLTVLHQDWLNGKEYKCQVS
NKALPAPIEKTISKAKGQPREPQVYTLPPSRDELTKNQVSLTCLVKGFYPSDIAVEWESNGQPENNYKTTPPVLDSDG
SFFLTSKLTVDKSRWQQGNVFSCSVMHEALHNHYTQKSLSLSPGK -continued

SEQUENCES

SEQ ID NO: 2 Variation 2 VHH-Fc: R1CHCL50(opt4)-5*GGS-Fc hole Merchant
(LALA-KQ)
DVQLVESGGGLVQPGGSLRLSCAASGSFSSINVMGWYRQAPGKERELVARITNLGLPNYADSVKGRFTISRDNSKNTV
YLQMNSLRPEDTAVYYCYLVALKAEYWGQGTLVTVSSGGSGGSGGSGGSGGSDKTHTCPPCPAPEAAGGPSVFLFPPK
PKDTLMISRTPEVTCVVVDVSHEDPEVKFNWYVDGVEVHNAKTKPREEQYNSTYRVVSVLTVLHQDWLNGKEYKCQVS
NKALPAPIEKTISKAKGQPREPQVCTLPPSRDELTKNQVSLSCAVKGFYPSDIAVEWESNGQPENNYKTTPPVLDSDG
SFFLVSKLTVDKSRWQQGNVFSCSVMHEALHNHYTQKSLSLSPGK SEQ ID NO: 3 Variation 3 VHH-Fc: 3LEC90(opt4)-5*GGS-Fc hole Ridgway (LALA-KQ)
DVQLVESGGGLVQPGGSLRLSCAASGRIFSVNAMGWYRQAPGKQRELVAAITNQGAPTYADSVKGRFTISRDNSKNTV
YLQMNSLRPEDTAVYYCKAFTRGDDYWGQGTLVTVSSGGSGGSGGSGGSGGSDKTHTCPPCPAPEAAGGPSVFLFPPK
PKDTLMISRTPEVTCVVVDVSHEDPEVKFNWYVDGVEVHNAKTKPREEQYNSTYRVVSVLTVLHQDWLNGKEYKCQVS
NKALPAPIEKTISKAKGQPREPQVYTLPPSRDELTKNQVSLTCLVKGFYPSDIAVEWESNGQPENNYKTTPPVLDSDG
SFFLTSKLTVDKSRWQQGNVFSCSVMHEALHNHYTQKSLSLSPGK SEQ ID NO: 4 Variation 3 VHH-Fc: 3LEC90(opt4)-5*GGS-Fc hole Ridgway (LALA-KQ)
DVQLVESGGGLVQPGGSLRLSCAASGRIFSVNAMGWYRQAPGKQRELVAAITNQGAPTYADSVKGRFTISRDNSKNTV
YLQMNSLRPEDTAVYYCKAFTRGDDYWGQGTLVTVSSGGSGGSGGSGGSGGSDKTHTCPPCPAPEAAGGPSVFLFPPK
PKDTLMISRTPEVTCVVVDVSHEDPEVKFNWYVDGVEVHNAKTKPREEQYNSTYRVVSVLTVLHQDWLNGKEYKCQVS
NKALPAPIEKTISKAKGQPREPQVCTLPPSRDELTKNQVSLSCAVKGFYPSDIAVEWESNGQPENNYKTTPPVLDSDG
SFFLVSKLTVDKSRWQQGNVFSCSVMHELAHNHYTQKSLSLSPGK SEQ ID NO: 5 Variation 1 Fc-AFN: Fc knob Ridgway (LALA-KQ)-10*GGS-G-
huIFNa2B_R149A
DKTHTCPPCPAPEAAGGPSVFLFPPKPKDTLMISRTPEVTCVVVDVSHEDPEVKFNWYVDGVEVHNAKTKPREEQYNS
TYRVVSVLTVLHQDWLNGKEYKCQVSNKALPAPIEKTISKAKGQPREPQVYTLPPSRDELTKNQVSLYCLVKGFYPSD
IAVEWESNGQPENNYKTTPPVLDSDGSFFLYSKLTVDKSRWQQGNVFSCSVMHEALHNHYTQKSLSLSPGK**GGSGGSG
GSGGSGGSGGSGGSGGSGGSGGSGGS**GCDLPQTHSLGSRRTLMLLAQMRRISLFSCLKDRHDFGFPQEEFGNQFQKAETIP
VLHEMIQQIFNLFSTKDSSAAWDETLLDKFYTELYQQLNDLEACVIQGVGVTETPLMKEDSILAVRKYFQRITLYLKE
KKYSPCAWEVVRAEIMASFSLSTNLQESLRSKE SEQ ID NO: 6 Variation 2 Fc-AFN: Fc knob Ridgway (LALA-KQ)-10*GGS-G-
huIFNa2B_R149A_T106E
DKTHTCPPCPAPEAAGGPSVFLFPPKPKDTLMISRTPEVTCVVVDVSHEDPEVKFNWYVDGVEVHNAKTKPREEQYNS
TYRVVSVLTVLHQDWLNGKEYKCQVSNKALPAPIEKTISKAKGQPREPQVYTLPPSRDELTKNQVSLYCLVKGFYPSD
IAVEWESNGQPENNYKTTPPVLDSDGSFFLYSKLTVDKSRWQQGNVFSCSVMHEALHNHYTQKSLSLSPGK**GGSGGSG
GSGGSGGSGGSGGSGGSGGSGGSGGS**GCDLPQTHSLGSRRTLMLLAQMRRISLFSCLKDRHDFGFPQEEFGNQFQKAETIP
VLHEMIQQIFNLFSTKDSSAAWDETLLDKFYTELYQQLNDLEACVIQGVGVEETPLMKEDSILAVRKYFQRITLYLKE
KKYSPCASEVVRAEIMASFSLSTNLQESLRSKE SEQ ID NO: 7 Variation 3 Fc-AFN: Fc knob Merchant (LALA-KQ)-10*GGS-
huIFNa2B_R149A
DKTHTCPPCPAPEAAGGPSVFLFPPKPKDTLMISRTPEVTCVVVDVSHEDPEVKFNWYVDGVEVHNAKTKPREEQYNS
TYRVVSVLTVLHQDWLNGKEYKCQVSNKALPAPIEKTISKAKGQPREPQVYTLPPCRDELTKNQVSLWCLVKGFYPSD
IAVEWESNGQPENNYKTTPPVLDSDGSFFLYSKLTVDKSRWQQGNVFSCSVMHEALHNHYTQKSLSLSPGK**GGSGGSG
GSGGSGGSGGSGGSGGSGGSGGSGGS**GCDLPQTHSLGSRRTLMLLAQMRRISLFSCLKDRHDFGFPQEEFGNQFQKAETIP
VLHEMIQQIFNLFSTKDSSAAWDETLLDKFYTELYQQLNDLEACVIQGVGVTETPLMKEDSILAVRKYFQRITLYLKE
KKYSPCASEVVRAEIMASFSLSTNLQESLRSKE SEQ ID NO: 8 Variation 4 Fc-AFN: Fc knob Merchant (LALA-KQ)-10*GGS-G-
huIFNa2B_R149A_T106E
DKTHTCPPCPAPEAAGGPSVFLFPPKPKDTLMISRTPEVTCVVVDVSHEDPEVKFNWYVDGVEVHNAKTKPREEQYNS
TYRVVSVLTVLHQDWLNGKEYKCQVSNKALPAPIEKTISKAKGQPREPQVYTLPPCRDELTKNQVSLWCLVKGFYPSD
IAVEWESNGQPENNYKTTPPVLDSDGSFFLYSKLTVDKSRWQQGNVFSCSVMHEALHNHYTQKSLSLSPGK**GGSGGSG
GSGGSGGSGGSGGSGGSGGSGGSGGS**GCDLPQTHSLGSRRTLMLLAQMRRISLFSCLKDRHDFGFPQEEFGNQFQKAETIP
VLHEMIQQIFNLFSTKDSSAAWDETLLDKFYTELYQQLNDLEACVIQGVGVEETPLMKEDSILAVRKYFQRITLYLKE
KKYSPCAWEVVRAEIMASFSLSTNLQESLRSKE SEQ ID NO: 9 Human IFNα2a (amino acid sequence)
CDLPQTHSLGSRRTLMLLAWMRKISLFSCLKDRHDFGFPQEEFGNQFQKAETIPVLHEMIQQIFNLFSTKDSSAAWDE
TLLDKFYTELYQQLNDLEACVIQGVGVTETPLMKEDSILAVRKYFQRITLYLKEKKYSPCAWEVVRAEIMRSFSLSTN
LQESLRSKE SEQ ID NO: 10 Human IFNα2B (amino acid sequence)
CDLPQTHSLGSRRTLMLLAQMRRISLFSCLKDRHDFGFPQEEFGNQFQKAETIPVLHEMIQQIFNLFSTKDSSAAWDE
TLLDKFYTELYQQLNDLEACVIQGVGVTETPLMKEDSILAVRKYFQRITLYLKEKKYSPCAWEWRAEIMRSFSLSTNL
QESLRSKE SEQ ID NO: 11 R1CHCL50_opt4 (anti-human Clec9a VHH)
DVQLVESGGGLVQPGGSLRLSCAASGSFSSINVMGWYRQAPGKERELVARITNLGLPNYADSVKGRFTISRDNSKNTV
YLQMNSLRPEDTAVYYCYLVALKAEYWGQGTLVTVSS SEQ ID NO: 12 3LEC89_opt4 (anti-human Clec9a VHH)
DVQLVESGGGLVQPGGSLRLSCAASGRIFSVNAMGWYRQAPGKKQRELVAAITNQGAPTYADSVKGRFTISRDNSKNT
VYLQMNSLRPEDTAVYYCKAFTRGDDYWGQGTLVTVSS

SEQUENCES

SEQ ID NO: 13 Amino acid sequence of the Fc (human IgG1)-with LALA mutations and Ridgway hole
DKTHTCPPCPAPEAAGGPSVFLFPPKPKDTLMISRTPEVTCVVVDVSHEDPEVKFNWYVDGVEVHNAKTKPREEQYNS
TRYVVSVLTVLHQDWLNGKEYKCKVSNKALPAPIEKTISKAKGQPREPQVYTLPPSRDELTKNQVSLTCLVKGFYPSD
IAVEWESNGQPENNYKTTPPVLDSDGSFFLTSKLTVKDSRWQQGNVFSCSVMHEALHNHYTQKSLSLSPGK SEQ ID NO: 14 Amino acid sequence of the Fc (human IgG1)-with LALA mutations and Ridgway knob
DKTHTCPPCPAPEAAGGPSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDELTKNQVSLYCLVKGFYPSD
IAVEWESNGQPENNYKTTPPVLDSDGSFFLYSKLTVDKSRWQQGNVFSCSVMHEALHNHYTQKSLSLSPGK SEQ ID NO: 15 Amino acid sequence of the Fc (human IgG1)-with LALA mutations and Merchant hole
DKTHTCPPCPAPEAAGGPSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVCTLPPSRDELTKNQVSLSCAVKGFYPSD
IAVEWESNGQPENNYKTTPPVLDSDGSFFLVSKLTVDKSRWQQGNVFSCSVMHEALHNHYTQKSLSLSPGK SEQ ID NO: 16 Amino acid sequence of the Fc (human IgG1)-with LALA mutations and Merchant knob
DKTHTCPPCPAPEAAGGPSVFLFPPKPKDTLMISRPTEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPCRDELTKNQVSLWCLVKGFYPSD
IAVEWESNGQPENNYKTTPPVLDSDGSFFLYSKLTVDKSRWQQGNVFSCSVMHEALHNHYTQKSLSLSPGK Other sequences are identified elsewhere in the text.

EXAMPLES

In some Examples, two variants of the knob-in-hole technology are used: Ridgway (derived from Ridgway et al., *Protein Engineering* 1996; 9:617-621) and Merchant (derived from Merchant et al., *Nature Biotechnology* 1998; 16:677-681).

The 'standard' effector-mutation in the Ridgway constructs is LALA-PG (P329G) and this is noted herein. The 'standard' effector-mutation in the Merchant constructs is LALA-KQ (K322Q) and this is noted herein.

The terms "ActaFeron (AFN)," or "ActaKine" are occasionally used herein to reference a chimeric protein described herein (details are provided in the Examples regarding the format of the chimeric protein).

Example 1: Fc-Based AcTaferons

In order to increase the half-life of CLEC9A specific (CLEC9A is a highly specific cDC1 marker) AcTaferons human CLEC9A-VHH_huIFNa2 fusion proteins were converted into an Fc-fusion. For this purpose, the human IgG1-Fc was fused via a 20*GGS linker to the AcTaferon (VHH 3LEC89-20*GGS-huIFNa2_R149). In a second version the Fc domain was constructed in between the VHH and the IFN moiety. Effector functions of the human IgG1-Fc are reduced by introducing the LALA-P329G mutation.

The relevant sequences for expression in mammalian cells are:

P-956: pcDNA3.4-mouse light chain kappa-hIgG1-LALA-PG-*20\*GGS*-3LEC89-*20\*GGS*+G-IFNa2 R149A
(SEQ ID NO: 23)
MKLPVRLLVLMFWIPASSSDKTHTCPPCPAPEAAGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALGAPIEKTISKAKGQPREPQVYTLPP

SRDELTKNQVSLTCLVKGFYPSDIAVEWESNGQPENNYKTTPPVLDSDGSFFLYSKLTVDKSRWQQGNVFSCSVM

HEALHNHYTQKSLSLSPGK*GGSGGSGGSGGSGGSGGSGGSGGSGGSGGSGGSGGSGGSGGSGGSGGSGGSG*

*GSGGSGGS*QVQLQESGGGLVQPGGSLRLSCAASGRIFSVNAMGWYRQAPGKQRE

TISRDNAGNTVYLQMNSLRPEDTAVYYCKAFTRGDDYWGQGTQVTVSS*GGSGGSGGSGGSGGSGGSGGSGGSG*

*GSGGSGGSGGSGGSGGSGGSGGSGGSGGSGGSGGS*QDLPQTHSLGSRRTLMLLAQMRKISLFSCLKDRHDFG

FPQEEFGNQFQKAETIPVLHEMIQQIFNLFSTKDSSAAWDETLLDKFYTELYQQLNDLEACVIQGVGVTETPLMKEDSI

LAVRKYFQRITLYLKEKKYSPCAWEVVRAEIMASFSLSTNLQESLRSKE.

P-957: pcDNA3.4-mouse Ig heavy chain-3LEC89-*20\*GGS*-hIgG1-LALA-PG-*20\*GGS*+G-IFNa2 R149A
(SEQ ID NO: 24)
MGWSCIIFFLVATATGVHSQVQLQESGGGLVQPGGSLRLSCAASGRIFSVNAMGWYRQAPGKQRELVAAITNQGAP

TYADSVKGRFTISRDNAGNTVYLQMNSLRPEDTAVYYCKAFTRGDDYWGQGTQVTVSS*GGSGGSGGSGGSGGSG*

*GSGGSGGSGGSGGSGGSGGSGGSGGSGGSGGSGGSGGSGGS*DKTHTCPPCPAPEAAGGPSVFLFPPKPK

DTLMISRTPEVTCVVVDVSHEDPEVKFNWYVDGVEVHNAKTKPREEQYNSTYRVVSVLTVLHQDWLNGKEYKCKV

-continued

SNKALGAPIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK*GGSGGSGGSGGSGGSGGSGGSGGSG*

*GSGGSGGSGGSGGSGGSGGSGGSGGSGGSGGSGGSGGSG*CDLPQTHSLGSRRTLMLLAQMRKISLESCLKDRHDFG

FPQEEFGNQFQKAETIPVLHEMIQQIFNLFSTKDSSAAWDETLLDKFYTELYQQLNDLEACVIQGVGVTETPLMKEDSI

LAVRKYFQRITLYLKEKKYSPCAWEWVRAEIMASESLSTNLQESLRSKE.

The constructs were made by GeneArt (Thermo Fisher) and transiently expressed in the ExpiCHO expression system (Thermo Fisher) according to the manufacturer's guidelines. Ten days after transfection, supernatant was collected and cells removed by centrifugation. Recombinant proteins were purified from the medium using the rProtein A Sepharose Fast Flow resin (GE Healthcare) according to the manufacturer's guidelines. Unexpectedly the proteins although expressed at 70-170 mg/L showed severe solubility problems and even at concentrations below 1 mg/ml they tended to aggregate and precipitate when stored at 4° C. or after a single freeze-thaw cycle. When the VHH 3LEC89 was replaced by the unrelated VHH 2LIG99 specific for human PD-L1 similar observations were made indicating that an Fc-based AcTakine format has manufacturability liabilities.

Surprisingly the solubility problem was solved by designing a different type of Fc-construct. In this new format a heterodimeric Fc complex is generated by combining a VHH-Fc fusion with a Fc-IFN fusion using either the knob into hole mutations Y407T/T366Y or S354C:T366W/Y349C:T366S:L368A:Y407V. Additional variants include an optional knock-out of the O-glycosylation site in the huIFNa2 by the T106E mutation. In total 8 constructs were designed based on 2 different humanized human CLEC9A specific VHH. To reduce effector functions of the IgG1-Fc protein the mutation LALA-K322Q was used. The sequences of the mature proteins are represented by SEQ ID NO: 1-8. This result in total in 8 different Fc-complexes that can be generated by combining knob and hole constructs as shown in FIG. 1.

For expression in mammalian cells the sequences are linked to a leader sequence and constructs were made by GeneArt (Thermo Fisher). Production was performed in ExpiCHO cells as described above. Recombinant proteins were purified from the supernatant on a HiTrap Protein A HP (GE Healthcare) and eluted proteins were, after neutralization, desalted on a G25 column (GE Healthcare) followed by final and 0.22 μm filtration. Proteins showed to remain soluble at 4° C. or after repeated freeze/thaw cycles at concentrations of at least 10 mg/mL.

Example 2: PK Effects of Chimera with or without Fc

PK (Pharmacokinetics) Study in Mouse with the 4 Different Variants of the R1CHCL50 Based Fc-Proteins.

Figure 2:
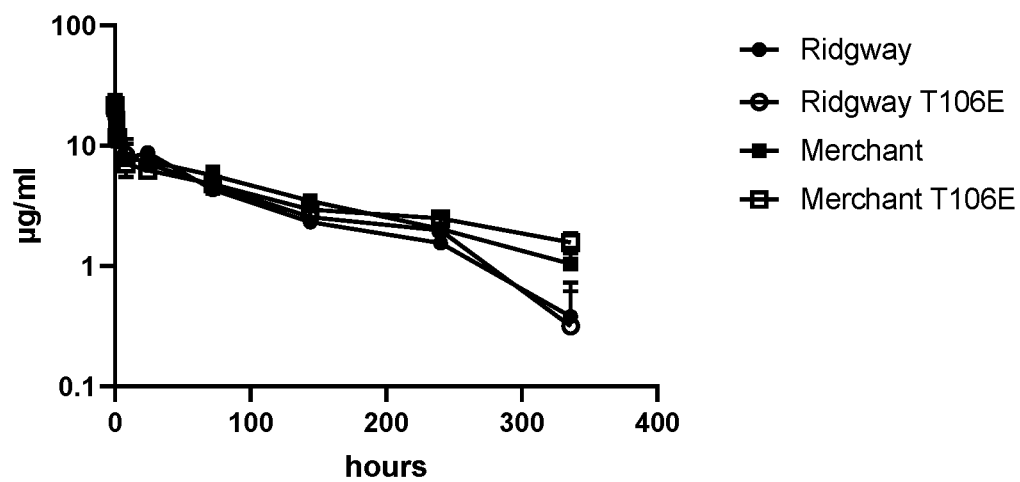
FIG. 2 shows plasma concentrations of Fc-AFNs after intravenous administration in mouse. Average values of 3 individual samples per time point time (+SEM) are plotted.

In total 9 mice were dosed intravenously at 1 mg/kg with each construct. K-EDTA blood was taken from a first group of 3 mice at 5 minutes, 8 hours and 6 days, from a second group of 3 mice at 15 minutes, 1 day and 10 days and from a third group of 3 mice at 2 hours, 3 days and 14 days. The concentration of intact CLEC9A-AFN Fc-construct was measured by ELISA. In brief the MAXISORP Nunc Immune plates (Thermo Scientific) were coated overnight with anti-human interferon alpha mAb (clone MMHA-13; PBL Assay Science) at 0.5 μg/ml in PBS. After washing the plates four times with PBS+0.05% Tween-20, they were blocked with 0.1% Casein in PBS for at least 1 hour at room temperature. Subsequently, diluted samples and standards were incubated in 0.1% Casein in PBS for 2 hours at room temperature. After another wash cycle a custom made rabbit-anti-VHH (diluted 1/20000 in 0.1% Casein in PBS) was incubated for 2 hours at room temperature followed by an additional wash cycle and incubation with HRP-conjugated goat anti-rabbit (Jackson—111-035-144; 1:5000 in 0.1% Casein) for 1 hour at room temperature. After a final washing cycle, peroxidase activity was measured using KPL substrate (5120-0047; SeraCare) according to the manufacturer's instructions. Concentrations from samples were calculated using GraphPad Prism. Measured concentrations are plotted in FIG. 2 and show that all 4 constructs have a similar PK profile except for a somewhat faster clearance of the Ridgway based Fc-construct at the last sampling time point. Terminal half-life was estimated on average at about 3 days for the Ridgway constructs and 4.5 days for the Merchant constructs.

PK study in mouse with a CLEC9A AcTaferon without Fc-fusion.

In a separate study the PK of an AFN without Fc (3LEC89-20*GGS-huIFNa2_R149A-his6) in mice was evaluated. This chimera has the sequence of:

P-602 sequence
(SEQ ID NO: 25)
QVQLQESGGGLVQPGGSLRLSCAASGRIFSVNAMGWYRQAPGKQRELVAA

ITNQGAPTYADSVKGRFTISRDNAGNTVYLQMNSLRPEDTGAVYYCKAFT

RGDDYWGQGTQVTVSSVDGGSGGSGGSGGSGGSGGSRSGGSGGSGGSGGS

GGSGGSGGSGGSGGSGGSGGSGGSGGSAAAMCDLPQTHSLGSRRTLMLLA

QMRRISLFSCLKDRDHFGFPQEEFGNQFQKAETIPVLHEMIQQIFNLFST

KDSSAAWDETLLDKFYTELYQQLNDLEACVIQGVGVTETPLMKEDSILAV

RKYFQRITLYLKEKKYSPCAWEVVRAEIMASFSLSTNLQESLRSKELEHH

HHHH.

Nine animals were dosed intravenously at 3 mg/kg. K-EDTA blood was taken from a first group of 3 mice at 5 minutes and 1 hour, from a second group of 3 mice at 15 minutes and 3 hours and finally from the last group at 8 hours. The concentration in the plasma samples was measured using the same ELISA as described for the Fc-fusion proteins.

Figure 3:
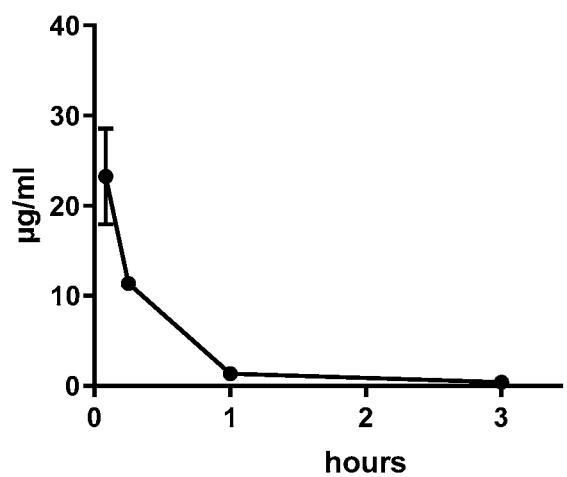
FIG. 3 shows the plasma concentrations of a CLEC9A AFN (construct lacking Fc) after intravenous administration in mouse. Average values of 3 individual samples per time point time (+SEM) are plotted.
Figure 4A:
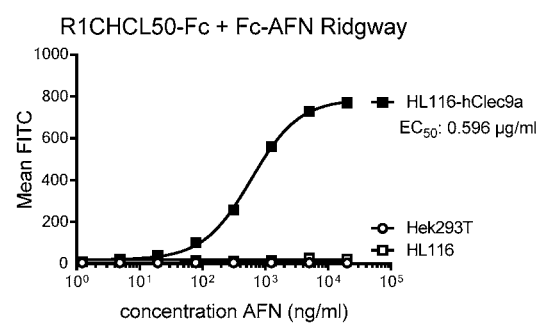
FIG. 4A-D show specific binding of CLEC9A-AFN Fc-construct to cells expressing human CLEC9A (HL116-hCLEC9a) compared to control cells (HL116 and HEK293T).
Figure 4B:
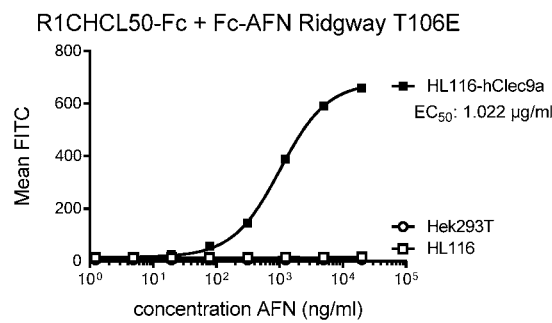
Figure 4C:
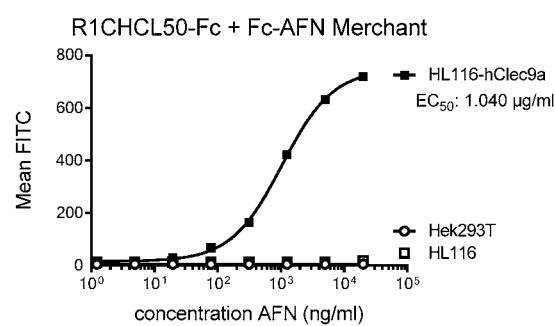
Figure 4D:
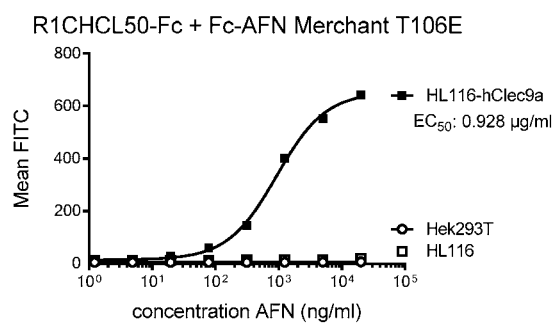

The measured concentration (FIG. 3) show a fast clearing of this type of molecules resulting in a concentration below detection limit (0.12 μg/ml) at the 8-hour time point. The estimated terminal half-life is in the range of only 2 hours, clearly demonstrating the superior half-life properties of the Fc-based AcTakines.

Example 3: Binding and In Vivo Effects of Constructs

To measure relative binding affinities the same 4 molecules as shown in Example 2 were incubated with a serial dilution of CLEC9A-AFN Fc-construct on HL116-hClec9A cells. To asses binding specificity also parental HL116 cells and parental HEK293T cells (both lacking detectable expression of Clec9A) were incubated with an identical serial dilution of the CLEC9A-AFN Fc-construct. Binding was detected by subsequent incubation with an FITC-coupled anti-human secondary Ab, measured on a MACSQuant X instrument (Miltenyi Biotech) and analyzed using the FlowLogic software (Miltenyi Biotech). Data in FIG. 4 illustrates that the Fc-based AFNs have similar binding EC50s for HL116-hClec9A cells while no binding was detected on the cell lines not expressing Clec9A.

Figure 5:
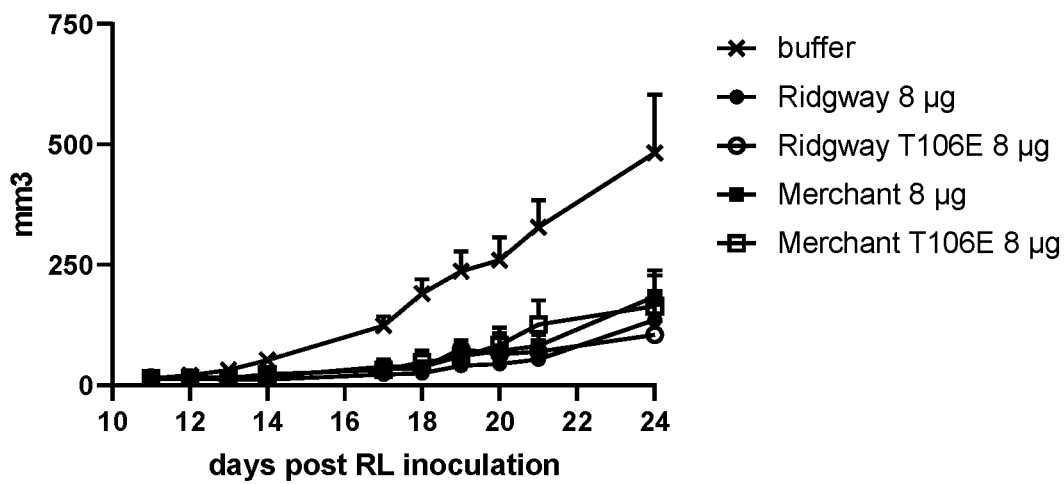
FIG. 5 shows tumor growth curves in humanized mice after treatment with buffer or four different CLEC9A-AFN Fc-constructs. Average values (in mm³) of 5 animals per time point time (+SEM) are plotted.
Figure 6:
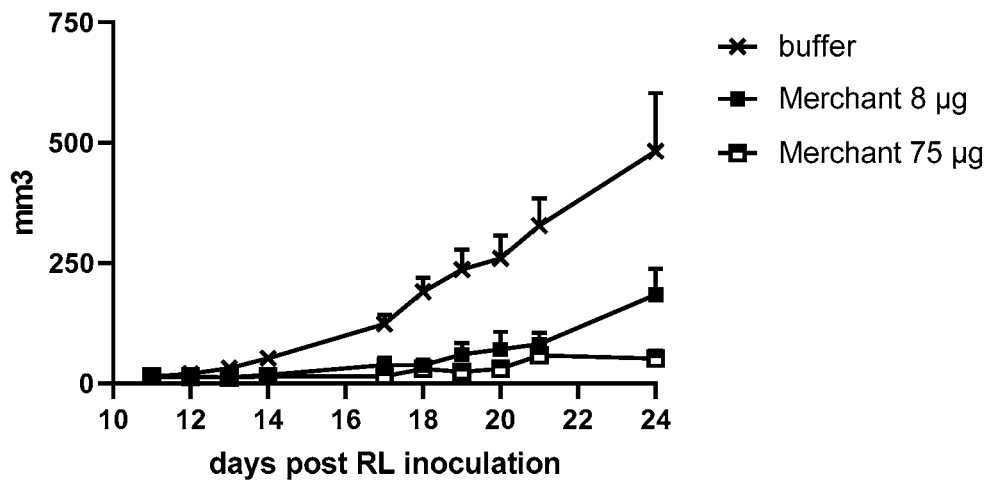
FIG. 6 shows tumor growth curves in humanized mice after treatment with buffer or increasing doses of a single CLEC9A-AFN Fc-construct. Average values (in mm³) of 5 animals per time point time (+SEM) are plotted.

To evaluate the efficacy of the Fc-based AFNs the molecules were tested in a tumor model in a humanized mouse. In brief, newborn NSG mice (1-2 days of age) were sublethal irradiated with 100 cGy prior to intrahepatic delivery of $1 \times 10^5$ CD34+ human stem cells (from HLA-A2 positive cord bloods). At week 13 after stem cell transfer mice were subcutaneously inoculated with $25 \times 10^5$ human RL follicular lymphoma cells (ATCC CRL-2261; not sensitive to the direct anti-proliferative effect of IFN). Mice were treated daily intraperitoneally with 30 μg of human Flt3L protein, from day 10 to day 19 after tumor inoculation. Weekly intravenous injection with buffer or Fc-AFN (8 or 75 μg) was initiated at day 11 after tumor inoculation, when a palpable tumor was visible (n=5 mice per group). Tumor size (caliper measurements), body weight and temperature were assessed daily. Data in FIG. 5 and FIG. 6 show the tumor growth until 6 days after the second treatment. FIG. 5 demonstrates that all constructs induced a similar level of tumor growth inhibition at the lower dose of 8 μg. FIG. 6 shows the result of higher doses for a Merchant construct resulting in increasing tumor growth inhibition. Data on body weight and temperature did not show any major difference between buffer treatment and AFN treatment supporting that all AFN treatments were well tolerated.

Example 4: Bivalent and Bispecific Variants

In order to further increase the targeting capacity of the molecules, additional VHH moieties are added resulting in constructs of which non-limiting examples of configurations are shown in FIG. 7. These novel constructs target CLEC9A in a bivalent mode or co-target e.g. both CLEC9A and PD-L1. By way of example constructs below are based on the R1CHCL50(opt4) VHH directed against CLEC9A and/or the 2LIG99 VHH directed against PD-L1 and the huIFNa2B_R149A. By replacing R1CHCL50(opt4) with 3LEC89(opt4) a similar series can be generated. Alternatively the huIFNa2B_R149A can be replaced with huIFNa2B_R149A_T106E. Finally examples below are based on Fc moieties containing Merchant based knob-into-hole mutations which can be exchanged for Fc moieties with Ridgway based knob-into-hole mutations.

Novel constructs

A. Hole chain for bivalent CLEC9A targeting by additional VHH at N-terminus of Fc (Merchant)

VHH-VHH-Fc: R1CHCL50(opt4)-5*GGS-R1CHCL50(opt4)-5*GGS-Fc (LALA-KQ)
(SEQ ID NO: 17)
DVQLVESGGGLVQPGGSLRLSCAASGSFSSINVMGWYRQAPGKERELVAR

ITNLGLPNYADSVKGRFTISRDNSKNTVYLQMNSLRPEDTAVYYVYLVAL

KAEYWGQGTLVTVSSGGSGGSGGSGGSGGSDVQLVESGGGLVQPGGSLRL

SCAASGSFSSINVMGWYRQAPGKERELVARITNLGLPNYADSVKGRFTIS

RDNSKNTVYLQMNSLRPEDTAVYYCYLVALKAEYWGQGTLVTVSSGGSGG

SGGSGGSGGSDKTHTCPPCPAPEAAGGPSVFLFPPPKPKDTLMISRTPEVT

CVVVDVSHEDPEVKFNWYVDGVEVHNAKTKPREEQYNSTYRVVSVLTVLH

QDWLNGKEYKCQVSNKALPAPIEKTISKAKGQPREPQVCTLPPSRDELTK

NQVSLSCAVKGFYPSDIAVEWESNGQPENNYKTTPPVLDSDGSFFLVSKL

TVDKSRWQQGNVFSCSVHEALHNHYTQKSLSLSPGK

B. Hole chain for bivalent CLEC9A targeting by additional VHH on C-terminus of Fc (Merchant)

VHH-Fc-VHH: R1CHCL50(opt4)-5*GGS-Fc (LALA-KQ)-R1CHCL50(opt4)
(SEQ ID NO: 18)
DVQLVESGGGLVQPGGSLRLSCAASGSFSSINVMGWYRQAPGKERELVAR

ITNLGLPNYADSVKGRFTISRDNSKNTVYLQMNSLRPEDTAVYYCYLVAL

KAEYWGQGTLVTVSSGGSGGSGGSGGSGGSDKTHTCPPCPAPEAAGGPSV

FLFPPPKPKDTLMISRTPEVTCVVVDVSHEDPEVKFNWYVDGVEVHNAKTK

PREEQYNSTYRVVSVLTVLHQDWLNGKEYKCQVSNKALPAPIEKTISKAK

GQPREPQVCTLPPSRDELTKNQVSLSCAVKGFYPSDIAVEWESNGQPENN

YKTTPPVLDSDGSFFLVSKLTVDKSRWQQGNVFSCSVMHEALHNHYTQKS

LSLSPGKGGSGGSGGSGGSGGSDVQLVESGGGLVQPGGSLRLSCAASGSF

SSINVMGWYRQAPGKERELVARITNLGLPNYADSVKGRFTISRDNSKNTV

YLQMNSLRPEDTAVYYCYLVALKAEYWGQGTLVTVSS

C. Knob chain for bivalent CLEC9A targeting by additional VHH on N-terminus of Fc (Merchant)

VHH-Fc-AFN: R1CHCL50(opt4)-5*GGS-Fc(LALA-KQ)-10*GGS-G-huIFNa2B_R149A
(SEQ ID NO: 19)
DVQLVESGGGLVQPGGSLRLSCAASGSFSSINVMGWYRQAPGKERELVAR

ITNLGLPNYADSVKGRFTISRDNSKNTVYLQMNSLRPEDTAVYYCYLVAL

KAEYWGQGTLVTVSSGGSGGSGGSGGSGGSDKTHTCPPCPAPEAAGGPSV

FLFPPPKPKDTLMISRTPEVTCVVVDVSHEDPEVKFNWYVDGVEVHNAKTK

PREEQYNSTYRVVSVLTVLHQDWLNGKEYKCQVSNKALPAPIEKTISKAK

GQPREPQVYTLPPCRDELTKNQVSLWCLVKGFYPSDIAVEWESNGQPENN

YKTTPPVLDSDGSFFLYSKLTVDKSRWQQGNVFSCSVMHEALHNHYTQKS

LSLSPGKGGSGGSGGSGGSGGSGGSGGSGGSGGSGGSGCDLPQTHSLGSRRTL

MLLAQMRRISLFSCLKDRHDFGFPQEEFGNQFQKAETIPVLHEMIQQIFN

LFSTKDSSAAWDETLLDKFYTELQQLNDLEACVIQGVGVTETPLMKEDSI

LAVRKYFQRITLYLEKKYSPCAWEVVRAEIMASFSLSTNLQESLRSKE

D. Hole chain for bispecific CLEC9A-PDL1 targeting by additional VHH at N-terminus of Fc (Merchant)

VHH-VHH-Fc: 2LIG99-5*GGS-R1CHCL50(opt4)-5*GGS-Fc (LALA-KQ)
(SEQ ID NO: 20)
QVQLQESGGGLVQAGGSLRLSCTASGTIFSINRMDWFRQAPGKQRELVAL

ITSDGTPAYADSAKGRFTISRDNTKKTVSLQMNSLKPEDTAVYYCHVSSG

-continued

VYNYWGQGTQVTVSSGGSGGSGGSGGSGGSDVQLVESGGGLVQPGGSLRL

SCAASGSFSSINVMGWYRQAPGKERELVARITNLGLPNYADSVKGRFTIS

RDNSKNTVYLQMNSLRPEDTAVYYCYLVALKAEYWGQGTLVTVSSGGSGG

SGGSGGSGGSDKTHTCPPCPAPEAAGGPSVFLFPPKPKDTLMISRTPEVT

CVVVDVSHEDPEVKFNWYVDGVEVHNAKTKPREEQYNSTYRVVSVLTVLH

QDWLNGKEYKCQVSNKALPAPIEKTISKAKGQPREPQVCTLPPSRDELTK

NQVSLSCAVKGFYPSDIAVEWESNGQPENNYKTTPPVLDSGSFFLVSKLT

VDKSRWQQGNVFSCSVMHEALHNHYTQKSLSLSPGK

E. Hole chain for bispecific CLEC9A-PD-L1
targeting by additional VHH on C-terminus of Fc
(Merchant)

VHH-Fc-VHH: R1CHCL5-(opt4)-5*GGS-Fc (LALA-KQ)-
5*GGS-2LIG99
(SEQ ID NO: 21)
DVQLVESGGGLVQPGGSLRLSCAASGSFSSINVMGWYRQAPGKERELVAR

ITNLGLPNYADSVKGRFTISRDNSKNTVYLQMNSLRPEDTAVYYCYLVAL

KAEYWGQGTLVTVSSGGSGGSGGSGGSGGSDKTHTCPPCPAPEAAGGPSV

FLFPPKPKDTLMISRTPEVTCVVVDVSHEDPEVKFNWYVDGVEVHNAKTK

PREEQYNSTYRVVSVLTVLHQDWLNGKEYKCQVSNKALPAPIEKTISKAK

GQPREPQVCTLPPSRDELTKNQVSLSCAVKGFYPSIDAVEWESNGQPENN

YKTTPPVLDSDGSFFLVSKLTVDKSRWQQGNVFSCSVMHEALHNHYTQKS

LSLSPGKGGSGGSGGSGGSGGSQVQLQESGGGLVQAGGSLRLSCTASGTI

FSINRMDWFRQAPGKQRELVALITSDGTPAYADSAKGRFTISRDNTKKTV

SLQMNSLKPEDTAVYYCYVSSGVYNYWGQGTQVTVSS

F. Knob chain for bispecific CLEC9A-PD-L1
targeting by additional VHH on N-terminus of Fc
(Merchant)

VHH-Fc-AFN: 2LIG99-5*GGS-Fc(LALA-KQ)-10*GGS-G-
huIFNa2B_R149A
(SEQ ID NO: 22)
QVQLQESGGGLVQAGGSLRLSCTASGTIFSINRMDWFRQAPGKQRELVAL

ITSDGTPAYADSAKGRFTISRDNTKKTVSLQMNSLKPEDTAVYYCHVSSG

VYNYWGQGTQVTVSSGGSGGSGGSGGSGGSDKTHTCPPCPAPEAAGGPSV

FLFPPKPKDTLMISRTPEVTCVVVDVSHEDPEVKFNWYVDGVEVHNAKTK

PREEQYNSTYRVVSVLTVLHQDWLNGKEYKCQVSNKALPAPIEKTISKAK

GQPREPQVYTLPPCRDELTKNQVSLWCLVKGFYPSDIAVEWESNGQPENN

YKTTPPVLDSDGSFFLYSKLTVDKSRWQQGNVFSCSCMHEALHNHYTQKS

LSLSPGKGGSGGSGGSGGSGGSGGSGGSGGSGGSGGSCDLPQTHSLGSR

RTLMLLAQMRRISLFSCLKDRHDFGFPQEEFGNQFQKAETIPVLHEMIQQ

IFNLFSTKDSSAAWDETLLDKFYTELYQQLNDLEACVIQGVGVTETPLMK

EDSILAVRKYFQRITLYLKEKKYSPCASEVVRAEIMASFSLSTNLQESLR

SKE

For expression in mammalian cells the sequences are linked to a leader sequence and expression constructs were made by GeneArt (Thermo Fisher). Production is performed in ExpiCHO cells as described above. Recombinant proteins are purified from the supernatant on a HiTrap Protein A HP (GE Healthcare) and eluted proteins are, after neutralization, desalted on a G25 column (GE Healthcare) followed by final and 0.22 μm filtration. More specifically the following expressions constructs are combined to generate the Fc-based AcTaferons Construct containing SEQ ID NO: 17+construct containing SEQ ID NO: 7

Construct containing SEQ ID NO: 2+construct containing SEQ ID NO: 19

Construct containing SEQ ID NO: 18+construct containing SEQ ID NO: 7

Construct containing SEQ ID NO: 20+construct containing SEQ ID NO: 7

Construct containing SEQ ID NO: 2+construct containing SEQ ID NO: 22

Construct containing SEQ ID NO: 21+construct containing SEQ ID NO: 7

Example 5: A145G and M148A AFN Mutations

In this example, the potential of the IFN variations A145G and M148A as AFN mutation (i.e. the warhead mutation that results in a loss in biological activity, which can be restored upon targeting of the warhead) was evaluated.

Mutations were evaluated in the heterodimeric, 'knob-in-hole' Fc AFN context. Here, the Clec9A VHH R1CHCL50 sequence was, via the flexible 20*GGS-linker and in the pcDNA3.4 expression vector, fused to the human IgG1 Fc sequence containing the L234A_L235A_K322Q effector mutations and the 'hole' modifications Y349C_T366S_L368A_Y407V (see sequence R1CHCL50-Fc3 below). Second AFN partner, also cloned in the pcDNA3.4 vector, consisted of the fusion between the human IgG1 Fc sequence containing the L234A_L235A_K322Q effector mutations and the 'knob' modifications S354C_T366W and the hIFNa2 sequence with the AFN mutation A145G or M148A and the O-glycosylation mutation T106E (see sequences below).

To produce these 'knob-in-hole' Fc AFNs, a combination of both 'hole' and 'knob' plasmids was transfected in ExpiCHO™ cells (ThermoFisher) according to the manufacturer's instructions. Seven days post transfection, recombinant proteins were purified using protein A spin plates (ThermoFisher), quantified and purity tested using SDS-PAGE.

Figure 8A:
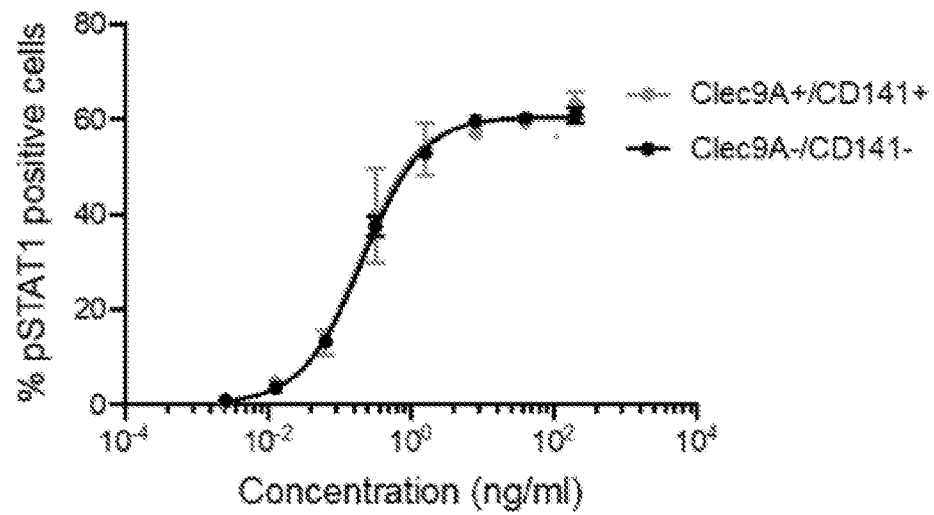
FIG. 8A shows results of pSTAT1 phosphorylation in Clec9A−/CD141− and Clec9A+/CD141+ PBMC's by IFNα2.
Figure 8B:
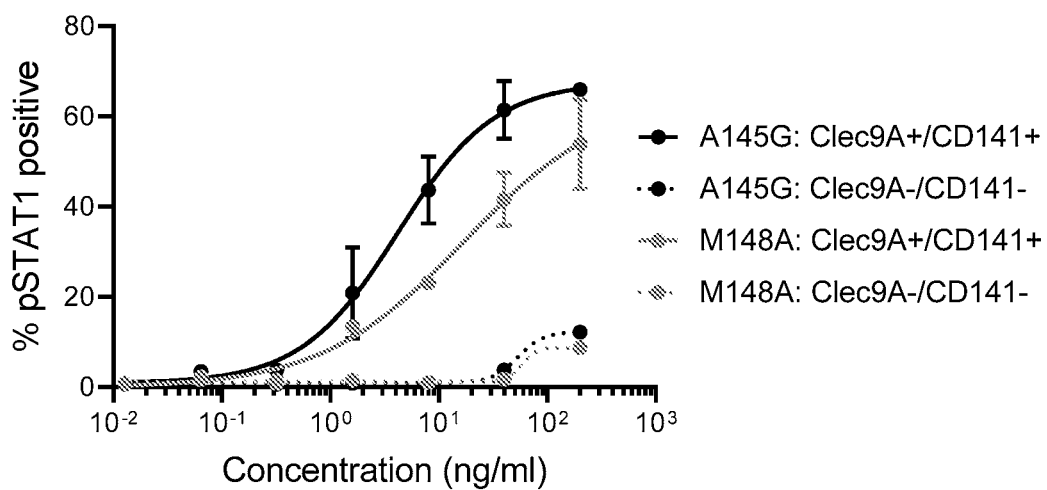
FIG. 8B shows results of pSTAT1 phosphorylation in Clec9A−/CD141− and Clec9A+/CD141+ PBMC's by AFNs with the A145G or M148A mutations.

Resulting A145G and M148 AFN's were tested for STAT1 phosphorylation in primary cDC1 cells (expressing Clec9A, the target of the AFN's) compared to other PBMC populations. In brief, PBMCs from buffy coats of healthy donors were isolated using density gradient centrifugation using Lymphoprep™ (StemCell technologies). Cells were washed twice with FACS buffer (2% FBS, 1 mM EDTA in PBS) and stained with anti-Clec9A and anti-CD141 Abs (both Miltenyi) to identify the cDC1 population for 20 minutes at 4° C. After two washes, cells were stimulated with a serial dilution wild type IFNa2 or both AFN's for 15 minutes at 37° C. After fixation (10 minutes, 37° C., Fix Buffer I; BD Biosciences), permeabilization (30 minutes, on ice, Perm Ill Buffer I; BD Biosciences) and washing, cells were stained with anti-STAT1 pY701 Ab (BD Biosciences). Samples were acquired with a MACSQuant® X instrument (Miltenyi Biotec) and analyzed using the FlowLogic™ software (Miltenyi Biotec). Data in FIG. 8A-B clearly illustrate that (i) Clec9A−/CD141− and Clec9A+/CD141+ cells are comparable sensitive to wild type IFNa2, and that (ii) both A145G and M148A mutations abolishes most of the signaling in non-cDC1 PBMC's (Clec9A−/CD141−) but that targeting to Clec9A positive cells (Clec9A+/CD141+) to a great extent restores this signaling. This results in an AFN effect of at least 100-fold for both the A145G or M148A mutations and illustrates the potential of these mutations for the design of AFNs.

Sequences:

```
P-1451: R1CHCL50-20*GGS-hIgG1 Fc_L234A_L235A_K322Q_Y349C_T366S_L368A_Y407V
(short: R1CHCL50-Fc3)
                                                              (SEQ ID NO: 26)
QVQLQESGGGLVHPGGSLRLSCAASGSFSSINVMGWYRQAPGKERELVARITNLGLPNYADSVTGRETISRDN

AKNTVYLQMNSLKPEDTAVYYCYLVALKAEYWGQGTQVTVSSGGSGGSGGSGGSGGSGGSGGSGGSGGSGGSG

GSGGSGGSGGSGGSGGSGGSGGSGGSGGSGGSDKTHTCPPCPAPEAAGGPSVFLFPPKPKDTLMISRTPEV

TCVVVDVSHEDPEVKFNWYVDGVEVHNAKTKPREEQYNSTYRVVSVLTVLHQDWLNGKEYKCQVSNKALPAPI

EKTISKAKGQPREPQVCTLPPSRDELTKNQVSLSCAVKGFYPSDIAVEWESNGQPENNYKTTPPVLDSDGSFFL

VSKLTVDKSRWQQGNVFSCSVMHEALHNHYTQKSLSLSPGK
```

```
P-1846: hIgG1 Fc_L234A_L235A_K322Q_S354C_T366W-20*GGS-hIFNa2_T106E_A145G
(short: Fc4-hIFNa2_A145G)
                                                              (SEQ ID NO: 27)
DKTHTCPPCPAPEAAGGPSVFLFPPKPKDTLMISRTPEVTCVVVDVSHEDPEVKFNWYVDGVEVHNAKTKPREE

QYNSTYRVVSVLTVLHQDWLNGKEYKCQVSNKALPAPIEKTISKAKGQPREPQVYTLPPCRDELTKNQVSLWCL

VKGFYPSDIAVEWESNGQPENNYKTTPPVLDSDGSFFLYSKLTVDKSRWQQGNVFSCSVMHEALHNHYTQKSL

SLSPGKGGSGGSGGSGGSGGSGGSGGSGGSGGSGGSGGSGGSGGSGGSGGSGGSGGSGGSGGSGGSC

DLPQTHSLGSRRTLMLLAQMRKISLFSCLKDRHDFGFPQEEFGNQFQKAETIPVLHEMIQQIFNLFSTKDSSAAW

DETLLDKFYTELYQQLNDLEACVIQGVGVEETPLMKEDSILAVRKYFORITLYLKEKKYSPCAWEVVRGEIMRSES

LSTNLQESLRSKE
```

```
P-1850: hIgG1 Fc_L234A_L235A_K322Q_S354C_T366W-20*GGS-hIFNa2_T106E_M148A
(short: Fc4-hIFNa2_M148A)
                                                              (SEQ ID NO: 28)
DKTHTCPPCPAPEAAGGPSVFLFPPKPKDTLMISRTPEVTCVVVDVSHEDPEVKFNWYVDGVEVHNAKTKPREE

QYNSTYRVVSVLTVLHQDWLNGKEYKCQVSNKALPAPIEKTISKAKGQPREPQVYTLPPCRDELTKNQVSLWCL

VKGFYPSDIAVEWESNGQPENNYKTTPPVLDSDGSFFLYSKLTVDKSRWQQGNVFSCSVMHEALHNHYTQKSL

SLSPGKGGSGGSGGSGGSGGSGGSGGSGGSGGSGGSGGSGGSGGSGGSGGSGGSGGSGGSGGSGGSC

DLPQTHSLGSRRTLMLLAQMRKISLFSCLKDRHDFGFPQEEFGNQFQKAETIPVLHEMIQQIFNLFSTKDSSAAW

DETLLDKFYTELYQQLNDLEACVIQGVGVEETPLMKEDSILAVRKYFQRITLYLKEKKYSPCAWEVVRAEIARSFS

LSTNLQESLRSKE
```

Example 6: A145G and M148A AFN Mutations In Vivo

Figure 9:
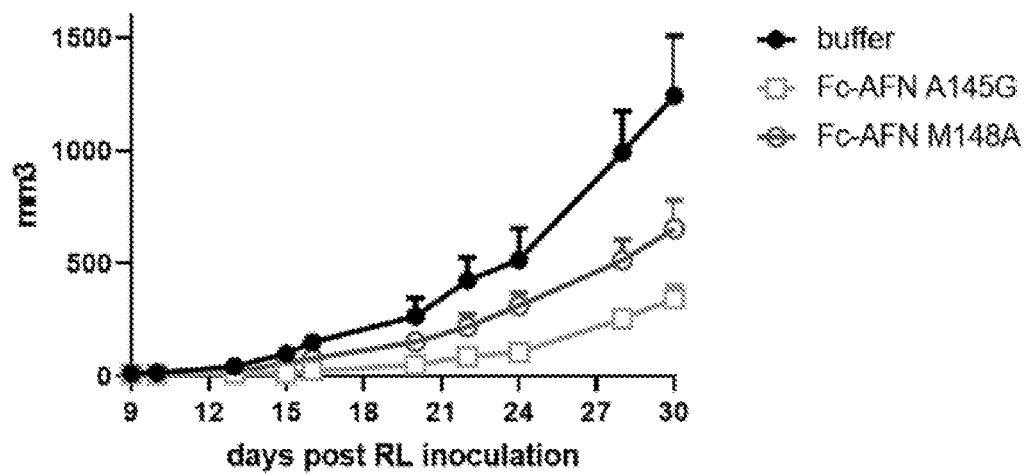
FIG. 9 shows tumor growth curves in humanized mice after treatment with buffer or a 7.5 μg dose of two different CLEC9A-AFN Fc-constructs. Average values (+SEM) of tumor sizes (in mm³) of 6 animals per time point time were plotted.

To evaluate the efficacy of the Fc-based AFNs the molecules were tested in a tumor model in a humanized mouse. In brief, new-born NSG mice (1-2 days of age) were sublethally irradiated with 100 cGy prior to intrahepatic delivery of $1 \times 10^5$ CD34+ human stem cells (from HLA-A2 positive cord bloods). At week 13 after stem cell transfer mice were subcutaneously inoculated with $25 \times 10^5$ human RL follicular lymphoma cells (ATCC CRL-2261; not sensitive to the direct anti-proliferative effect of IFN). Mice were treated intraperitoneally with 30 μg of human Flt3L protein, from day 9 to day 22 after tumor inoculation. Weekly intravenous injection with buffer or Fc-AFN (7.5 μg) constructs as described in example 5 was initiated at day 9 after tumor inoculation, when a palpable tumor was visible (n=6 mice per group). Tumor size (caliper measurements), body weight and temperature were assessed daily. Data in FIG. 9 show the tumor growth until one week after the third treatment and demonstrate that both constructs induced a strong level of tumor growth inhibition. Data on body weight and temperature did not show any major difference between buffer treatment and AFN treatment supporting that all AFN treatments were well tolerated.

Example 7: Additional Fc-AFN Constructs Based on A145G and M148A Mutations

The following additional Fc constructs with attenuated human interferon alpha2 were generated:

```
A. hIgG1 Fc_L234A_L235A_K322Q_S354C_T366W-10*GGS-G-hIFNa2_T106E_M148A
                                                              (SEQ ID NO: 29)
DKTHTCPPCPAPEAAGGPSVFLFPPKPKDTLMISRTPEVTCVVVDVSHEDPEVKFNWYVDGVEVHNAKTKPREE

QYNSTYRVVSVLTVLHQDWLNGKEYKCQVSNKALPAPIEKTISKAKGQPREPQVYTLPPCRDELTKNQVSLWCL

VKGFYPSDIAVEWESNGQPENNYKTTPPVLDSDGSFFLYSKLTVDKSRWQQGNVFSCSVMHEALHNHYTQKSL
```

-continued

SLSPGKGGSGGSGGSGGSGGSGGSGGSGGSGGSGGSGCDLPQTHSLGSRRTLMLLAQMRKISLFSCLKDRH

DFGFPQEEFGNQFQKAETIPVLHEMIQQIFNLFSTKDSSAAWDETLLDKFYTELYQQLNDLEACVIQGVGVEETP

LMKEDSILAVRKYFQRITLYLKEKKYSPCAWEVVRAE▓RSFSLSTNLQESLRSKE

B. hIgG1 Fc_L234A_L235A_K322Q_S354C_T366W-**10*GGS-G**-hIFNa2_M148A
(SEQ ID NO: 30)

DKTHTCPPCPAPEAAGGPSVFLFPPKPKDTLMISRTPEVTCVVVDVSHEDPEVKFNWYVDGVEVHNAKTKPREE

QYNSTYRVVSVLTVLHQDWLNGKEYKCQVSNKALPAPIEKTISKAKGQPREPQVYTLPPCRDELTKNQVSLWCL

VKGFYPSDIAVEWESNGQPENNYKTTPPVLDSDGSFFLYSKLTVDKSRWQQGNVFSCSVMHEALHNHYTQKSL

SLSPGKGGSGGSGGSGGSGGSGGSGGSGGSGGSGGSGCDLPQTHSLGSRRTLMLLAQMRKISLFSCLKDRH

DFGFPQEEFGNQFQKAETIPVLHEMIQQIFNLFSTKDSSAAWDETLLDKFYTELYQQLNDLEACVIQGVGVTETPL

MKEDSILAVRKYFQRITLYLKEKKYSPCAWEVVRAE▓RSFSLSTNLQESLRSKE

C. hIgG1 Fc_L234A_L235A_K322Q_S354C_T366W-**10*GGS-G**-hIFNa2_T106E_A145G
(SEQ ID NO: 31)

DKTHTCPPCPAPEAAGGPSVFLFPPKPKDTLMISRTPEVTCVVVDVSHEDPEVKFNWYVDGVEVHNAKTKPREE

QYNSTYRVVSVLTVLHQDWLNGKEYKCQVSNKALPAPIEKTISKAKGQPREPQVYTLPPCRDELTKNQVSLWCL

VKGFYPSDIAVEWESNGQPENNYKTTPPVLDSDGSFFLYSKLTVDKSRWQQGNVFSCSVMHEALHNHYTQKSL

SLSPGKGGSGGSGGSGGSGGSGGSGGSGGSGGSGGSGCDLPQTHSLGSRRTLMLLAQMRKISLFSCLKDRH

DFGFPQEEFGNQFQKAETIPVLHEMIQQIFNLFSTKDSSAAWDETLLDKFYTELYQQLNDLEACVIQGVGVEETP

LMKEDSILAVRKYFQRITLYLKEKKYSPCAWEWR▓EIMRSFSLSTNLQESLRSKE

D. hIgG1 Fc_L234A_L235A_K322Q_S354C_T366W-**10*GGS-G**-hIFNa2_A145G
(SEQ ID NO: 32)

DKTHTCPPCPAPEAAGGPSVFLFPPKPKDTLMISRTPEVTCVVVDVSHEDPEVKFNWYVDGVEVHNAKTKPREE

QYNSTYRVVSVLTVLHQDWLNGKEYKCQVSNKALPAPIEKTISKAKGQPREPQVYTLPPCRDELTKNQVSLWCL

VKGFYPSDIAVEWESNGQPENNYKTTPPVLDSDGSFFLYSKLTVDKSRWQQGNVFSCSVMHEALHNHYTQKSL

SLSPGKGGSGGSGGSGGSGGSGGSGGSGGSGGSGGSGCDLPQTHSLGSRRTLMLLAQMRKISLFSCLKDRH

DFGFPQEEFGNQFQKAETIPVLHEMIQQIFNLFSTKDSSAAWDETLLDKFYTELYQQLNDLEACVIQGVGVTETPL

MKEDSILAVRKYFQRITLYLKEKKYSPCAWEWRGEIMRSFSLSTNLQESLRSKE

E. hIgG1 Fc_L234A_L235A_K322Q_T366Y-**10*GGS-G**-hIFNa2_T106E_M148A
(SEQ ID NO: 33)

DKTHTCPPCPAPEAAGGPSVFLFPPKPKDTLMISRTPEVTCVVVDVSHEDPEVKFNWYVDGVEVHNAKTKPREE

QYNSTYRVVSVLTVLHQDWLNGKEYKCQVSNKALPAPIEKTISKAKGQPREPQVYTLPPSRDELTKNQVSLYCL

VKGFYPSDIAVEWESNGQPENNYKTTPPVLDSDGSFFLYSKLTVDKSRWQQGNVFSCSVMHEALHNHYTQKSL

SLSPGKGGSGGSGGSGGSGGSGGSGGSGGSGGSGGSGCDLPQTHSLGSRRTLMLLAQMRKISLFSCLKDRH

DFGFPQEEFGNQFQKAETIPVLHEMIQQIFNLFSTKDSSAAWDETLLDKFYTELYQQLNDLEACVIQGVGVEETP

LMKEDSILAVRKYFQRITLYLKEKKYSPCAWEVVRAEI▓RSFSLSTNLQESLRSKE

F. hIgG1 Fc_L234A_L235A_K322Q_T366Y-**10*GGS-G**-hIFNa2_M148A
(SEQ ID NO: 34)

DKTHTCPPCPAPEAAGGPSVFLFPPKPKDTLMISRTPEVTCVVVDVSHEDPEVKFNWYVDGVEVHNAKTKPREE

QYNSTYRVVSVLTVLHQDWLNGKEYKCQVSNKALPAPIEKTISKAKGQPREPQVYTLPPSRDELTKNQVSLYCL

VKGFYPSDIAVEWESNGQPENNYKTTPPVLDSDGSFFLYSKLTVDKSRWQQGNVFSCSVMHEALHNHYTQKSL

SLSPGKGGSGGSGGSGGSGGSGGSGGSGGSGGSGGSGCDLPQTHSLGSRRTLMLLAQMRKISLFSCLKDRH

DFGFPQEEFGNQFQKAETIPVLHEMIQQIFNLFSTKDSSAAWDETLLDKFYTELYQQLNDLEACVIQGVGVTETPL

MKEDSILAVRKYFQRITLYLKEKKYSPCAWEVVRAEI▓RSFSLSTNLQESLRSKE

-continued

G. hIgG1 Fc_L234A_L235A_K322Q_T366Y-**10*GGS-G**-hIFNa2_T106E_A145G
(SEQ ID NO: 35)
DKTHTCPPCPAPEAAGGPSVFLFPPKPKDTLMISRTPEVTCVVVDVSHEDPEVKFNWYVDGVEVHNAKTKPREE

QYNSTYRVVSVLTVLHQDWLNGKEYKCQVSNKALPAPIEKTISKAKGQPREPQVYTLPPSRDELTKNQVSLYCL

VKGFYPSDIAVEWESNGQPENNYKTTPPVLDSDGSFFLYSKLTVDKSRWQQGNVFSCSVMHEALHNHYTQKSL

SLSPGKGGSGGSGGSGGSGGSGGSGGSGGSGGSGGSGCDLPQTHSLGSRRTLMLLAQMRKISLFSCLKDRH

DFGFPQEEFGNQFQKAETIPVLHEMIQQIFNLFSTKDSSAAWDETLLLDKFYTELYQQLNDLEACVIQGVGVEETP

LMKEDSILAVRKYFQRITLYLKEKKYSPCAWEWR ⬛EIMRSFSLSTNLQESLRSKE

H. hIgG1 Fc_L234A_L235A_K322Q_T366Y-**10*GGS-G**-hIFNa2_A145G
(SEQ ID NO: 36)
DKTHTCPPCPAPEAAGGPSVFLFPPKPKDTLMISRTPEVTCVVVDVSHEDPEVKFNWYVDGVEVHNAKTKPREE

QYNSTYRVVSVLTVLHQDWLNGKEYKCQVSNKALPAPIEKTISKAKGQPREPQVYTLPPSRDELTKNQVSLYCL

VKGFYPSDIAVEWESNGQPENNYKTTPPVLDSDGSFFLYSKLTVDKSRWQQGNVFSCSVMHEALHNHYTQKSL

SLSPGKGGSGGSGGSGGSGGSGGSGGSGGSGGSGGSGCDLPQTHSLGSRRTLMLLAQMRKISLFSCLKDRH

DFGFPQEEFGNQFQKAETIPVLHEMIQQIFNLFSTKDSSAAWDETLLLDKFYTELYQQLNDLEACVIQGVGVTETPL

MKEDSILAVRKYFQRITLYLKEKKYSPCAWEWR ⬛EIMRSFSLSTNLQESLRSKE

To generate human CLEC9A targeted AFNs, any of the above constructs A-D was combined with the CLEC9A VHH-Fc fusion of SEQ ID 2 or 4 resulting in 8 novel constructs. In addition, any of the above constructs E-H was combined with the CLEC9A VHH-Fc fusion of SEQ ID 1 or 3 resulting in an additional set of 8 novel constructs. Proteins were expressed and purified as described in Example 5.

Example 8: A145G Mutation with or without O-Glycosylation on T106

In this experiment, Clec9A targeted AFNs with and without T106 O-glycosylation in IFNa2 (R1CHCL50-Fc3+Fc4-IFNa2_A145G versus R1CHCL50-Fc3+Fc4-IFNa2_T106E_A145G), and an untargeted variant (Fc3+Fc4-IFNa2_A145G) were compared. Proteins were produced as described in Example 5 and purified by protein A chromatography followed by size exclusion.

Figure 10A:
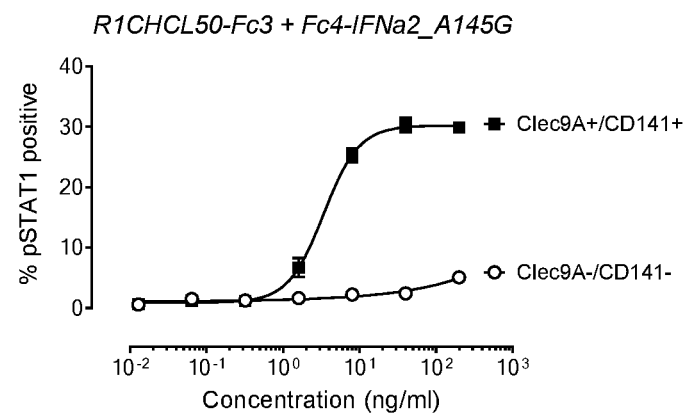
FIGS. 10A-C show pSTAT1 activity in CLEC9A−/CD141− and CLEC9A+/CD141+ PBMC's after treatment with Clec9A targeted AFNs with (FIG. 10A) and without T106 O-glycosylation in IFNα2 (FIG. 10B), and an untargeted variant (FIG. 10C).
Figure 10B:
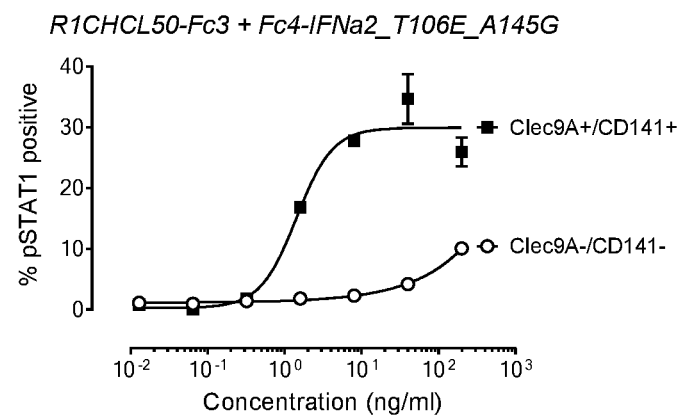
Figure 10C:
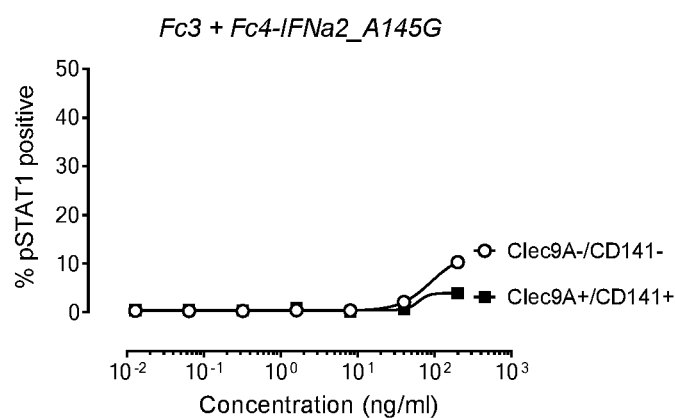

To evaluate the potency the constructs were tested for STAT1 phosphorylation in primary cDC1 (CLEC9A+/CD141+) and non-cDC1 (CLEC9A−/CD141−) populations in human PBMC as described in Example 5. FIG. 10 shows the specificity of the CLEC9A targeted construct with or without O-glycosylation on T106 as this construct is much more potent in activating IFN signaling in cDC1 cells compared to non-cDC1 cells and is much more potent on cDC1 cells compared to cDC1 cells treated with the untargeted variant.

Figure 11:
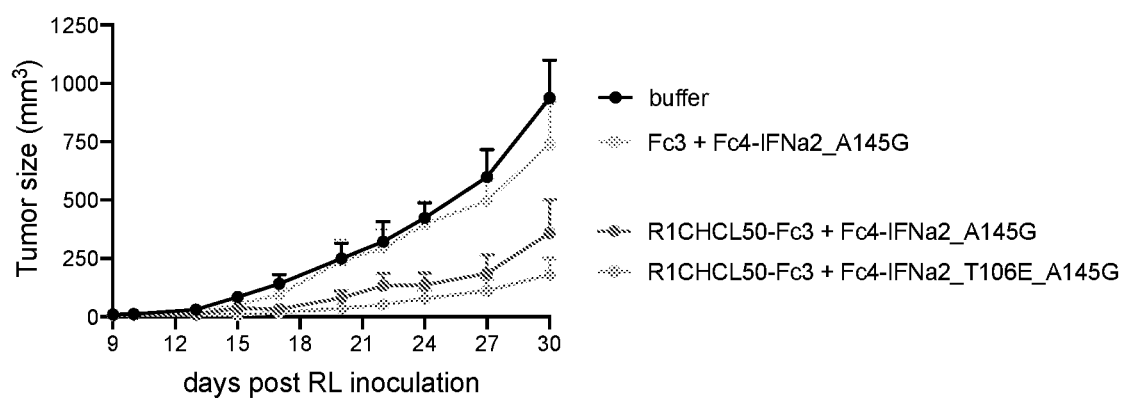
FIG. 11 shows anti-tumor activity of Clec9A targeted-AFN Fc with the A145G mutation of IFNα2.

To evaluate the in vivo efficacy of the aforementioned heterodimeric, 'knob-in-hole' Fc AFN construct, they were tested in a tumor model in a humanized mouse. In brief, new-born NSG mice (1-2 days of age) were sublethal irradiated with 100 cGy prior to intrahepatic delivery of $1 \times 10^5$ CD34+ human stem cells (from HLA-A2 positive cord bloods). At week 13 after stem cell transfer mice were subcutaneously inoculated with $25 \times 10^5$ human RL follicular lymphoma cells (ATCC CRL-2261; not sensitive to the direct anti-proliferative effect of IFN). Mice were treated intraperitoneally with 30 μg of human Flt3L protein, from day 7 to day 17 after tumor inoculation. Weekly intravenous injection with buffer or Fc-AFN (2.5 μg) constructs was initiated at day 9 after tumor inoculation, when a palpable tumor was visible (n=5 mice per group). Tumor size (caliper measurements), body weight and temperature were assessed daily. Data in FIG. 11 show the tumor growth until one week after the third treatment and demonstrates that both targeted AFNs induced a strong level of tumor growth, while no significant effect was observed with the untargeted variant. Data on body weight and temperature did not show any major difference between buffer treatment and AFN treatment supporting that all AFN treatments were well tolerated.
Sequences 1. P-1479: R1CHCL50-*Fc3*
(SEQ ID NO: 2)
DVQLVESGGGLVQPGGSLRLSCAASGSFSSINVMGWYRQAPGKERELVARITNLGLPNYADSVKGRFTISRDN

SKNTVYLQMNSLRPEDTAVYYCYLVALKAEYWGQGTLVTVSSGGSGGSGGSGGSGGSDKTHTCPPCPAPEA

AGGPSVFLFPPKPKDTLMISRTPEVTCVVVDVSHEDPEVKFNWYVDGVEVHNAKTKPREEQYNSTYRVVSVLT

VLHQDWLNGKEYKCQVSNKALPAPIEKTISKAKGQPREPQVCTLPPSRDELTKNQVSLSCAVKGFYPSDIAVEW

ESNGQPENNYKTTPPVLDSDGSFFLVSKLTVDKSRWQQGNVFSCSVMHEALHNHYTQKSLSLSPGK

2. P-1542: Fc3

(SEQ ID NO: 38)

DKTHTCPPCPAPEAAGGPSVFLFPPKPKDTLMISRTPEVTCVVVDVSHEDPEVKFNWYVDGVEVHNAKTKPRE

EQYNSTYRVVSVLTVLHQDWLNGKEYKCQVSNKALPAPIEKTISKAKGQPREPQVCTLPPSRDELTKNQVSLSC

AVKGFYPSDIAVEWESNGQPENNYKTTPPVLDSDGSFFLVSKLTVDKSRWQQGNVFSCSVMHEALHNHYTQK

SLSLSPGK

3. P-2157: Fc4-IFNa2

(SEQ ID NO: 32)

DKTHTCPPCPAPEAAGGPSVFLFPPKPKDTLMISRTPEVTCVVVDVSHEDPEVKFNWYVDGVEVHNAKTKPREEQYNSTY

RVVSVLTVLHQDWLNGKEYKCQVSNKALPAPIEKTISKAKGQPREPQVYTLPPCRDELTKNQVSLWCLVKGFYPSDIAVEW

ESNGQPENNYKTTPPVLDSDGSFFLYSKLTVDKSRWQQGNVFSCSVMHEALHNHYTQKSLSLSPGKGGSGGSGGSGGS

GGSGGSGGSGGSGGSGGSGCDLPQTHSLGSRRTLMLLAQMRRISLFSCLKDRHDFGFPQEEFGNQFQKAETIPVLHEMI

QQIFNLFSTKDSSAAWDETLLDKFYTELYQQLNDLEACVIQGVGVETPLMKEDSILAVRKYFQRITLYLKEKKYSPCAWEW

REIMRSFSLSTNLQESLRSKE

4. P-2158: Fc4-IFNa2

(SEQ ID NO: 31)

DKTHTCPPCPAPEAAGGPSVFLFPPKPKDTLMISRTPEVTCVVVDVSHEDPEVKFNWYVDGVEVHNAKTKPRE

EQYNSTYRVVSVLTVLHQDWLNGKEYKCQVSNKALPAPIEKTISKAKGQPREPQVYTLPPCRDELTKNQVSLW

CLVKGFYPSDIAVEWESNGQPENNYKTTPPVLDSDGSFFLYSKLTVDKSRWQQGNVFSCSVMHEALHNHYTQ

KSLSLSPGKGGSGGSGGSGGSGGSGGSGGSGGSGGSGGSGCDLPQTHSLGSRRTLMLLAQMRRISLFSCLK

DRHDFGFPQEEFGNQFQKAETIPVLHEMIQQIFNLFSTKDSSAAWDETLLDKFYTELYQQLNDLEACVIQGVGV

ETPLMKEDSILAVRKYFQRITLYLKEKKYSPCAWEWR EIMRSFSLSTNLQESLRSKE

Example 9: Fc-AFN Constructs

Mass spectrometry analysis illustrated that the C-terminal lysine K residue in the R1CHCL50-Fc3 chain is cleaved off in almost all mature proteins. Therefore, variants are constructed in which this lysine residue in both Fc-chains was removed. Resulting proteins will be referred to as Fc′ proteins. By way of example, the sequences for the chimeric protein combination of R1CHCL50-Fc3′ with Fc4′-AFN fusions in which residue A145 was mutated to G in IFNa2b, or in which the residues T106 and A145 were mutated to respectively E and G in IFNa2a, are shown below.

Sequences:

P-2379: Fc4'-IFNa2b_A145G (SEQ ID NO: 41)

DKTHTCPPCPAPEAAGGPSVFLFPPKPKDTLMISRTPEVTCVVVDVSHEDPEVKFNWYVDGVEVHNAKTKPREE

QYNSTYRVVSVLTVLHQDWLNGKEYKCQVSNKALPAPIEKTISKAKGQPREPQVYTLPPCRDELTKNQVSLWCL

VKGFYPSDIAVEWESNGQPENNYKTTPPVLDSDGSFFLYSKLTVDKSRWQQGNVFSCSVMHEALHNHYTQKSL

SLSPGGGSGGSGGSGGSGGSGGSGGSGGSGGSGGSGCDLPQTHSLGSRRTLMLLAQMRRISLFSCLKDRHD

FGFPQEEFGNQFQKAETIPVLHEMIQQIFNLFSTKDSSAAWDETLLDKFYTELYQQLNDLEACVIQGVGVTETPL

MKEDSILAVRKYFQRITLYLKEKKYSPCAWEWR EIMRSFSLSTNLQESLRSKE

P-2380: Fc4'-IFNa2a_T106E_A145G (SEQ ID NO: 42)

DKTHTCPPCPAPEAAGGPSVFLFPPKPKDTLMISRTPEVTCVVVDVSHEDPEVKFNWYVDGVEVHNAKTKPREE

QYNSTYRVVSVLTVLHQDWLNGKEYKCQVSNKALPAPIEKTISKAKGQPREPQVYTLPPCRDELTKNQVSLWCL

VKGFYPSDIAVEWESNGQPENNYKTTPPVLDSDGSFFLYSKLTVDKSRWQQGNVFSCSVMHEALHNHYTQKSL

SLSPGGGSGGSGGSGGSGGSGGSGGSGGSGGSGGSGCDLPQTHSLGSRRTLMLLAQMRRISLFSCLKDRHD

FGFPQEEFGNQFQKAETIPVLHEMIQQIFNLFSTKDSSAAWDETLLDKFYTELYQQLNDLEACVIQGVGV ETPL

MKEDSILAVRKYFQRITLYLKEKKYSPCAWEWR EIMRSFSLSTNLQESLRSKE

-continued

P-1479b: R1CHCL50-Fc3"

(SEQ ID NO: 43)

DVQLVESGGGLVQPGGSLRLSCAASGSFSSINVMGWYRQAPGKERELVARITNLGLPNYADSVKGRFTISRDNS
KNTVYLQMNSLRPEDTAVYYCYLVALKAEYWGQGTLVTVSSGGSGGSGGSGGSGGSDKTHTCPPCPAPEAAG
GPSVFLFPPKPKDTLMISRTPEVTCVVVDVSHEDPEVKFNWYVDGVEVHNAKTKPREEQYNSTYRVVSVLTVLH
QDWLNGKEYKCQVSNKALPAPIEKTISKAKGQPREPQVCTLPPSRDELTKNQVSLSCAVKGFYPSDIAVEWESN
GQPENNYKTTPPVLDSDGSFFLVSKLTVDKSRWQQGNVFSCSVMHEALHNHYTQKSLSLSPG

---

What is claimed is:

1. A chimeric protein complex comprising:
   (i) a targeting moiety that specifically binds to C-type lectin domain family 9 member A (Clec9A),
   (ii) a modified human IFNα2, and
   (iii) a modified Fc domain,
   wherein the chimeric protein complex comprises a polypeptide having the amino acid sequence of SEQ ID NO: 2 and further comprises a polypeptide having the amino acid sequence of SEQ ID NO: 7.

2. A method for treating a cancer, comprising administering an effective amount of the chimeric protein complex of claim 1 to a patient in need thereof.

3. A pharmaceutical composition comprising the chimeric protein complex of claim 1 and a pharmaceutically acceptable carrier.

4. A recombinant nucleic acid composition encoding the chimeric protein complex of claim 1, or constituents thereof.

5. A host cell comprising the nucleic acid of claim 4.

* * * * *

SEQUENCE LISTING

<160> NUMBER OF SEQ ID NOS: 43

<210> SEQ ID NO 1
<211> LENGTH: 357
<212> TYPE: PRT
<213> ORGANISM: Artificial Sequence
<220> FEATURE:
<223> OTHER INFORMATION: Synthetic Sequence

<400> SEQUENCE: 1

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Phe Ser Ser Ile Asn
            20                  25                  30

Val Met Gly Trp Tyr Arg Gln Ala Pro Gly Lys Glu Arg Glu Leu Val
        35                  40                  45

Ala Arg Ile Thr Asn Leu Gly Leu Pro Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Tyr
                85                  90                  95

Leu Val Ala Leu Lys Ala Glu Tyr Trp Gly Gln Gly Thr Leu Val Thr
            100                 105                 110

Val Ser Ser Gly Gly Ser Gly Gly Ser Gly Gly Ser Gly Gly Ser Gly
        115                 120                 125

Gly Ser Asp Lys Thr His Thr Cys Pro Pro Cys Pro Ala Pro Glu Ala
    130                 135                 140

Ala Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Gln Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala

```
                275                 280                 285
Val Glu Trp Glu Ser Asn Gly Gln Pro Glu Asn Asn Tyr Lys Thr Thr
    290                 295                 300
Pro Pro Val Leu Asp Ser Asp Gly Ser Phe Phe Leu Thr Ser Lys Leu
305                 310                 315                 320
Thr Val Asp Lys Ser Arg Trp Gln Gln Gly Asn Val Phe Ser Cys Ser
                325                 330                 335
Val Met His Glu Ala Leu His Asn His Tyr Thr Gln Lys Ser Leu Ser
            340                 345                 350
Leu Ser Pro Gly Lys
            355

<210> SEQ ID NO 2
<211> LENGTH: 357
<212> TYPE: PRT
<213> ORGANISM: Artificial Sequence
<220> FEATURE:
<223> OTHER INFORMATION: Synthetic Sequence

<400> SEQUENCE: 2

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Phe Ser Ser Ile Asn
            20                  25                  30

Val Met Gly Trp Tyr Arg Gln Ala Pro Gly Lys Glu Arg Glu Leu Val
        35                  40                  45

Ala Arg Ile Thr Asn Leu Gly Leu Pro Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Tyr
                85                  90                  95

Leu Val Ala Leu Lys Ala Glu Tyr Trp Gly Gln Gly Thr Leu Val Thr
            100                 105                 110

Val Ser Ser Gly Gly Ser Gly Gly Ser Gly Gly Ser Gly Gly Ser Gly
        115                 120                 125

Gly Ser Asp Lys Thr His Thr Cys Pro Pro Cys Pro Ala Pro Glu Ala
    130                 135                 140

Ala Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Gln Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Cys Thr Leu Pro Pro Ser Arg Asp Glu Leu Thr Lys Asn Gln
            260                 265                 270

Val Ser Leu Ser Cys Ala Val Lys Gly Phe Tyr Pro Ser Asp Ile Ala
```

```
            275                 280                 285
Val Glu Trp Glu Ser Asn Gly Gln Pro Glu Asn Asn Tyr Lys Thr Thr
    290                 295                 300
Pro Pro Val Leu Asp Ser Asp Gly Ser Phe Phe Leu Val Ser Lys Leu
305                 310                 315                 320
Thr Val Asp Lys Ser Arg Trp Gln Gln Gly Asn Val Phe Ser Cys Ser
                325                 330                 335
Val Met His Glu Ala Leu His Asn His Tyr Thr Gln Lys Ser Leu Ser
            340                 345                 350
Leu Ser Pro Gly Lys
            355

<210> SEQ ID NO 3
<211> LENGTH: 357
<212> TYPE: PRT
<213> ORGANISM: Artificial Sequence
<220> FEATURE:
<223> OTHER INFORMATION: Synthetic Sequence

<400> SEQUENCE: 3

Asp Val Gln Leu Val Glu Ser Gly Gly Gly Leu Val Gln Pro Gly Gly
1               5                   10                  15
Ser Leu Arg Leu Ser Cys Ala Ala Ser Gly Arg Ile Phe Ser Val Asn
            20                  25                  30
Ala Met Gly Trp Tyr Arg Gln Ala Pro Gly Lys Gln Arg Glu Leu Val
        35                  40                  45
Ala Ala Ile Thr Asn Gln Gly Ala Pro Thr Tyr Ala Asp Ser Val Lys
    50                  55                  60
Gly Arg Phe Thr Ile Ser Arg Asp Asn Ser Lys Asn Thr Val Tyr Leu
65                  70                  75                  80
Gln Met Asn Ser Leu Arg Pro Glu Asp Thr Ala Val Tyr Tyr Cys Lys
                85                  90                  95
Ala Phe Thr Arg Gly Asp Asp Tyr Trp Gly Gln Gly Thr Leu Val Thr
            100                 105                 110
Val Ser Ser Gly Gly Ser Gly Gly Ser Gly Gly Ser Gly Gly Ser Gly
        115                 120                 125
Gly Ser Asp Lys Thr His Thr Cys Pro Pro Cys Pro Ala Pro Glu Ala
    130                 135                 140
Ala Gly Gly Pro Ser Val Phe Leu Phe Pro Pro Lys Pro Lys Asp Thr
145                 150                 155                 160
Leu Met Ile Ser Arg Thr Pro Glu Val Thr Cys Val Val Val Asp Val
                165                 170                 175
Ser His Glu Asp Pro Glu Val Lys Phe Asn Trp Tyr Val Asp Gly Val
            180                 185                 190
Glu Val His Asn Ala Lys Thr Lys Pro Arg Glu Glu Gln Tyr Asn Ser
        195                 200                 205
Thr Tyr Arg Val Val Ser Val Leu Thr Val Leu His Gln Asp Trp Leu
    210                 215                 220
Asn Gly Lys Glu Tyr Lys Cys Gln Val Ser Asn Lys Ala Leu Pro Ala
225                 230                 235                 240
Pro Ile Glu Lys Thr Ile Ser Lys Ala Lys Gly Gln Pro Arg Glu Pro
                245                 250                 255
Gln Val Tyr Thr Leu Pro Pro Ser Arg Asp Glu Leu Thr Lys Asn Gln
            260                 265                 270
Val Ser Leu Thr Cys Leu Val Lys Gly Phe Tyr Pro Ser Asp Ile Ala
```

```
                275                 280                 285
Val Glu Trp Glu Ser Asn Gly Gln Pro Glu Asn Asn Tyr Lys Thr Thr
    290                 295                 300
Pro Pro Val Leu Asp Ser Asp Gly Ser Phe Phe Leu Thr Ser Lys Leu
305                 310                 315                 320
Thr Val Asp Lys Ser Arg Trp Gln Gln Gly Asn Val Phe Ser Cys Ser
                325                 330                 335
Val Met His Glu Ala Leu His Asn His Tyr Thr Gln Lys Ser Leu Ser
            340                 345                 350
Leu Ser Pro Gly Lys
            355

<210> SEQ ID NO 4
<211> LENGTH: 357
<212> TYPE: PRT
<213> ORGANISM: Artificial Sequence
<220> FEATURE:
<223> OTHER INFORMATION: Synthetic Sequence

<400> SEQUENCE: 4

Asp Val Gln Leu Val Glu Ser Gly Gly Gly Leu Val Gln Pro Gly Gly
1               5                   10                  15
Ser Leu Arg Leu Ser Cys Ala Ala Ser Gly Arg Ile Phe Ser Val Asn
            20                  25                  30
Ala Met Gly Trp Tyr Arg Gln Ala Pro Gly Lys Gln Arg Glu Leu Val
        35                  40                  45
Ala Ala Ile Thr Asn Gly Ala Pro Thr Tyr Ala Asp Ser Val Lys
    50                  55                  60
Gly Arg Phe Thr Ile Ser Arg Asp Asn Ser Lys Asn Thr Val Tyr Leu
65                  70                  75                  80
Gln Met Asn Ser Leu Arg Pro Glu Asp Thr Ala Val Tyr Tyr Cys Lys
                85                  90                  95
Ala Phe Thr Arg Gly Asp Asp Tyr Trp Gly Gln Gly Thr Leu Val Thr
            100                 105                 110
Val Ser Ser Gly Gly Ser Gly Gly Ser Gly Gly Ser Gly Gly Ser Gly
        115                 120                 125
Gly Ser Asp Lys Thr His Thr Cys Pro Pro Cys Pro Ala Pro Glu Ala
    130                 135                 140
Ala Gly Gly Pro Ser Val Phe Leu Phe Pro Pro Lys Pro Lys Asp Thr
145                 150                 155                 160
Leu Met Ile Ser Arg Thr Pro Glu Val Thr Cys Val Val Val Asp Val
                165                 170                 175
Ser His Glu Asp Pro Glu Val Lys Phe Asn Trp Tyr Val Asp Gly Val
            180                 185                 190
Glu Val His Asn Ala Lys Thr Lys Pro Arg Glu Glu Gln Tyr Asn Ser
        195                 200                 205
Thr Tyr Arg Val Val Ser Val Leu Thr Val Leu His Gln Asp Trp Leu
    210                 215                 220
Asn Gly Lys Glu Tyr Lys Cys Gln Val Ser Asn Lys Ala Leu Pro Ala
225                 230                 235                 240
Pro Ile Glu Lys Thr Ile Ser Lys Ala Lys Gly Gln Pro Arg Glu Pro
                245                 250                 255
Gln Val Cys Thr Leu Pro Pro Ser Arg Asp Glu Leu Thr Lys Asn Gln
            260                 265                 270
Val Ser Leu Ser Cys Ala Val Lys Gly Phe Tyr Pro Ser Asp Ile Ala
```

```
                275                 280                 285
Val Glu Trp Glu Ser Asn Gly Gln Pro Glu Asn Asn Tyr Lys Thr Thr
        290                 295                 300
Pro Pro Val Leu Asp Ser Asp Gly Ser Phe Phe Leu Val Ser Lys Leu
305                 310                 315                 320
Thr Val Asp Lys Ser Arg Trp Gln Gln Gly Asn Val Phe Ser Cys Ser
                325                 330                 335
Val Met His Glu Ala Leu His Asn His Tyr Thr Gln Lys Ser Leu Ser
            340                 345                 350
Leu Ser Pro Gly Lys
            355

<210> SEQ ID NO 5
<211> LENGTH: 423
<212> TYPE: PRT
<213> ORGANISM: Artificial Sequence
<220> FEATURE:
<223> OTHER INFORMATION: Synthetic Sequence

<400> SEQUENCE: 5

Asp Lys Thr His Thr Cys Pro Pro Cys Pro Ala Pro Glu Ala Ala Gly
1               5                   10                  15
Gly Pro Ser Val Phe Leu Phe Pro Pro Lys Pro Lys Asp Thr Leu Met
                20                  25                  30
Ile Ser Arg Thr Pro Glu Val Thr Cys Val Val Val Asp Val Ser His
            35                  40                  45
Glu Asp Pro Glu Val Lys Phe Asn Trp Tyr Val Asp Gly Val Glu Val
        50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
                85                  90                  95
Lys Glu Tyr Lys Cys Gln Val Ser Asn Lys Ala Leu Pro Ala Pro Ile
            100                 105                 110
Glu Lys Thr Ile Ser Lys Ala Lys Gly Gln Pro Arg Glu Pro Gln Val
        115                 120                 125
Tyr Thr Leu Pro Pro Ser Arg Asp Glu Leu Thr Lys Asn Gln Val Ser
130                 135                 140
Leu Tyr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys Gly Gly Ser Gly Gly Ser Gly Gly Ser Gly Gly Ser Gly
225                 230                 235                 240
Gly Ser Gly Gly Ser Gly Gly Ser Gly Gly Ser Gly Gly Ser Gly Gly
                245                 250                 255
Ser Gly Cys Asp Leu Pro Gln Thr His Ser Leu Gly Ser Arg Arg Thr
            260                 265                 270
Leu Met Leu Leu Ala Gln Met Arg Arg Ile Ser Leu Phe Ser Cys Leu
```

```
            275                 280                 285
Lys Asp Arg His Asp Phe Gly Phe Pro Gln Glu Phe Gly Asn Gln
    290                 295                 300

Phe Gln Lys Ala Glu Thr Ile Pro Val Leu His Glu Met Ile Gln Gln
305                 310                 315                 320

Ile Phe Asn Leu Phe Ser Thr Lys Asp Ser Ala Ala Trp Asp Glu
                    325                 330                 335

Thr Leu Leu Asp Lys Phe Tyr Thr Glu Leu Tyr Gln Gln Leu Asn Asp
                    340                 345                 350

Leu Glu Ala Cys Val Ile Gln Gly Val Gly Val Thr Glu Thr Pro Leu
                    355                 360                 365

Met Lys Glu Asp Ser Ile Leu Ala Val Arg Lys Tyr Phe Gln Arg Ile
    370                 375                 380

Thr Leu Tyr Leu Lys Glu Lys Lys Tyr Ser Pro Cys Ala Trp Glu Val
385                 390                 395                 400

Val Arg Ala Glu Ile Met Ala Ser Phe Ser Leu Ser Thr Asn Leu Gln
                    405                 410                 415

Glu Ser Leu Arg Ser Lys Glu
                    420

<210> SEQ ID NO 6
<211> LENGTH: 423
<212> TYPE: PRT
<213> ORGANISM: Artificial Sequence
<220> FEATURE:
<223> OTHER INFORMATION: Synthetic Sequence

<400> SEQUENCE: 6

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Gln Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Tyr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
```

```
            210                 215                 220
Pro Gly Lys Gly Gly Ser Gly Gly Ser Gly Gly Ser Gly
225                 230                 235                 240

Gly Ser Gly Gly Ser Gly Gly Ser Gly Gly Ser Gly Gly
                245                 250                 255

Ser Gly Cys Asp Leu Pro Gln Thr His Ser Leu Gly Ser Arg Arg Thr
            260                 265                 270

Leu Met Leu Leu Ala Gln Met Arg Arg Ile Ser Leu Phe Ser Cys Leu
            275                 280                 285

Lys Asp Arg His Asp Phe Gly Phe Pro Gln Glu Glu Phe Gly Asn Gln
            290                 295                 300

Phe Gln Lys Ala Glu Thr Ile Pro Val Leu His Glu Met Ile Gln Gln
305                 310                 315                 320

Ile Phe Asn Leu Phe Ser Thr Lys Asp Ser Ser Ala Ala Trp Asp Glu
                325                 330                 335

Thr Leu Leu Asp Lys Phe Tyr Thr Glu Leu Tyr Gln Gln Leu Asn Asp
            340                 345                 350

Leu Glu Ala Cys Val Ile Gln Gly Val Gly Val Thr Glu Thr Pro Leu
            355                 360                 365

Met Lys Glu Asp Ser Ile Leu Ala Val Arg Lys Tyr Phe Gln Arg Ile
            370                 375                 380

Thr Leu Tyr Leu Lys Glu Lys Lys Tyr Ser Pro Cys Ala Trp Glu Val
385                 390                 395                 400

Val Arg Ala Glu Ile Met Ala Ser Phe Ser Leu Ser Thr Asn Leu Gln
                405                 410                 415

Glu Ser Leu Arg Ser Lys Glu
            420

<210> SEQ ID NO 7
<211> LENGTH: 423
<212> TYPE: PRT
<213> ORGANISM: Artificial Sequence
<220> FEATURE:
<223> OTHER INFORMATION: Synthetic Sequence

<400> SEQUENCE: 7

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Gln Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
            130                 135                 140

Leu Trp Cys Leu Val Lys Gly Phe Tyr Pro Ser Asp Ile Ala Val Glu
```

```
145                 150                 155                 160
Trp Glu Ser Asn Gly Gln Pro Glu Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
            195                 200                 205
His Glu Ala Leu His Asn His Tyr Thr Gln Lys Ser Leu Ser Leu Ser
        210                 215                 220
Pro Gly Lys Gly Gly Ser Gly Gly Ser Gly Gly Ser Gly Gly Ser Gly
225                 230                 235                 240
Gly Ser Gly Gly Ser Gly Gly Ser Gly Gly Ser Gly Gly Ser Gly Gly
                245                 250                 255
Ser Gly Cys Asp Leu Pro Gln Thr His Ser Leu Gly Ser Arg Arg Thr
            260                 265                 270
Leu Met Leu Leu Ala Gln Met Arg Arg Ile Ser Leu Phe Ser Cys Leu
        275                 280                 285
Lys Asp Arg His Asp Phe Gly Phe Pro Gln Glu Glu Phe Gly Asn Gln
    290                 295                 300
Phe Gln Lys Ala Glu Thr Ile Pro Val Leu His Glu Met Ile Gln Gln
305                 310                 315                 320
Ile Phe Asn Leu Phe Ser Thr Lys Asp Ser Ser Ala Ala Trp Asp Glu
                325                 330                 335
Thr Leu Leu Asp Lys Phe Tyr Thr Glu Leu Tyr Gln Gln Leu Asn Asp
            340                 345                 350
Leu Glu Ala Cys Val Ile Gln Gly Val Gly Val Thr Glu Thr Pro Leu
        355                 360                 365
Met Lys Glu Asp Ser Ile Leu Ala Val Arg Lys Tyr Phe Gln Arg Ile
    370                 375                 380
Thr Leu Tyr Leu Lys Glu Lys Lys Tyr Ser Pro Cys Ala Trp Glu Val
385                 390                 395                 400
Val Arg Ala Glu Ile Met Ala Ser Phe Ser Leu Ser Thr Asn Leu Gln
                405                 410                 415
Glu Ser Leu Arg Ser Lys Glu
            420

<210> SEQ ID NO 8
<211> LENGTH: 423
<212> TYPE: PRT
<213> ORGANISM: Artificial Sequence
<220> FEATURE:
<223> OTHER INFORMATION: Synthetic Sequence

<400> SEQUENCE: 8

Asp Lys Thr His Thr Cys Pro Pro Cys Pro Ala Pro Glu Ala Ala Gly
1               5                   10                  15
Gly Pro Ser Val Phe Leu Phe Pro Pro Lys Pro Lys Asp Thr Leu Met
            20                  25                  30
Ile Ser Arg Thr Pro Glu Val Thr Cys Val Val Val Asp Val Ser His
        35                  40                  45
Glu Asp Pro Glu Val Lys Phe Asn Trp Tyr Val Asp Gly Val Glu Val
    50                  55                  60
His Asn Ala Lys Thr Lys Pro Arg Glu Glu Gln Tyr Asn Ser Thr Tyr
65                  70                  75                  80
Arg Val Val Ser Val Leu Thr Val Leu His Gln Asp Trp Leu Asn Gly
```

```
                    85                  90                  95
Lys Glu Tyr Lys Cys Gln Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Cys Arg Asp Glu Leu Thr Lys Asn Gln Val Ser
        130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys Gly Gly Ser Gly Gly Ser Gly Gly Ser Gly Gly Ser Gly
225                 230                 235                 240

Gly Ser Gly Gly Ser Gly Gly Ser Gly Gly Ser Gly Gly Ser Gly Gly
                245                 250                 255

Ser Gly Cys Asp Leu Pro Gln Thr His Ser Leu Gly Ser Arg Arg Thr
            260                 265                 270

Leu Met Leu Leu Ala Gln Met Arg Arg Ile Ser Leu Phe Ser Cys Leu
        275                 280                 285

Lys Asp Arg His Asp Phe Gly Phe Pro Gln Glu Glu Phe Gly Asn Gln
290                 295                 300

Phe Gln Lys Ala Glu Thr Ile Pro Val Leu His Glu Met Ile Gln Gln
305                 310                 315                 320

Ile Phe Asn Leu Phe Ser Thr Lys Asp Ser Ser Ala Ala Trp Asp Glu
                325                 330                 335

Thr Leu Leu Asp Lys Phe Tyr Thr Glu Leu Tyr Gln Gln Leu Asn Asp
            340                 345                 350

Leu Glu Ala Cys Val Ile Gln Gly Val Gly Val Glu Thr Pro Leu
        355                 360                 365

Met Lys Glu Asp Ser Ile Leu Ala Val Arg Lys Tyr Phe Gln Arg Ile
370                 375                 380

Thr Leu Tyr Leu Lys Glu Lys Lys Tyr Ser Pro Cys Ala Trp Glu Val
385                 390                 395                 400

Val Arg Ala Glu Ile Met Ala Ser Phe Ser Leu Ser Thr Asn Leu Gln
                405                 410                 415

Glu Ser Leu Arg Ser Lys Glu
            420

<210> SEQ ID NO 9
<211> LENGTH: 165
<212> TYPE: PRT
<213> ORGANISM: Artificial Sequence
<220> FEATURE:
<223> OTHER INFORMATION: Synthetic Sequence

<400> SEQUENCE: 9

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
```

```
                    20                  25                  30
Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 10
<211> LENGTH: 165
<212> TYPE: PRT
<213> ORGANISM: Artificial Sequence
<220> FEATURE:
<223> OTHER INFORMATION: Synthetic polymer.

<400> SEQUENCE: 10

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165

<210> SEQ ID NO 11
<211> LENGTH: 115
<212> TYPE: PRT
<213> ORGANISM: Artificial Sequence
<220> FEATURE:
<223> OTHER INFORMATION: Synthetic Sequence
```

<400> SEQUENCE: 11

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Phe Ser Ser Ile Asn
            20                  25                  30

Val Met Gly Trp Tyr Arg Gln Ala Pro Gly Lys Glu Arg Glu Leu Val
        35                  40                  45

Ala Arg Ile Thr Asn Leu Gly Leu Pro Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Tyr
                85                  90                  95

Leu Val Ala Leu Lys Ala Glu Tyr Trp Gly Gln Gly Thr Leu Val Thr
            100                 105                 110

Val Ser Ser
        115

<210> SEQ ID NO 12
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 12

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Phe Ser Val Asn
            20                  25                  30

Ala Met Gly Trp Tyr Arg Gln Ala Pro Gly Lys Gln Arg Glu Leu Val
        35                  40                  45

Ala Ala Ile Thr Asn Gln Gly Ala Pro Thr Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Lys
                85                  90                  95

Ala Phe Thr Arg Gly Asp Asp Tyr Trp Gly Gln Gly Thr Leu Val Thr
            100                 105                 110

Val Ser Ser
        115

<210> SEQ ID NO 13
<211> LENGTH: 227
<212> TYPE: PRT
<213> ORGANISM: Artificial Sequence
<220> FEATURE:
<223> OTHER INFORMATION: Synthetic Sequence

<400> SEQUENCE: 13

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

```
Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Thr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 14
<211> LENGTH: 227
<212> TYPE: PRT
<213> ORGANISM: Artificial Sequence
<220> FEATURE:
<223> OTHER INFORMATION: Synthetic Sequence

<400> SEQUENCE: 14

Asp Lys Thr His Thr Cys Pro Pro Cys Pro Ala Pro Glu Ala Ala Gly
 1               5                  10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Tyr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

```
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 15
<211> LENGTH: 227
<212> TYPE: PRT
<213> ORGANISM: Artificial Sequence
<220> FEATURE:
<223> OTHER INFORMATION: Synthetic Sequence

<400> SEQUENCE: 15

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 16
<211> LENGTH: 227
<212> TYPE: PRT
<213> ORGANISM: Artificial Sequence
<220> FEATURE:
<223> OTHER INFORMATION: Synthetic Sequence

<400> SEQUENCE: 16

Asp Lys Thr His Thr Cys Pro Pro Cys Pro Ala Pro Glu Ala Ala Gly
```

```
1               5                   10                  15
Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
                35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
                180                 185                 190

Asp Lys Ser Arg Trp Gln Gln Gly Asn Val Phe Ser Cys Ser Val Met
                195                 200                 205

His Glu Ala Leu His Asn His Tyr Thr Gln Lys Ser Leu Ser Leu Ser
    210                 215                 220

Pro Gly Lys
225

<210> SEQ ID NO 17
<211> LENGTH: 487
<212> TYPE: PRT
<213> ORGANISM: Artificial Sequence
<220> FEATURE:
<223> OTHER INFORMATION: Synthetic Sequence

<400> SEQUENCE: 17

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Phe Ser Ser Ile Asn
                20                  25                  30

Val Met Gly Trp Tyr Arg Gln Ala Pro Gly Lys Glu Arg Glu Leu Val
                35                  40                  45

Ala Arg Ile Thr Asn Leu Gly Leu Pro Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Tyr
                85                  90                  95

Leu Val Ala Leu Lys Ala Glu Tyr Trp Gly Gln Gly Thr Leu Val Thr
                100                 105                 110

Val Ser Ser Gly Gly Ser Gly Gly Ser Gly Gly Ser Gly Gly Ser Gly
                115                 120                 125

Gly Ser Asp Val Gln Leu Val Glu Ser Gly Gly Gly Leu Val Gln Pro
```

```
                130             135             140
Gly Gly Ser Leu Arg Leu Ser Cys Ala Ala Ser Gly Ser Phe Ser Ser
145                 150                 155                 160

Ile Asn Val Met Gly Trp Tyr Arg Gln Ala Pro Gly Lys Glu Arg Glu
                165                 170                 175

Leu Val Ala Arg Ile Thr Asn Leu Gly Leu Pro Asn Tyr Ala Asp Ser
            180                 185                 190

Val Lys Gly Arg Phe Thr Ile Ser Arg Asp Asn Ser Lys Asn Thr Val
        195                 200                 205

Tyr Leu Gln Met Asn Ser Leu Arg Pro Glu Asp Thr Ala Val Tyr Tyr
    210                 215                 220

Cys Tyr Leu Val Ala Leu Lys Ala Glu Tyr Trp Gly Gln Gly Thr Leu
225                 230                 235                 240

Val Thr Val Ser Ser Gly Gly Ser Gly Gly Ser Gly Ser Gly Gly
                245                 250                 255

Ser Gly Gly Ser Asp Lys Thr His Thr Cys Pro Pro Cys Pro Ala Pro
                260                 265                 270

Glu Ala Ala Gly Gly Pro Ser Val Phe Leu Phe Pro Pro Lys Pro Lys
            275                 280                 285

Asp Thr Leu Met Ile Ser Arg Thr Pro Glu Val Thr Cys Val Val Val
290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                325                 330                 335

Asn Ser Thr Tyr Arg Val Val Ser Val Leu Thr Val Leu His Gln Asp
            340                 345                 350

Trp Leu Asn Gly Lys Glu Tyr Lys Cys Gln Val Ser Asn Lys Ala Leu
        355                 360                 365

Pro Ala Pro Ile Glu Lys Thr Ile Ser Lys Ala Lys Gly Gln Pro Arg
    370                 375                 380

Glu Pro Gln Val Cys Thr Leu Pro Pro Ser Arg Asp Glu Leu Thr Lys
385                 390                 395                 400

Asn Gln Val Ser Leu Ser Cys Ala Val Lys Gly Phe Tyr Pro Ser Asp
                405                 410                 415

Ile Ala Val Glu Trp Glu Ser Asn Gly Gln Pro Glu Asn Asn Tyr Lys
            420                 425                 430

Thr Thr Pro Pro Val Leu Asp Ser Asp Gly Ser Phe Phe Leu Val Ser
        435                 440                 445

Lys Leu Thr Val Asp Lys Ser Arg Trp Gln Gln Gly Asn Val Phe Ser
    450                 455                 460

Cys Ser Val Met His Glu Ala Leu His Asn His Tyr Thr Gln Lys Ser
465                 470                 475                 480

Leu Ser Leu Ser Pro Gly Lys
                485

<210> SEQ ID NO 18
<211> LENGTH: 487
<212> TYPE: PRT
<213> ORGANISM: Artificial Sequence
<220> FEATURE:
<223> OTHER INFORMATION: Synthetic Sequence

<400> SEQUENCE: 18

Asp Val Gln Leu Val Glu Ser Gly Gly Gly Leu Val Gln Pro Gly Gly
```

```
1               5                   10                  15
Ser Leu Arg Leu Ser Cys Ala Ala Ser Gly Ser Phe Ser Ser Ile Asn
                20                  25                  30
Val Met Gly Trp Tyr Arg Gln Ala Pro Gly Lys Glu Arg Glu Leu Val
                35                  40                  45
Ala Arg Ile Thr Asn Leu Gly Leu Pro Asn Tyr Ala Asp Ser Val Lys
50                  55                  60
Gly Arg Phe Thr Ile Ser Arg Asp Asn Ser Lys Asn Thr Val Tyr Leu
65                  70                  75                  80
Gln Met Asn Ser Leu Arg Pro Glu Asp Thr Ala Val Tyr Tyr Cys Tyr
                85                  90                  95
Leu Val Ala Leu Lys Ala Glu Tyr Trp Gly Gln Gly Thr Leu Val Thr
                100                 105                 110
Val Ser Ser Gly Gly Ser Gly Gly Ser Gly Gly Ser Gly Gly Ser Gly
                115                 120                 125
Gly Ser Asp Lys Thr His Thr Cys Pro Pro Cys Pro Ala Pro Glu Ala
                130                 135                 140
Ala Gly Gly Pro Ser Val Phe Leu Phe Pro Pro Lys Pro Lys Asp Thr
145                 150                 155                 160
Leu Met Ile Ser Arg Thr Pro Glu Val Thr Cys Val Val Val Asp Val
                165                 170                 175
Ser His Glu Asp Pro Glu Val Lys Phe Asn Trp Tyr Val Asp Gly Val
                180                 185                 190
Glu Val His Asn Ala Lys Thr Lys Pro Arg Glu Glu Gln Tyr Asn Ser
                195                 200                 205
Thr Tyr Arg Val Val Ser Val Leu Thr Val Leu His Gln Asp Trp Leu
                210                 215                 220
Asn Gly Lys Glu Tyr Lys Cys Gln Val Ser Asn Lys Ala Leu Pro Ala
225                 230                 235                 240
Pro Ile Glu Lys Thr Ile Ser Lys Ala Lys Gly Gln Pro Arg Glu Pro
                245                 250                 255
Gln Val Cys Thr Leu Pro Pro Ser Arg Asp Glu Leu Thr Lys Asn Gln
                260                 265                 270
Val Ser Leu Ser Cys Ala Val Lys Gly Phe Tyr Pro Ser Asp Ile Ala
                275                 280                 285
Val Glu Trp Glu Ser Asn Gly Gln Pro Glu Asn Asn Tyr Lys Thr Thr
                290                 295                 300
Pro Pro Val Leu Asp Ser Asp Gly Ser Phe Phe Leu Val Ser Lys Leu
305                 310                 315                 320
Thr Val Asp Lys Ser Arg Trp Gln Gln Gly Asn Val Phe Ser Cys Ser
                325                 330                 335
Val Met His Glu Ala Leu His Asn His Tyr Thr Gln Lys Ser Leu Ser
                340                 345                 350
Leu Ser Pro Gly Lys Gly Gly Ser Gly Gly Ser Gly Gly Ser Gly Gly
                355                 360                 365
Ser Gly Gly Ser Asp Val Gln Leu Val Glu Ser Gly Gly Gly Leu Val
                370                 375                 380
Gln Pro Gly Gly Ser Leu Arg Leu Ser Cys Ala Ala Ser Gly Ser Phe
385                 390                 395                 400
Ser Ser Ile Asn Val Met Gly Trp Tyr Arg Gln Ala Pro Gly Lys Glu
                405                 410                 415
Arg Glu Leu Val Ala Arg Ile Thr Asn Leu Gly Leu Pro Asn Tyr Ala
                420                 425                 430
```

```
Asp Ser Val Lys Gly Arg Phe Thr Ile Ser Arg Asp Asn Ser Lys Asn
            435                 440                 445

Thr Val Tyr Leu Gln Met Asn Ser Leu Arg Pro Glu Asp Thr Ala Val
    450                 455                 460

Tyr Tyr Cys Tyr Leu Val Ala Leu Lys Ala Glu Tyr Trp Gly Gln Gly
465                 470                 475                 480

Thr Leu Val Thr Val Ser Ser
                485

<210> SEQ ID NO 19
<211> LENGTH: 553
<212> TYPE: PRT
<213> ORGANISM: Artificial Sequence
<220> FEATURE:
<223> OTHER INFORMATION: Synthetic Sequence

<400> SEQUENCE: 19

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Phe Ser Ser Ile Asn
            20                  25                  30

Val Met Gly Trp Tyr Arg Gln Ala Pro Gly Lys Arg Glu Leu Val
        35                  40                  45

Ala Arg Ile Thr Asn Leu Gly Leu Pro Asn Tyr Ala Asp Ser Val Lys
50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Tyr
                85                  90                  95

Leu Val Ala Leu Lys Ala Glu Tyr Trp Gly Gln Gly Thr Leu Val Thr
            100                 105                 110

Val Ser Ser Gly Gly Ser Gly Gly Ser Gly Gly Ser Gly Gly Ser Gly
        115                 120                 125

Gly Ser Asp Lys Thr His Thr Cys Pro Pro Cys Pro Ala Pro Glu Ala
130                 135                 140

Ala Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
210                 215                 220

Asn Gly Lys Glu Tyr Lys Cys Gln Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Cys Arg Asp Glu Leu Thr Lys Asn Gln
            260                 265                 270

Val Ser Leu Trp Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
290                 295                 300
```

```
Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
            325                 330                 335

Val Met His Glu Ala Leu His Asn His Tyr Thr Gln Lys Ser Leu Ser
        340                 345                 350

Leu Ser Pro Gly Lys Gly Gly Ser Gly Gly Ser Gly Gly Ser Gly Gly
    355                 360                 365

Ser Gly Gly Ser Gly Gly Ser Gly Gly Ser Gly Gly Ser Gly Gly Ser
370                 375                 380

Gly Gly Ser Gly Cys Asp Leu Pro Gln Thr His Ser Leu Gly Ser Arg
385                 390                 395                 400

Arg Thr Leu Met Leu Leu Ala Gln Met Arg Arg Ile Ser Leu Phe Ser
                405                 410                 415

Cys Leu Lys Asp Arg His Asp Phe Gly Phe Pro Gln Glu Glu Phe Gly
            420                 425                 430

Asn Gln Phe Gln Lys Ala Glu Thr Ile Pro Val Leu His Glu Met Ile
        435                 440                 445

Gln Gln Ile Phe Asn Leu Phe Ser Thr Lys Asp Ser Ser Ala Ala Trp
    450                 455                 460

Asp Glu Thr Leu Leu Asp Lys Phe Tyr Thr Glu Leu Tyr Gln Gln Leu
465                 470                 475                 480

Asn Asp Leu Glu Ala Cys Val Ile Gln Gly Val Gly Val Thr Glu Thr
                485                 490                 495

Pro Leu Met Lys Glu Asp Ser Ile Leu Ala Val Arg Lys Tyr Phe Gln
            500                 505                 510

Arg Ile Thr Leu Tyr Leu Lys Glu Lys Lys Tyr Ser Pro Cys Ala Trp
        515                 520                 525

Glu Val Val Arg Ala Glu Ile Met Ala Ser Phe Ser Leu Ser Thr Asn
    530                 535                 540

Leu Gln Glu Ser Leu Arg Ser Lys Glu
545                 550

<210> SEQ ID NO 20
<211> LENGTH: 487
<212> TYPE: PRT
<213> ORGANISM: Artificial Sequence
<220> FEATURE:
<223> OTHER INFORMATION: Synthetic Sequence

<400> SEQUENCE: 20

Gln Val Gln Leu Gln Glu Ser Gly Gly Gly Leu Val Gln Ala Gly Gly
1               5                   10                  15

Ser Leu Arg Leu Ser Cys Thr Ala Ser Gly Thr Ile Phe Ser Ile Asn
            20                  25                  30

Arg Met Asp Trp Phe Arg Gln Ala Pro Gly Lys Gln Arg Glu Leu Val
        35                  40                  45

Ala Leu Ile Thr Ser Asp Gly Thr Pro Ala Tyr Ala Asp Ser Ala Lys
    50                  55                  60

Gly Arg Phe Thr Ile Ser Arg Asp Asn Thr Lys Lys Thr Val Ser Leu
65                  70                  75                  80

Gln Met Asn Ser Leu Lys Pro Glu Asp Thr Ala Val Tyr Tyr Cys His
                85                  90                  95

Val Ser Ser Gly Val Tyr Asn Tyr Trp Gly Gln Gly Thr Gln Val Thr
            100                 105                 110
```

Val Ser Ser Gly Gly Ser Gly Gly Ser Gly Gly Ser Gly
            115                 120                 125

Gly Ser Asp Val Gln Leu Val Glu Ser Gly Gly Leu Val Gln Pro
            130                 135                 140

Gly Gly Ser Leu Arg Leu Ser Cys Ala Ala Ser Gly Ser Phe Ser Ser
145                 150                 155                 160

Ile Asn Val Met Gly Trp Tyr Arg Gln Ala Pro Gly Lys Glu Arg Glu
                    165                 170                 175

Leu Val Ala Arg Ile Thr Asn Leu Gly Leu Pro Asn Tyr Ala Asp Ser
                180                 185                 190

Val Lys Gly Arg Phe Thr Ile Ser Arg Asp Asn Ser Lys Asn Thr Val
            195                 200                 205

Tyr Leu Gln Met Asn Ser Leu Arg Pro Glu Asp Thr Ala Val Tyr Tyr
        210                 215                 220

Cys Tyr Leu Val Ala Leu Lys Ala Glu Tyr Trp Gly Gln Gly Thr Leu
225                 230                 235                 240

Val Thr Val Ser Ser Gly Gly Ser Gly Gly Ser Gly Gly Ser Gly Gly
                    245                 250                 255

Ser Gly Gly Ser Asp Lys Thr His Thr Cys Pro Pro Cys Pro Ala Pro
                260                 265                 270

Glu Ala Ala Gly Gly Pro Ser Val Phe Leu Phe Pro Pro Lys Pro Lys
            275                 280                 285

Asp Thr Leu Met Ile Ser Arg Thr Pro Glu Val Thr Cys Val Val Val
        290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Glu Gln Tyr
                    325                 330                 335

Asn Ser Thr Tyr Arg Val Val Ser Val Leu Thr Val Leu His Gln Asp
                340                 345                 350

Trp Leu Asn Gly Lys Glu Tyr Lys Cys Gln Val Ser Asn Lys Ala Leu
            355                 360                 365

Pro Ala Pro Ile Glu Lys Thr Ile Ser Lys Ala Lys Gly Gln Pro Arg
        370                 375                 380

Glu Pro Gln Val Cys Thr Leu Pro Pro Ser Arg Asp Glu Leu Thr Lys
385                 390                 395                 400

Asn Gln Val Ser Leu Ser Cys Ala Val Lys Gly Phe Tyr Pro Ser Asp
                    405                 410                 415

Ile Ala Val Glu Trp Glu Ser Asn Gly Gln Pro Glu Asn Asn Tyr Lys
                420                 425                 430

Thr Thr Pro Pro Val Leu Asp Ser Asp Gly Ser Phe Phe Leu Val Ser
            435                 440                 445

Lys Leu Thr Val Asp Lys Ser Arg Trp Gln Gln Gly Asn Val Phe Ser
        450                 455                 460

Cys Ser Val Met His Glu Ala Leu His Asn His Tyr Thr Gln Lys Ser
465                 470                 475                 480

Leu Ser Leu Ser Pro Gly Lys
                485

<210> SEQ ID NO 21
<211> LENGTH: 487
<212> TYPE: PRT
<213> ORGANISM: Artificial Sequence
<220> FEATURE:

<223> OTHER INFORMATION: Synthetic Sequence

<400> SEQUENCE: 21

```
Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Phe Ser Ser Ile Asn
            20                  25                  30

Val Met Gly Trp Tyr Arg Gln Ala Pro Gly Lys Glu Arg Glu Leu Val
        35                  40                  45

Ala Arg Ile Thr Asn Leu Gly Leu Pro Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Tyr
                85                  90                  95

Leu Val Ala Leu Lys Ala Glu Tyr Trp Gly Gln Gly Thr Leu Val Thr
            100                 105                 110

Val Ser Ser Gly Gly Ser Gly Gly Ser Gly Gly Ser Gly Gly Ser Gly
        115                 120                 125

Gly Ser Asp Lys Thr His Thr Cys Pro Pro Cys Pro Ala Pro Glu Ala
130                 135                 140

Ala Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Gln Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Cys Thr Leu Pro Pro Ser Arg Asp Glu Leu Thr Lys Asn Gln
            260                 265                 270

Val Ser Leu Ser Cys Ala Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Val Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys Gly Gly Ser Gly Gly Ser Gly Gly Ser Gly Gly
        355                 360                 365

Ser Gly Gly Ser Gln Val Gln Leu Gln Glu Ser Gly Gly Gly Leu Val
    370                 375                 380

Gln Ala Gly Gly Ser Leu Arg Leu Ser Cys Thr Ala Ser Gly Thr Ile
385                 390                 395                 400
```

```
Phe Ser Ile Asn Arg Met Asp Trp Phe Arg Gln Ala Pro Gly Lys Gln
                405                 410                 415

Arg Glu Leu Val Ala Leu Ile Thr Ser Asp Gly Thr Pro Ala Tyr Ala
            420                 425                 430

Asp Ser Ala Lys Gly Arg Phe Thr Ile Ser Arg Asp Asn Thr Lys Lys
        435                 440                 445

Thr Val Ser Leu Gln Met Asn Ser Leu Lys Pro Glu Asp Thr Ala Val
    450                 455                 460

Tyr Tyr Cys His Val Ser Ser Gly Val Tyr Asn Tyr Trp Gly Gln Gly
465                 470                 475                 480

Thr Gln Val Thr Val Ser Ser
                485
```

<210> SEQ ID NO 22
<211> LENGTH: 553
<212> TYPE: PRT
<213> ORGANISM: Artificial Sequence
<220> FEATURE:
<223> OTHER INFORMATION: Synthetic Sequence

<400> SEQUENCE: 22

```
Gln Val Gln Leu Gln Glu Ser Gly Gly Gly Leu Val Gln Ala Gly Gly
1               5                   10                  15

Ser Leu Arg Leu Ser Cys Thr Ala Ser Gly Thr Ile Phe Ser Ile Asn
            20                  25                  30

Arg Met Asp Trp Phe Arg Gln Ala Pro Gly Lys Gln Arg Glu Leu Val
        35                  40                  45

Ala Leu Ile Thr Ser Asp Gly Thr Pro Ala Tyr Ala Asp Ser Ala Lys
    50                  55                  60

Gly Arg Phe Thr Ile Ser Arg Asp Asn Thr Lys Lys Thr Val Ser Leu
65                  70                  75                  80

Gln Met Asn Ser Leu Lys Pro Glu Asp Thr Ala Val Tyr Tyr Cys His
                85                  90                  95

Val Ser Ser Gly Val Tyr Asn Tyr Trp Gly Gln Gly Thr Gln Val Thr
            100                 105                 110

Val Ser Ser Gly Gly Ser Gly Gly Ser Gly Gly Ser Gly Gly Ser Gly
        115                 120                 125

Gly Ser Asp Lys Thr His Thr Cys Pro Pro Cys Pro Ala Pro Glu Ala
    130                 135                 140

Ala Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Gln Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Cys Arg Asp Glu Leu Thr Lys Asn Gln
            260                 265                 270
```

```
Val Ser Leu Trp Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys Gly Gly Ser Gly Gly Ser Gly Gly Ser Gly Gly
        355                 360                 365

Ser Gly Gly Ser Gly Gly Ser Gly Ser Gly Gly Ser Gly Gly Ser
    370                 375                 380

Gly Gly Ser Gly Cys Asp Leu Pro Gln Thr His Ser Leu Gly Ser Arg
385                 390                 395                 400

Arg Thr Leu Met Leu Leu Ala Gln Met Arg Arg Ile Ser Leu Phe Ser
                405                 410                 415

Cys Leu Lys Asp Arg His Asp Phe Gly Phe Pro Gln Glu Glu Phe Gly
                420                 425                 430

Asn Gln Phe Gln Lys Ala Glu Thr Ile Pro Val Leu His Glu Met Ile
                435                 440                 445

Gln Gln Ile Phe Asn Leu Phe Ser Thr Lys Asp Ser Ser Ala Ala Trp
            450                 455                 460

Asp Glu Thr Leu Leu Asp Lys Phe Tyr Thr Glu Leu Tyr Gln Gln Leu
465                 470                 475                 480

Asn Asp Leu Glu Ala Cys Val Ile Gln Gly Val Gly Val Thr Glu Thr
                485                 490                 495

Pro Leu Met Lys Glu Asp Ser Ile Leu Ala Val Arg Lys Tyr Phe Gln
                500                 505                 510

Arg Ile Thr Leu Tyr Leu Lys Glu Lys Lys Tyr Ser Pro Cys Ala Trp
            515                 520                 525

Glu Val Val Arg Ala Glu Ile Met Ala Ser Phe Ser Leu Ser Thr Asn
    530                 535                 540

Leu Gln Glu Ser Leu Arg Ser Lys Glu
545                 550

<210> SEQ ID NO 23
<211> LENGTH: 647
<212> TYPE: PRT
<213> ORGANISM: Artificial Sequence
<220> FEATURE:
<223> OTHER INFORMATION: Synthetic Sequence

<400> SEQUENCE: 23

Met Lys Leu Pro Val Arg Leu Leu Val Leu Met Phe Trp Ile Pro Ala
1               5                   10                  15

Ser Ser Ser Asp Lys Thr His Thr Cys Pro Pro Cys Pro Ala Pro Glu
                20                  25                  30

Ala Ala Gly Gly Pro Ser Val Phe Leu Phe Pro Pro Lys Pro Lys Asp
            35                  40                  45

Thr Leu Met Ile Ser Arg Thr Pro Glu Val Thr Cys Val Val Val Asp
        50                  55                  60

Val Ser His Glu Asp Pro Glu Val Lys Phe Asn Trp Tyr Val Asp Gly
65                  70                  75                  80
```

-continued

```
Val Glu Val His Asn Ala Lys Thr Lys Pro Arg Glu Glu Gln Tyr Asn
                 85                  90                  95

Ser Thr Tyr Arg Val Val Ser Val Leu Thr Val Leu His Gln Asp Trp
            100                 105                 110

Leu Asn Gly Lys Glu Tyr Lys Cys Lys Val Ser Asn Lys Ala Leu Gly
        115                 120                 125

Ala Pro Ile Glu Lys Thr Ile Ser Lys Ala Lys Gly Gln Pro Arg Glu
    130                 135                 140

Pro Gln Val Tyr Thr Leu Pro Pro Ser Arg Asp Glu Leu Thr Lys Asn
145                 150                 155                 160

Gln Val Ser Leu Thr Cys Leu Val Lys Gly Phe Tyr Pro Ser Asp Ile
                165                 170                 175

Ala Val Glu Trp Glu Ser Asn Gly Gln Pro Glu Asn Asn Tyr Lys Thr
            180                 185                 190

Thr Pro Pro Val Leu Asp Ser Asp Gly Ser Phe Phe Leu Tyr Ser Lys
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Lys Ser Leu
225                 230                 235                 240

Ser Leu Ser Pro Gly Lys Gly Gly Ser Gly Gly Ser Gly Gly Ser Gly
                245                 250                 255

Gly Ser Gly Gly Ser Gly Gly Ser Gly Gly Ser Gly Gly Ser Gly Gly
            260                 265                 270

Ser Gly Gly Ser Gly Gly Ser Gly Gly Ser Gly Gly Ser Gly Gly Ser
        275                 280                 285

Gly Gly Ser Gly Gly Ser Gly Gly Ser Gly Gly Ser Gly Gly Ser Gly
    290                 295                 300

Gly Ser Gln Val Gln Leu Gln Glu Ser Gly Gly Gly Leu Val Gln Pro
305                 310                 315                 320

Gly Gly Ser Leu Arg Leu Ser Cys Ala Ala Ser Gly Arg Ile Phe Ser
                325                 330                 335

Val Asn Ala Met Gly Trp Tyr Arg Gln Ala Pro Gly Lys Gln Arg Glu
            340                 345                 350

Leu Val Ala Ala Ile Thr Asn Gln Gly Ala Pro Thr Tyr Ala Asp Ser
        355                 360                 365

Val Lys Gly Arg Phe Thr Ile Ser Arg Asp Asn Ala Gly Asn Thr Val
    370                 375                 380

Tyr Leu Gln Met Asn Ser Leu Arg Pro Glu Asp Thr Ala Val Tyr Tyr
385                 390                 395                 400

Cys Lys Ala Phe Thr Arg Gly Asp Asp Tyr Trp Gly Gln Gly Thr Gln
                405                 410                 415

Val Thr Val Ser Ser Gly Gly Ser Gly Gly Ser Gly Gly Ser Gly Gly
            420                 425                 430

Ser Gly Gly Ser Gly Gly Ser Gly Gly Ser Gly Gly Ser Gly Gly Ser
        435                 440                 445

Gly Gly Ser Gly Gly Ser Gly Gly Ser Gly Gly Ser Gly Gly Ser Gly
    450                 455                 460

Gly Ser Gly Gly Ser Gly Gly Ser Gly Gly Ser Gly Gly Ser Gly Gly
465                 470                 475                 480

Ser Gly Cys Asp Leu Pro Gln Thr His Ser Leu Gly Ser Arg Arg Thr
                485                 490                 495

Leu Met Leu Leu Ala Gln Met Arg Lys Ile Ser Leu Phe Ser Cys Leu
```

```
            500                 505                 510
Lys Asp Arg His Asp Phe Gly Phe Pro Gln Glu Glu Phe Gly Asn Gln
            515                 520                 525

Phe Gln Lys Ala Glu Thr Ile Pro Val Leu His Glu Met Ile Gln Gln
            530                 535                 540

Ile Phe Asn Leu Phe Ser Thr Lys Asp Ser Ser Ala Ala Trp Asp Glu
545                 550                 555                 560

Thr Leu Leu Asp Lys Phe Tyr Thr Glu Leu Tyr Gln Gln Leu Asn Asp
            565                 570                 575

Leu Glu Ala Cys Val Ile Gln Gly Val Gly Val Thr Glu Thr Pro Leu
            580                 585                 590

Met Lys Glu Asp Ser Ile Leu Ala Val Arg Lys Tyr Phe Gln Arg Ile
            595                 600                 605

Thr Leu Tyr Leu Lys Glu Lys Lys Tyr Ser Pro Cys Ala Trp Glu Val
            610                 615                 620

Val Arg Ala Glu Ile Met Ala Ser Phe Ser Leu Ser Thr Asn Leu Gln
625                 630                 635                 640

Glu Ser Leu Arg Ser Lys Glu
            645

<210> SEQ ID NO 24
<211> LENGTH: 647
<212> TYPE: PRT
<213> ORGANISM: Artificial Sequence
<220> FEATURE:
<223> OTHER INFORMATION: Synthetic Sequence

<400> SEQUENCE: 24

Met Gly Trp Ser Cys Ile Ile Phe Phe Leu Val Ala Thr Ala Thr Gly
1               5                   10                  15

Val His Ser Gln Val Gln Leu Gln Glu Ser Gly Gly Gly Leu Val Gln
            20                  25                  30

Pro Gly Gly Ser Leu Arg Leu Ser Cys Ala Ala Ser Gly Arg Ile Phe
        35                  40                  45

Ser Val Asn Ala Met Gly Trp Tyr Arg Gln Ala Pro Gly Lys Gln Arg
    50                  55                  60

Glu Leu Val Ala Ala Ile Thr Asn Gln Gly Ala Pro Thr Tyr Ala Asp
65                  70                  75                  80

Ser Val Lys Gly Arg Phe Thr Ile Ser Arg Asp Asn Ala Gly Asn Thr
                85                  90                  95

Val Tyr Leu Gln Met Asn Ser Leu Arg Pro Glu Asp Thr Ala Val Tyr
            100                 105                 110

Tyr Cys Lys Ala Phe Thr Arg Gly Asp Asp Tyr Trp Gly Gln Gly Thr
        115                 120                 125

Gln Val Thr Val Ser Ser Gly Gly Gly Gly Ser Gly Gly Gly Ser Gly
    130                 135                 140

Gly Ser Gly Gly Ser Gly Gly Ser Gly Gly Ser Gly Gly Ser Gly Gly
145                 150                 155                 160

Ser Gly Gly Ser Gly Gly Ser Gly Gly Ser Gly Gly Ser Gly Gly Ser
                165                 170                 175

Gly Gly Ser Gly Gly Ser Gly Gly Ser Gly Gly Ser Gly Gly Ser Gly
            180                 185                 190

Gly Ser Asp Lys Thr His Thr Cys Pro Pro Cys Pro Ala Pro Glu Ala
        195                 200                 205

Ala Gly Gly Pro Ser Val Phe Leu Phe Pro Pro Lys Pro Lys Asp Thr
```

```
            210                 215                 220
Leu Met Ile Ser Arg Thr Pro Glu Val Thr Cys Val Val Asp Val
225                 230                 235                 240

Ser His Glu Asp Pro Glu Val Lys Phe Asn Trp Tyr Val Asp Gly Val
                    245                 250                 255

Glu Val His Asn Ala Lys Thr Lys Pro Arg Glu Glu Gln Tyr Asn Ser
                260                 265                 270

Thr Tyr Arg Val Val Ser Val Leu Thr Val Leu His Gln Asp Trp Leu
            275                 280                 285

Asn Gly Lys Glu Tyr Lys Cys Lys Val Ser Asn Lys Ala Leu Gly Ala
            290                 295                 300

Pro Ile Glu Lys Thr Ile Ser Lys Ala Lys Gly Gln Pro Arg Glu Pro
305                 310                 315                 320

Gln Val Tyr Thr Leu Pro Pro Ser Arg Asp Glu Leu Thr Lys Asn Gln
                325                 330                 335

Val Ser Leu Thr Cys Leu Val Lys Gly Phe Tyr Pro Ser Asp Ile Ala
                340                 345                 350

Val Glu Trp Glu Ser Asn Gly Gln Pro Glu Asn Asn Tyr Lys Thr Thr
            355                 360                 365

Pro Pro Val Leu Asp Ser Asp Gly Ser Phe Phe Leu Tyr Ser Lys Leu
370                 375                 380

Thr Val Asp Lys Ser Arg Trp Gln Gln Gly Asn Val Phe Ser Cys Ser
385                 390                 395                 400

Val Met His Glu Ala Leu His Asn His Tyr Thr Gln Lys Ser Leu Ser
                405                 410                 415

Leu Ser Pro Gly Lys Gly Gly Ser Gly Gly Ser Gly Gly Ser Gly Gly
                420                 425                 430

Ser Gly Gly Ser Gly Gly Ser Gly Gly Ser Gly Gly Ser Gly Gly Ser
            435                 440                 445

Gly Gly Ser Gly Gly Ser Gly Gly Ser Gly Gly Ser Gly Gly Ser Gly
            450                 455                 460

Gly Ser Gly Gly Ser Gly Gly Ser Gly Gly Ser Gly Gly Ser Gly Gly
465                 470                 475                 480

Ser Gly Cys Asp Leu Pro Gln Thr His Ser Leu Gly Ser Arg Arg Thr
                485                 490                 495

Leu Met Leu Leu Ala Gln Met Arg Lys Ile Ser Leu Phe Ser Cys Leu
                500                 505                 510

Lys Asp Arg His Asp Phe Gly Phe Pro Gln Glu Glu Phe Gly Asn Gln
                515                 520                 525

Phe Gln Lys Ala Glu Thr Ile Pro Val Leu His Glu Met Ile Gln Gln
            530                 535                 540

Ile Phe Asn Leu Phe Ser Thr Lys Asp Ser Ser Ala Ala Trp Asp Glu
545                 550                 555                 560

Thr Leu Leu Asp Lys Phe Tyr Thr Glu Leu Tyr Gln Gln Leu Asn Asp
                565                 570                 575

Leu Glu Ala Cys Val Ile Gln Gly Val Gly Val Thr Glu Thr Pro Leu
                580                 585                 590

Met Lys Glu Asp Ser Ile Leu Ala Val Arg Lys Tyr Phe Gln Arg Ile
            595                 600                 605

Thr Leu Tyr Leu Lys Glu Lys Lys Tyr Ser Pro Cys Ala Trp Glu Val
            610                 615                 620

Val Arg Ala Glu Ile Met Ala Ser Phe Ser Leu Ser Thr Asn Leu Gln
625                 630                 635                 640
```

Glu Ser Leu Arg Ser Lys Glu
                645

<210> SEQ ID NO 25
<211> LENGTH: 353
<212> TYPE: PRT
<213> ORGANISM: Artificial Sequence
<220> FEATURE:
<223> OTHER INFORMATION: Synthetic Sequence

<400> SEQUENCE: 25

Gln Val Gln Leu Gln Glu Ser Gly Gly Gly Leu Val Gln Pro Gly Gly
1               5                   10                  15

Ser Leu Arg Leu Ser Cys Ala Ala Ser Gly Arg Ile Phe Ser Val Asn
            20                  25                  30

Ala Met Gly Trp Tyr Arg Gln Ala Pro Gly Lys Gln Arg Glu Leu Val
        35                  40                  45

Ala Ala Ile Thr Asn Gln Gly Ala Pro Thr Tyr Ala Asp Ser Val Lys
    50                  55                  60

Gly Arg Phe Thr Ile Ser Arg Asp Asn Ala Gly Asn Thr Val Tyr Leu
65                  70                  75                  80

Gln Met Asn Ser Leu Arg Pro Glu Asp Thr Ala Val Tyr Tyr Cys Lys
                85                  90                  95

Ala Phe Thr Arg Gly Asp Asp Tyr Trp Gly Gln Gly Thr Gln Val Thr
            100                 105                 110

Val Ser Ser Val Asp Gly Gly Ser Gly Gly Ser Gly Gly Ser Gly Gly
        115                 120                 125

Ser Gly Gly Ser Gly Gly Ser Arg Ser Gly Gly Ser Gly Gly Ser Gly
    130                 135                 140

Gly Ser Gly Gly Ser Gly Gly Ser Gly Gly Ser Gly Gly Ser Gly Gly
145                 150                 155                 160

Ser Gly Gly Ser Gly Gly Ser Gly Gly Ser Gly Gly Ser Gly Gly Ser
                165                 170                 175

Ala Ala Ala Met Cys Asp Leu Pro Gln Thr His Ser Leu Gly Ser Arg
            180                 185                 190

Arg Thr Leu Met Leu Leu Ala Gln Met Arg Arg Ile Ser Leu Phe Ser
        195                 200                 205

Cys Leu Lys Asp Arg His Asp Phe Gly Phe Pro Gln Glu Glu Phe Gly
    210                 215                 220

Asn Gln Phe Gln Lys Ala Glu Thr Ile Pro Val Leu His Glu Met Ile
225                 230                 235                 240

Gln Gln Ile Phe Asn Leu Phe Ser Thr Lys Asp Ser Ser Ala Ala Trp
                245                 250                 255

Asp Glu Thr Leu Leu Asp Lys Phe Tyr Thr Glu Leu Tyr Gln Gln Leu
            260                 265                 270

Asn Asp Leu Glu Ala Cys Val Ile Gln Gly Val Gly Val Thr Glu Thr
        275                 280                 285

Pro Leu Met Lys Glu Asp Ser Ile Leu Ala Val Arg Lys Tyr Phe Gln
    290                 295                 300

Arg Ile Thr Leu Tyr Leu Lys Glu Lys Tyr Ser Pro Cys Ala Trp
305                 310                 315                 320

Glu Val Val Arg Ala Glu Ile Met Ala Ser Phe Ser Leu Ser Thr Asn
                325                 330                 335

Leu Gln Glu Ser Leu Arg Ser Lys Glu Leu Glu His His His His
            340                 345                 350

His

<210> SEQ ID NO 26
<211> LENGTH: 402
<212> TYPE: PRT
<213> ORGANISM: Artificial Sequence
<220> FEATURE:
<223> OTHER INFORMATION: Synthetic Sequence

<400> SEQUENCE: 26

```
Gln Val Gln Leu Gln Glu Ser Gly Gly Gly Leu Val His Pro Gly Gly
1               5                   10                  15

Ser Leu Arg Leu Ser Cys Ala Ala Ser Gly Ser Phe Ser Ser Ile Asn
            20                  25                  30

Val Met Gly Trp Tyr Arg Gln Ala Pro Gly Lys Glu Arg Glu Leu Val
        35                  40                  45

Ala Arg Ile Thr Asn Leu Gly Leu Pro Asn Tyr Ala Asp Ser Val Thr
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Tyr
                85                  90                  95

Leu Val Ala Leu Lys Ala Glu Tyr Trp Gly Gln Gly Thr Gln Val Thr
            100                 105                 110

Val Ser Ser Gly Gly Ser Gly Gly Ser Gly Gly Ser Gly Gly Ser Gly
        115                 120                 125

Gly Ser Gly Gly Ser Gly Gly Ser Gly Gly Ser Gly Gly Ser Gly Gly
    130                 135                 140

Ser Gly Gly Ser Gly Gly Ser Gly Gly Ser Gly Gly Ser Gly Gly Ser
145                 150                 155                 160

Gly Gly Ser Gly Gly Ser Gly Gly Ser Gly Gly Ser Gly Gly Ser Asp
                165                 170                 175

Lys Thr His Thr Cys Pro Pro Cys Pro Ala Pro Glu Ala Ala Gly Gly
            180                 185                 190

Pro Ser Val Phe Leu Phe Pro Pro Lys Pro Lys Asp Thr Leu Met Ile
        195                 200                 205

Ser Arg Thr Pro Glu Val Thr Cys Val Val Val Asp Val Ser His Glu
    210                 215                 220

Asp Pro Glu Val Lys Phe Asn Trp Tyr Val Asp Gly Val Glu Val His
225                 230                 235                 240

Asn Ala Lys Thr Lys Pro Arg Glu Glu Gln Tyr Asn Ser Thr Tyr Arg
                245                 250                 255

Val Val Ser Val Leu Thr Val Leu His Gln Asp Trp Leu Asn Gly Lys
            260                 265                 270

Glu Tyr Lys Cys Gln Val Ser Asn Lys Ala Leu Pro Ala Pro Ile Glu
        275                 280                 285

Lys Thr Ile Ser Lys Ala Lys Gly Gln Pro Arg Glu Pro Gln Val Cys
    290                 295                 300

Thr Leu Pro Pro Ser Arg Asp Glu Leu Thr Lys Asn Gln Val Ser Leu
305                 310                 315                 320

Ser Cys Ala Val Lys Gly Phe Tyr Pro Ser Asp Ile Ala Val Glu Trp
                325                 330                 335

Glu Ser Asn Gly Gln Pro Glu Asn Tyr Lys Thr Thr Pro Pro Val
            340                 345                 350
```

```
Leu Asp Ser Asp Gly Ser Phe Phe Leu Val Ser Lys Leu Thr Val Asp
            355                 360                 365

Lys Ser Arg Trp Gln Gln Gly Asn Val Phe Ser Cys Ser Val Met His
    370                 375                 380

Glu Ala Leu His Asn His Tyr Thr Gln Lys Ser Leu Ser Leu Ser Pro
385                 390                 395                 400

Gly Lys

<210> SEQ ID NO 27
<211> LENGTH: 452
<212> TYPE: PRT
<213> ORGANISM: Artificial Sequence
<220> FEATURE:
<223> OTHER INFORMATION: Synthetic Sequence

<400> SEQUENCE: 27

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Gln Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Ser Gly Gly Ser Gly Gly Ser Gly Gly Ser Gly
225                 230                 235                 240

Gly Ser Gly Gly Ser Gly Gly Ser Gly Gly Ser Gly Gly Ser Gly Gly
                245                 250                 255

Ser Gly Gly Ser Gly Gly Ser Gly Gly Ser Gly Gly Ser Gly Gly Ser
            260                 265                 270

Gly Gly Ser Gly Gly Ser Gly Gly Ser Gly Gly Ser Gly Gly Ser Cys
        275                 280                 285

Asp Leu Pro Gln Thr His Ser Leu Gly Ser Arg Arg Thr Leu Met Leu
    290                 295                 300

Leu Ala Gln Met Arg Lys Ile Ser Leu Phe Ser Cys Leu Lys Asp Arg
```

```
               305                 310                 315                 320
       His Asp Phe Gly Phe Pro Gln Glu Glu Phe Gly Asn Gln Phe Gln Lys
                       325                 330                 335

Ala Glu Thr Ile Pro Val Leu His Glu Met Ile Gln Gln Ile Phe Asn
                       340                 345                 350

Leu Phe Ser Thr Lys Asp Ser Ser Ala Ala Trp Asp Glu Thr Leu Leu
                       355                 360                 365

Asp Lys Phe Tyr Thr Glu Leu Tyr Gln Gln Leu Asn Asp Leu Glu Ala
                       370                 375                 380

Cys Val Ile Gln Gly Val Gly Val Glu Thr Pro Leu Met Lys Glu
       385                 390                 395                 400

Asp Ser Ile Leu Ala Val Arg Lys Tyr Phe Gln Arg Ile Thr Leu Tyr
                       405                 410                 415

Leu Lys Glu Lys Lys Tyr Ser Pro Cys Ala Trp Glu Val Val Arg Gly
                       420                 425                 430

Glu Ile Met Arg Ser Phe Ser Leu Ser Thr Asn Leu Gln Glu Ser Leu
                       435                 440                 445

Arg Ser Lys Glu
           450

<210> SEQ ID NO 28
<211> LENGTH: 452
<212> TYPE: PRT
<213> ORGANISM: Artificial Sequence
<220> FEATURE:
<223> OTHER INFORMATION: Synthetic Sequence

<400> SEQUENCE: 28

Asp Lys Thr His Thr Cys Pro Pro Cys Pro Ala Pro Glu Ala Ala Gly
       1               5                   10                  15

Gly Pro Ser Val Phe Leu Phe Pro Pro Lys Pro Lys Asp Thr Leu Met
                       20                  25                  30

Ile Ser Arg Thr Pro Glu Val Thr Cys Val Val Val Asp Val Ser His
                       35                  40                  45

Glu Asp Pro Glu Val Lys Phe Asn Trp Tyr Val Asp Gly Val Glu Val
       50                  55                  60

His Asn Ala Lys Thr Lys Pro Arg Glu Glu Gln Tyr Asn Ser Thr Tyr
       65                  70                  75                  80

Arg Val Val Ser Val Leu Thr Val Leu His Gln Asp Trp Leu Asn Gly
                       85                  90                  95

Lys Glu Tyr Lys Cys Gln Val Ser Asn Lys Ala Leu Pro Ala Pro Ile
                       100                 105                 110

Glu Lys Thr Ile Ser Lys Ala Lys Gly Gln Pro Arg Glu Pro Gln Val
                       115                 120                 125

Tyr Thr Leu Pro Pro Cys Arg Asp Glu Leu Thr Lys Asn Gln Val Ser
                       130                 135                 140

Leu Trp Cys Leu Val Lys Gly Phe Tyr Pro Ser Asp Ile Ala Val Glu
       145                 150                 155                 160

Trp Glu Ser Asn Gly Gln Pro Glu Asn Asn Tyr Lys Thr Thr Pro Pro
                       165                 170                 175

Val Leu Asp Ser Asp Gly Ser Phe Phe Leu Tyr Ser Lys Leu Thr Val
                       180                 185                 190

Asp Lys Ser Arg Trp Gln Gln Gly Asn Val Phe Ser Cys Ser Val Met
                       195                 200                 205

His Glu Ala Leu His Asn His Tyr Thr Gln Lys Ser Leu Ser Leu Ser
```

```
                    210                 215                 220
Pro Gly Lys Gly Gly Ser Gly Gly Ser Gly Gly Ser Gly
225                 230                 235                 240

Gly Ser Gly Gly Ser Gly Gly Ser Gly Gly Ser Gly Gly
                245                 250                 255

Ser Gly Gly Ser Gly Gly Ser Gly Gly Ser Gly Gly Ser
                260                 265                 270

Gly Gly Ser Gly Gly Ser Gly Gly Ser Gly Gly Ser Cys
                275                 280                 285

Asp Leu Pro Gln Thr His Ser Leu Gly Ser Arg Arg Thr Leu Met Leu
    290                 295                 300

Leu Ala Gln Met Arg Lys Ile Ser Leu Phe Ser Cys Leu Lys Asp Arg
305                 310                 315                 320

His Asp Phe Gly Phe Pro Gln Glu Glu Phe Gly Asn Gln Phe Gln Lys
                325                 330                 335

Ala Glu Thr Ile Pro Val Leu His Glu Met Ile Gln Gln Ile Phe Asn
                340                 345                 350

Leu Phe Ser Thr Lys Asp Ser Ser Ala Ala Trp Asp Glu Thr Leu Leu
                355                 360                 365

Asp Lys Phe Tyr Thr Glu Leu Tyr Gln Gln Leu Asn Asp Leu Glu Ala
    370                 375                 380

Cys Val Ile Gln Gly Val Gly Val Glu Thr Pro Leu Met Lys Glu
385                 390                 395                 400

Asp Ser Ile Leu Ala Val Arg Lys Tyr Phe Gln Arg Ile Thr Leu Tyr
                405                 410                 415

Leu Lys Glu Lys Lys Tyr Ser Pro Cys Ala Trp Glu Val Val Arg Ala
                420                 425                 430

Glu Ile Ala Arg Ser Phe Ser Leu Ser Thr Asn Leu Gln Glu Ser Leu
                435                 440                 445

Arg Ser Lys Glu
    450

<210> SEQ ID NO 29
<211> LENGTH: 423
<212> TYPE: PRT
<213> ORGANISM: Artificial Sequence
<220> FEATURE:
<223> OTHER INFORMATION: Synthetic Sequence

<400> SEQUENCE: 29

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
        50                  55                  60

His Asn Ala Lys Thr Lys Pro Arg Glu Glu Gln Tyr Asn Ser Thr Tyr
65              70                  75                  80

Arg Val Val Ser Val Leu Thr Val Leu His Gln Asp Trp Leu Asn Gly
                85                  90                  95

Lys Glu Tyr Lys Cys Gln Val Ser Asn Lys Ala Leu Pro Ala Pro Ile
            100                 105                 110

Glu Lys Thr Ile Ser Lys Ala Lys Gly Gln Pro Arg Glu Pro Gln Val
```

```
            115                 120                 125
Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Ser Gly Gly Ser Gly Gly Ser Gly Gly Ser Gly
225                 230                 235                 240

Gly Ser Gly Gly Ser Gly Gly Ser Gly Gly Ser Gly Gly Ser Gly Gly
                245                 250                 255

Ser Gly Cys Asp Leu Pro Gln Thr His Ser Leu Gly Ser Arg Arg Thr
            260                 265                 270

Leu Met Leu Leu Ala Gln Met Arg Lys Ile Ser Leu Phe Ser Cys Leu
        275                 280                 285

Lys Asp Arg His Asp Phe Gly Phe Pro Gln Glu Glu Phe Gly Asn Gln
    290                 295                 300

Phe Gln Lys Ala Glu Thr Ile Pro Val Leu His Glu Met Ile Gln Gln
305                 310                 315                 320

Ile Phe Asn Leu Phe Ser Thr Lys Asp Ser Ser Ala Ala Trp Asp Glu
                325                 330                 335

Thr Leu Leu Asp Lys Phe Tyr Thr Glu Leu Tyr Gln Gln Leu Asn Asp
            340                 345                 350

Leu Glu Ala Cys Val Ile Gln Gly Val Gly Val Glu Glu Thr Pro Leu
        355                 360                 365

Met Lys Glu Asp Ser Ile Leu Ala Val Arg Lys Tyr Phe Gln Arg Ile
    370                 375                 380

Thr Leu Tyr Leu Lys Glu Lys Lys Tyr Ser Pro Cys Ala Trp Glu Val
385                 390                 395                 400

Val Arg Ala Glu Ile Ala Arg Ser Phe Ser Leu Ser Thr Asn Leu Gln
                405                 410                 415

Glu Ser Leu Arg Ser Lys Glu
            420

<210> SEQ ID NO 30
<211> LENGTH: 423
<212> TYPE: PRT
<213> ORGANISM: Artificial Sequence
<220> FEATURE:
<223> OTHER INFORMATION: Synthetic Sequence

<400> SEQUENCE: 30

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
```

```
                50                  55                  60
His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Gln Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys Gly Gly Ser Gly Gly Ser Gly Gly Ser Gly Gly Ser Gly
225                 230                 235                 240

Gly Ser Gly Gly Ser Gly Gly Ser Gly Gly Ser Gly Gly Ser Gly Gly
                245                 250                 255

Ser Gly Cys Asp Leu Pro Gln Thr His Ser Leu Gly Ser Arg Arg Thr
            260                 265                 270

Leu Met Leu Leu Ala Gln Met Arg Lys Ile Ser Leu Phe Ser Cys Leu
        275                 280                 285

Lys Asp Arg His Asp Phe Gly Phe Pro Gln Glu Glu Phe Gly Asn Gln
290                 295                 300

Phe Gln Lys Ala Glu Thr Ile Pro Val Leu His Glu Met Ile Gln Gln
305                 310                 315                 320

Ile Phe Asn Leu Phe Ser Thr Lys Asp Ser Ser Ala Ala Trp Asp Glu
                325                 330                 335

Thr Leu Leu Asp Lys Phe Tyr Thr Glu Leu Tyr Gln Gln Leu Asn Asp
            340                 345                 350

Leu Glu Ala Cys Val Ile Gln Gly Val Gly Val Thr Glu Thr Pro Leu
        355                 360                 365

Met Lys Glu Asp Ser Ile Leu Ala Val Arg Lys Tyr Phe Gln Arg Ile
370                 375                 380

Thr Leu Tyr Leu Lys Glu Lys Lys Tyr Ser Pro Cys Ala Trp Glu Val
385                 390                 395                 400

Val Arg Ala Glu Ile Ala Arg Ser Phe Ser Leu Ser Thr Asn Leu Gln
                405                 410                 415

Glu Ser Leu Arg Ser Lys Glu
            420

<210> SEQ ID NO 31
<211> LENGTH: 423
<212> TYPE: PRT
<213> ORGANISM: Artificial Sequence
<220> FEATURE:
<223> OTHER INFORMATION: Synthetic Sequence
```

```
<400> SEQUENCE: 31

Asp Lys Thr His Thr Cys Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Gln Val Ser Asn Lys Ala Leu Pro Ala Pro Ile
                100                 105                 110

Glu Lys Thr Ile Ser Lys Ala Lys Gly Gln Pro Arg Glu Pro Gln Val
                115                 120                 125

Tyr Thr Leu Pro Pro Cys Arg Asp Glu Leu Thr Lys Asn Gln Val Ser
            130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Ser Gly Gly Ser Gly Gly Ser Gly Gly Ser Gly
225                 230                 235                 240

Gly Ser Gly Gly Ser Gly Gly Ser Gly Gly Ser Gly Gly Ser Gly Gly
                245                 250                 255

Ser Gly Cys Asp Leu Pro Gln Thr His Ser Leu Gly Ser Arg Arg Thr
            260                 265                 270

Leu Met Leu Leu Ala Gln Met Arg Lys Ile Ser Leu Phe Ser Cys Leu
            275                 280                 285

Lys Asp Arg His Asp Phe Gly Phe Pro Gln Glu Glu Phe Gly Asn Gln
        290                 295                 300

Phe Gln Lys Ala Glu Thr Ile Pro Val Leu His Glu Met Ile Gln Gln
305                 310                 315                 320

Ile Phe Asn Leu Phe Ser Thr Lys Asp Ser Ser Ala Ala Trp Asp Glu
                325                 330                 335

Thr Leu Leu Asp Lys Phe Tyr Thr Glu Leu Tyr Gln Gln Leu Asn Asp
            340                 345                 350

Leu Glu Ala Cys Val Ile Gln Gly Val Gly Val Glu Glu Thr Pro Leu
        355                 360                 365

Met Lys Glu Asp Ser Ile Leu Ala Val Arg Lys Tyr Phe Gln Arg Ile
370                 375                 380

Thr Leu Tyr Leu Lys Glu Lys Lys Tyr Ser Pro Cys Ala Trp Glu Val
385                 390                 395                 400

Val Arg Gly Glu Ile Met Arg Ser Phe Ser Leu Ser Thr Asn Leu Gln
                405                 410                 415
```

-continued

Glu Ser Leu Arg Ser Lys Glu
            420

<210> SEQ ID NO 32
<211> LENGTH: 423
<212> TYPE: PRT
<213> ORGANISM: Artificial Sequence
<220> FEATURE:
<223> OTHER INFORMATION: Synthetic Sequence

<400> SEQUENCE: 32

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Gln Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Ser Gly Gly Ser Gly Gly Ser Gly Gly Ser Gly
225                 230                 235                 240

Gly Ser Gly Gly Ser Gly Gly Ser Gly Gly Ser Gly Gly Ser Gly Gly
                245                 250                 255

Ser Gly Cys Asp Leu Pro Gln Thr His Ser Leu Gly Ser Arg Arg Thr
            260                 265                 270

Leu Met Leu Leu Ala Gln Met Arg Lys Ile Ser Leu Phe Ser Cys Leu
        275                 280                 285

Lys Asp Arg His Asp Phe Gly Phe Pro Gln Glu Glu Phe Gly Asn Gln
    290                 295                 300

Phe Gln Lys Ala Glu Thr Ile Pro Val Leu His Glu Met Ile Gln Gln
305                 310                 315                 320

Ile Phe Asn Leu Phe Ser Thr Lys Asp Ser Ser Ala Ala Trp Asp Glu
                325                 330                 335

Thr Leu Leu Asp Lys Phe Tyr Thr Glu Leu Tyr Gln Gln Leu Asn Asp
            340                 345                 350

```
Leu Glu Ala Cys Val Ile Gln Gly Val Gly Val Thr Glu Thr Pro Leu
            355                 360                 365

Met Lys Glu Asp Ser Ile Leu Ala Val Arg Lys Tyr Phe Gln Arg Ile
    370                 375                 380

Thr Leu Tyr Leu Lys Lys Lys Tyr Ser Pro Cys Ala Trp Glu Val
385                 390                 395                 400

Val Arg Gly Glu Ile Met Arg Ser Phe Ser Leu Ser Thr Asn Leu Gln
                405                 410                 415

Glu Ser Leu Arg Ser Lys Glu
                420
```

<210> SEQ ID NO 33
<211> LENGTH: 423
<212> TYPE: PRT
<213> ORGANISM: Artificial Sequence
<220> FEATURE:
<223> OTHER INFORMATION: Synthetic Sequence

<400> SEQUENCE: 33

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Gln Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Tyr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Ser Gly Gly Ser Gly Gly Ser Gly Gly Ser Gly
225                 230                 235                 240

Gly Ser Gly Gly Ser Gly Gly Ser Gly Gly Ser Gly Gly Ser Gly Gly
                245                 250                 255

Ser Gly Cys Asp Leu Pro Gln Thr His Ser Leu Gly Ser Arg Arg Thr
            260                 265                 270

Leu Met Leu Leu Ala Gln Met Arg Lys Ile Ser Leu Phe Ser Cys Leu
        275                 280                 285
```

```
Lys Asp Arg His Asp Phe Gly Phe Pro Gln Glu Glu Phe Gly Asn Gln
        290                 295                 300

Phe Gln Lys Ala Glu Thr Ile Pro Val Leu His Glu Met Ile Gln Gln
305                 310                 315                 320

Ile Phe Asn Leu Phe Ser Thr Lys Asp Ser Ser Ala Ala Trp Asp Glu
                325                 330                 335

Thr Leu Leu Asp Lys Phe Tyr Thr Glu Leu Tyr Gln Gln Leu Asn Asp
            340                 345                 350

Leu Glu Ala Cys Val Ile Gln Gly Val Gly Val Glu Thr Pro Leu
            355                 360                 365

Met Lys Glu Asp Ser Ile Leu Ala Val Arg Lys Tyr Phe Gln Arg Ile
370                 375                 380

Thr Leu Tyr Leu Lys Glu Lys Lys Tyr Ser Pro Cys Ala Trp Glu Val
385                 390                 395                 400

Val Arg Ala Glu Ile Ala Arg Ser Phe Ser Leu Ser Thr Asn Leu Gln
                405                 410                 415

Glu Ser Leu Arg Ser Lys Glu
            420

<210> SEQ ID NO 34
<211> LENGTH: 423
<212> TYPE: PRT
<213> ORGANISM: Artificial Sequence
<220> FEATURE:
<223> OTHER INFORMATION: Synthetic Sequence

<400> SEQUENCE: 34

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
                20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Gln Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
130                 135                 140

Leu Tyr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220
```

-continued

```
Pro Gly Lys Gly Gly Ser Gly Gly Ser Gly Gly Ser Gly
225                 230             235             240

Gly Ser Gly Gly Ser Gly Gly Ser Gly Gly Ser Gly Gly
            245             250             255

Ser Gly Cys Asp Leu Pro Gln Thr His Ser Leu Gly Ser Arg Arg Thr
        260                 265                 270

Leu Met Leu Leu Ala Gln Met Arg Lys Ile Ser Leu Phe Ser Cys Leu
        275                 280                 285

Lys Asp Arg His Asp Phe Gly Phe Pro Gln Glu Glu Phe Gly Asn Gln
        290                 295                 300

Phe Gln Lys Ala Glu Thr Ile Pro Val Leu His Glu Met Ile Gln Gln
305                 310                 315                 320

Ile Phe Asn Leu Phe Ser Thr Lys Asp Ser Ser Ala Ala Trp Asp Glu
                325                 330                 335

Thr Leu Leu Asp Lys Phe Tyr Thr Glu Leu Tyr Gln Gln Leu Asn Asp
                340                 345                 350

Leu Glu Ala Cys Val Ile Gln Gly Val Gly Val Thr Glu Thr Pro Leu
            355                 360                 365

Met Lys Glu Asp Ser Ile Leu Ala Val Arg Lys Tyr Phe Gln Arg Ile
370                 375                 380

Thr Leu Tyr Leu Lys Glu Lys Lys Tyr Ser Pro Cys Ala Trp Glu Val
385                 390                 395                 400

Val Arg Ala Glu Ile Ala Arg Ser Phe Ser Leu Ser Thr Asn Leu Gln
                405                 410                 415

Glu Ser Leu Arg Ser Lys Glu
            420

<210> SEQ ID NO 35
<211> LENGTH: 423
<212> TYPE: PRT
<213> ORGANISM: Artificial Sequence
<220> FEATURE:
<223> OTHER INFORMATION: Synthetic Sequence

<400> SEQUENCE: 35

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Gln Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Tyr Cys Leu Val Lys Gly Phe Tyr Pro Ser Asp Ile Ala Val Glu
145                 150                 155                 160
```

-continued

```
Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
        180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
    210                 215                 220

Pro Gly Lys Gly Gly Ser Gly Gly Ser Gly Gly Ser Gly Gly Ser Gly
225                 230                 235                 240

Gly Ser Gly Gly Ser Gly Gly Ser Gly Gly Ser Gly Gly Ser Gly Gly
                245                 250                 255

Ser Gly Cys Asp Leu Pro Gln Thr His Ser Leu Gly Ser Arg Arg Thr
            260                 265                 270

Leu Met Leu Leu Ala Gln Met Arg Lys Ile Ser Leu Phe Ser Cys Leu
    275                 280                 285

Lys Asp Arg His Asp Phe Gly Phe Pro Gln Glu Glu Phe Gly Asn Gln
290                 295                 300

Phe Gln Lys Ala Glu Thr Ile Pro Val Leu His Glu Met Ile Gln Gln
305                 310                 315                 320

Ile Phe Asn Leu Phe Ser Thr Lys Asp Ser Ser Ala Ala Trp Asp Glu
                325                 330                 335

Thr Leu Leu Asp Lys Phe Tyr Thr Glu Leu Tyr Gln Gln Leu Asn Asp
            340                 345                 350

Leu Glu Ala Cys Val Ile Gln Gly Val Gly Val Glu Thr Pro Leu
    355                 360                 365

Met Lys Glu Asp Ser Ile Leu Ala Val Arg Lys Tyr Phe Gln Arg Ile
370                 375                 380

Thr Leu Tyr Leu Lys Glu Lys Lys Tyr Ser Pro Cys Ala Trp Glu Val
385                 390                 395                 400

Val Arg Gly Glu Ile Met Arg Ser Phe Ser Leu Ser Thr Asn Leu Gln
                405                 410                 415

Glu Ser Leu Arg Ser Lys Glu
            420
```

```
<210> SEQ ID NO 36
<211> LENGTH: 423
<212> TYPE: PRT
<213> ORGANISM: Artificial Sequence
<220> FEATURE:
<223> OTHER INFORMATION: Synthetic Sequence

<400> SEQUENCE: 36
```

```
Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Gln Val Ser Asn Lys Ala Leu Pro Ala Pro Ile
                100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
        130                 135                 140

Leu Tyr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
210                 215                 220

Pro Gly Lys Gly Gly Ser Gly Gly Ser Gly Gly Ser Gly Gly Ser Gly
225                 230                 235                 240

Gly Ser Gly Ser Gly Gly Ser Gly Gly Ser Gly Gly Ser Gly Gly Gly
            245                 250                 255

Ser Gly Cys Asp Leu Pro Gln Thr His Ser Leu Gly Ser Arg Arg Thr
        260                 265                 270

Leu Met Leu Leu Ala Gln Met Arg Lys Ile Ser Leu Phe Ser Cys Leu
275                 280                 285

Lys Asp Arg His Asp Phe Gly Phe Pro Gln Glu Glu Phe Gly Asn Gln
                290                 295                 300

Phe Gln Lys Ala Glu Thr Ile Pro Val Leu His Glu Met Ile Gln Gln
305                 310                 315                 320

Ile Phe Asn Leu Phe Ser Thr Lys Asp Ser Ser Ala Ala Trp Asp Glu
                325                 330                 335

Thr Leu Leu Asp Lys Phe Tyr Thr Glu Leu Tyr Gln Gln Leu Asn Asp
            340                 345                 350

Leu Glu Ala Cys Val Ile Gln Gly Val Gly Val Thr Glu Thr Pro Leu
        355                 360                 365

Met Lys Glu Asp Ser Ile Leu Ala Val Arg Lys Tyr Phe Gln Arg Ile
370                 375                 380

Thr Leu Tyr Leu Lys Glu Lys Lys Tyr Ser Pro Cys Ala Trp Glu Val
385                 390                 395                 400

Val Arg Gly Glu Ile Met Arg Ser Phe Ser Leu Ser Thr Asn Leu Gln
            405                 410                 415

Glu Ser Leu Arg Ser Lys Glu
            420

<210> SEQ ID NO 37

<400> SEQUENCE: 37

000

<210> SEQ ID NO 38
<211> LENGTH: 227
<212> TYPE: PRT
<213> ORGANISM: Artificial Sequence
<220> FEATURE:
<223> OTHER INFORMATION: Synthetic Sequence
```

<400> SEQUENCE: 38

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Gln Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 39

<400> SEQUENCE: 39

000

<210> SEQ ID NO 40

<400> SEQUENCE: 40

000

<210> SEQ ID NO 41
<211> LENGTH: 422
<212> TYPE: PRT
<213> ORGANISM: Artificial Sequence
<220> FEATURE:
<223> OTHER INFORMATION: Synthetic Sequence

<400> SEQUENCE: 41

Asp Lys Thr His Thr Cys Pro Pro Cys Pro Ala Pro Glu Ala Ala Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
 50                  55                  60

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Gln Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Gly Gly Ser Gly Gly Ser Gly Gly Ser Gly Gly Ser Gly Gly
225                 230                 235                 240

Ser Gly Gly Ser Gly Gly Ser Gly Gly Ser Gly Gly Ser Gly Gly Ser
                245                 250                 255

Gly Cys Asp Leu Pro Gln Thr His Ser Leu Gly Ser Arg Arg Thr Leu
            260                 265                 270

Met Leu Leu Ala Gln Met Arg Arg Ile Ser Leu Phe Ser Cys Leu Lys
        275                 280                 285

Asp Arg His Asp Phe Gly Phe Pro Gln Glu Glu Phe Gly Asn Gln Phe
    290                 295                 300

Gln Lys Ala Glu Thr Ile Pro Val Leu His Glu Met Ile Gln Gln Ile
305                 310                 315                 320

Phe Asn Leu Phe Ser Thr Lys Asp Ser Ser Ala Ala Trp Asp Glu Thr
                325                 330                 335

Leu Leu Asp Lys Phe Tyr Thr Glu Leu Tyr Gln Gln Leu Asn Asp Leu
            340                 345                 350

Glu Ala Cys Val Ile Gln Gly Val Gly Val Thr Glu Thr Pro Leu Met
        355                 360                 365

Lys Glu Asp Ser Ile Leu Ala Val Arg Lys Tyr Phe Gln Arg Ile Thr
    370                 375                 380

Leu Tyr Leu Lys Glu Lys Lys Tyr Ser Pro Cys Ala Trp Glu Val Val
385                 390                 395                 400

Arg Gly Glu Ile Met Arg Ser Phe Ser Leu Ser Thr Asn Leu Gln Glu
                405                 410                 415

Ser Leu Arg Ser Lys Glu
            420

<210> SEQ ID NO 42
<211> LENGTH: 422
<212> TYPE: PRT
<213> ORGANISM: Artificial Sequence
<220> FEATURE:

<223> OTHER INFORMATION: Synthetic Sequence

<400> SEQUENCE: 42

```
Asp Lys Thr His Thr Cys Pro Pro Cys Pro Ala Pro Glu Ala Ala Gly
 1               5                  10                  15
Gly Pro Ser Val Phe Leu Phe Pro Pro Lys Pro Lys Asp Thr Leu Met
             20                  25                  30
Ile Ser Arg Thr Pro Glu Val Thr Cys Val Val Val Asp Val Ser His
         35                  40                  45
Glu Asp Pro Glu Val Lys Phe Asn Trp Tyr Val Asp Gly Val Glu Val
     50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Gln Val Ser Asn Lys Ala Leu Pro Ala Pro Ile
             100                 105                 110
Glu Lys Thr Ile Ser Lys Ala Lys Gly Gln Pro Arg Glu Pro Gln Val
         115                 120                 125
Tyr Thr Leu Pro Pro Cys Arg Asp Glu Leu Thr Lys Asn Gln Val Ser
    130                 135                 140
Leu Trp Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                165                 170                 175
Val Leu Asp Ser Asp Gly Ser Phe Phe Leu Tyr Ser Lys Leu Thr Val
            180                 185                 190
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Gly Gly Ser Gly Gly Ser Gly Gly Ser Gly Gly Ser Gly Gly
225                 230                 235                 240
Ser Gly Gly Ser Gly Gly Ser Gly Gly Ser Gly Gly Ser Gly Gly Ser
                245                 250                 255
Gly Cys Asp Leu Pro Gln Thr His Ser Leu Gly Ser Arg Arg Thr Leu
            260                 265                 270
Met Leu Leu Ala Gln Met Arg Lys Ile Ser Leu Phe Ser Cys Leu Lys
        275                 280                 285
Asp Arg His Asp Phe Gly Phe Pro Gln Glu Glu Phe Gly Asn Gln Phe
    290                 295                 300
Gln Lys Ala Glu Thr Ile Pro Val Leu His Glu Met Ile Gln Gln Ile
305                 310                 315                 320
Phe Asn Leu Phe Ser Thr Lys Asp Ser Ser Ala Ala Trp Asp Glu Thr
                325                 330                 335
Leu Leu Asp Lys Phe Tyr Thr Glu Leu Tyr Gln Gln Leu Asn Asp Leu
            340                 345                 350
Glu Ala Cys Val Ile Gln Gly Val Gly Val Glu Thr Pro Leu Met
        355                 360                 365
Lys Glu Asp Ser Ile Leu Ala Val Arg Lys Tyr Phe Gln Arg Ile Thr
    370                 375                 380
Leu Tyr Leu Lys Glu Lys Lys Tyr Ser Pro Cys Ala Trp Glu Val Val
385                 390                 395                 400
```

Arg Gly Glu Ile Met Arg Ser Phe Ser Leu Ser Thr Asn Leu Gln Glu
                    405                 410                 415

Ser Leu Arg Ser Lys Glu
            420

<210> SEQ ID NO 43
<211> LENGTH: 356
<212> TYPE: PRT
<213> ORGANISM: Artificial Sequence
<220> FEATURE:
<223> OTHER INFORMATION: Synthetic Sequence

<400> SEQUENCE: 43

Asp Val Gln Leu Val Glu Ser Gly Gly Gly Leu Val Gln Pro Gly Gly
1               5                   10                  15

Ser Leu Arg Leu Ser Cys Ala Ala Ser Gly Ser Phe Ser Ser Ile Asn
            20                  25                  30

Val Met Gly Trp Tyr Arg Gln Ala Pro Gly Lys Glu Arg Glu Leu Val
        35                  40                  45

Ala Arg Ile Thr Asn Leu Gly Leu Pro Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Tyr
                85                  90                  95

Leu Val Ala Leu Lys Ala Glu Tyr Trp Gly Gln Gly Thr Leu Val Thr
            100                 105                 110

Val Ser Ser Gly Gly Ser Gly Gly Ser Gly Gly Ser Gly Gly Ser Gly
        115                 120                 125

Gly Ser Asp Lys Thr His Thr Cys Pro Pro Cys Pro Ala Pro Glu Ala
    130                 135                 140

Ala Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Gln Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Cys Thr Leu Pro Pro Ser Arg Asp Glu Leu Thr Lys Asn Gln
            260                 265                 270

Val Ser Leu Ser Cys Ala Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Val Ser Lys Leu
305                 310                 315                 320

Thr Val Asp Lys Ser Arg Trp Gln Gln Gly Asn Val Phe Ser Cys Ser
                325                 330                 335

-continued

```
Val Met His Glu Ala Leu His Asn His Tyr Thr Gln Lys Ser Leu Ser
            340                 345                 350

Leu Ser Pro Gly
        355
```